US010034936B2

(12) United States Patent
Stapleton et al.

(10) Patent No.: US 10,034,936 B2
(45) Date of Patent: Jul. 31, 2018

(54) METHOD OF INDUCING A CROSS-REACTIVE HIV-1 IMMUNE RESPONSE BY ADMINISTERING A COMPOSITION COMPRISING THE GBV-C E2 PROTEIN

(71) Applicants: THE UNIVERSITY OF IOWA RESEARCH FOUNDATION, Iowa City, IA (US); THE UNITED STATES OF AMERICA AS REPRESENTED BY THE SECRETARY OF THE DEPARTMENT OF VETERANS AFFAIRS, Washington, DC (US)

(72) Inventors: Jack T. Stapleton, Iowa City, IA (US); Jinhua Xiang, Iowa City, IA (US); Donna Klinzman, Coralville, IA (US); James H. McLinden, Coralville, IA (US)

(73) Assignees: The University of Iowa Research Foundation, Iowa, IA (US); The United States of America as represented by the Secretary of the Department of Veterans Affairs, Washington, DC (US)

( * ) Notice: Subject to any disclaimer, the term of this patent is extended or adjusted under 35 U.S.C. 154(b) by 347 days.

(21) Appl. No.: 14/460,517

(22) Filed: Aug. 15, 2014

(65) Prior Publication Data

US 2014/0348866 A1 Nov. 27, 2014

Related U.S. Application Data

(62) Division of application No. 12/179,399, filed on Jul. 24, 2008, now Pat. No. 8,858,946, which is a division of application No. 10/862,061, filed on Jun. 4, 2004, now abandoned.

(60) Provisional application No. 60/475,987, filed on Jun. 5, 2003.

(51) Int. Cl.

| | |
|---|---|
| *C07K 14/05* | (2006.01) |
| *A61K 39/29* | (2006.01) |
| *C07K 16/10* | (2006.01) |
| *C07K 14/18* | (2006.01) |
| *A61K 39/00* | (2006.01) |
| *C12N 7/00* | (2006.01) |

(52) U.S. Cl.

CPC .............. *A61K 39/29* (2013.01); *C07K 14/05* (2013.01); *C07K 16/109* (2013.01); *A61K 2039/505* (2013.01); *C07K 14/1841* (2013.01); *C07K 2317/34* (2013.01); *C12N 7/00* (2013.01); *C12N 2770/24222* (2013.01); *C12N 2770/24234* (2013.01)

(58) Field of Classification Search

CPC .. A61K 39/29; C07K 16/109; C07K 14/1841; C12N 2770/24222; C12N 2770/24234

See application file for complete search history.

(56) References Cited

U.S. PATENT DOCUMENTS

| | | | |
|---|---|---|---|
| 5,665,569 | A | 9/1997 | Ohno |
| 5,693,762 | A | 12/1997 | Queen et al. |
| 5,766,840 | A | 6/1998 | Kim et al. |
| 5,821,333 | A | 10/1998 | Carter |
| 5,824,507 | A | 10/1998 | Kim et al. |
| 5,849,532 | A | 12/1998 | Kim et al. |
| 5,856,134 | A | 1/1999 | Kim et al. |
| 5,874,563 | A | 2/1999 | Kim et al. |
| 5,888,773 | A | 3/1999 | Jost et al. |
| 5,889,157 | A | 3/1999 | Pastan et al. |
| 5,981,172 | A | 11/1999 | Simons et al. |
| 6,020,195 | A | 2/2000 | Schmolke et al. |
| 6,051,374 | A | 4/2000 | Simons et al. |
| 6,156,495 | A | 12/2000 | Pilot-Matias et al. |
| 6,387,959 | B1 | 5/2002 | Nottet |
| 6,451,578 | B1 | 9/2002 | Simons et al. |
| 6,558,898 | B1 | 5/2003 | Simons et al. |
| 6,586,568 | B1 | 7/2003 | Simons et al. |
| 6,720,166 | B2 | 4/2004 | Simons et al. |

FOREIGN PATENT DOCUMENTS

| | | |
|---|---|---|
| EP | 0 747 482 | 12/1996 |
| EP | 0 832 901 | 4/1998 |
| WO | WO 1994/018217 | 8/1994 |
| WO | WO 1997/038108 | 10/1997 |
| WO | WO 2001/077157 | 10/2001 |
| WO | WO 2004/037202 | 5/2004 |

OTHER PUBLICATIONS

Bagasra, O., et al., 2012, Potential utility of GB virus type C as a preventive vaccine for HIV-1, Expert Rev. Vaccines 11(3):335-347.*

Mohr, E. L., et al., 2010, GB Virus Type C Envelope Protein Elicits Antibodies That React with a Cellular Antigen on HIV-1 Particles and Neutralize Diverse HIV-1 Isolates, J. Immunol. 185:4496-4505.*

Barouch, D. H., 2008, Challenges in the development of an HIV-1 vaccine, Nature 455:613-619.*

West, Jr., A. P., et al., 2014, Structural Insights on the Role of Antibodies in HIV-1 Vaccine and Therapy, Cell 156:633-648.*

"Infection with GBV-C linked to longer life," *AIDS Alert.* 17:7-8, 2002.

Aarons et al., "Adaptation to blockade of human immunodeficiency virus type 1 entry imposed by the anti-CCRS monoclonal antibody 2D7," *Virol.*, 287(2):382-390, 2001.

(Continued)

*Primary Examiner* — Jeffrey Parkin

(74) *Attorney, Agent, or Firm* — Parker Highlander PLLC

(57) ABSTRACT

GB virus C (GBV-C or hepatitis G virus) is a flavivirus that frequently leads to chronic viremia in humans. The invention provides compositions and methods involving an anti-GBV-C antibody or other GBV-C binding agent, or a GBV-C antigen, for inhibiting and treating HIV infections.

5 Claims, 14 Drawing Sheets

(56) References Cited

OTHER PUBLICATIONS

Anderson et al., "Anit-CD3 + IL-2-stimulated murine killer cells. In vitro generation and in vivo antitumor activity," *J. Immunol.*, 142:1383-1394, 1989.
Aronoff DM, "Using live pathogens to treat infectious diseases: a historical perspective on the relationship between GB virus C and HIV," *Antivir. Ther.* 7:73-80, 2002.
Bansal, "A Summary of the workshop on passive immunization using monoclonal antibodies for HIV/AIDS, held at the National Institute of Allergy and Infectious Diseases, Mar. 10, 2006," *Biol.*, 35(4):367-371, 2007.
Berman et al., "Hiv-1 challenge of chimpanzees immunized with recombinant gp120," *Proc. Natl. Acad. Sci. U S A.*, 85:5200-5204, 1988.
Biron et al., "The 2F5 epitope is helical in the HIV-1 entry inhibitor T-20," *Biochemistry*, 44:13602-13611, 2005.
Cadogan and Dagleish, "HIV immunopathogenesis and strategies for intervention.," *Lancet Infect. Dis.*, 8(11):675-684, 2008.
Cecilia et al., "Neutralization profiles of primary human immunodeficiency virus type 1 isolates in the context of coreceptor usage," *J. Virol.*, 72(9):6988-6996, 1998.
Chakraborty et al. "Viral coinfections among African children infected with human immunodeficiency virus type 1," *Clin. Infect. Dis.* 36:922-924, 2003.
Cohen, "Is an effective HIV vaccine feasible," *Science*, 309(5731):99, 2005.
Coutant et al., "Both lipid environment and pH are critical for determining physiological solution structure of 3-D-conserved epitopes of the HIV-1 gp41-MPER peptide P1," *FASEB Journal*, 22:4338-4351, 2008.
Dawson et al., "Prevalence studies of GB virus-C infection using reverse transcriptase-polymerase chain reaction," *J. Med. Virol.*, 50:97-103, 1996.
Dennison et al., "Stable docking of neutralizing human immunodeficiency virus type 1 gp41 membrane-proximal external region monoclonal antibodies 2F5 and 4E10 is dependent on the membrane immersion depth of their epitope regions," *J. Virology*, 83(19): 10211-10223, 2009.
Ferrantelli et al., "Post-exposure prophylaxis with human monoclonal antibodies prevented SHIV89.6P infection or disease in neonatal macaques," *AIDS*, 17(3): 301-309, 2003.
Fogeda et al., "In vitro infection of human peripheral blood mononuclear cells by GB virus C/hepatitis G virus," *J. Virol.*, 73(5):4052-4061, 1999.
GenBank Accession No. AF070476, "GB virus C variant troglodytes, complete genome," 1998.
GenBank Accession No. AY196904, "Hepatitis G virus isolate 765, complete genome," 2003.
George SL, et al., "Interactions Between GB Virus Type C and HIV," *Curr Infect Dis Rep.* 4:550-558, 2002.
Gray et al., "4E10-resistant variants in a human immunodeficiency virus type 1 subtype C-infected individual with an anti-membrane-proximal external region-neutralizing antibody response," *J Virology*, 82(5):2367-2375, 2008.
Haynes and Alam, "HIV-1 hides an Achilles' heel in virion lipids," *Immunity*, 28:10-12, 2008.
Haynes et al., "Cardiolipin polyspecific autoreactivity in two broadly neutralizing HIV-1 antibodies," *Science*, 308:1906-1908, 2005.
Huarte et al., "Lipid modulation of membrane-bound epitope recognition and blocking by HIV-1 neutralizing antibodies," *FEBS Letters*, 582:3798-3804, 2008.
Johnston and Fauci, "An HIV vaccine—challenges and prospects," *NEJM*, 359: 888-890, 2008.
Joos et al., "Long-term multiple-dose pharmacokinetics of human monoclonal antibodies (MAbs) against human immunodeficiency virus type 1 envelope gp120 (MAb 2G12) and gp41 (MAbs 4E10 and 2F5)," *Antimicrob Agents Chemother.*, 50(5):1773-1779, 2006.
Jung et al., "HIV entry inhibition by the envelope 2 glycoprotein of GB virus C," *AIDS*, 21(5):645-647, 2007.

Koff, "Accelerating HIV vaccine development," *Nature*, 464:161-162, 2010.
Larios et al., "Characterization of a putative fusogenic sequence in the E2 hepatitis G virus protein," *Arch Biochem Biophys*, 442(2):149-159, 2005.
Lefrere et al., "Carriage of GB virus C/hepatitis G virus RNA is associated with a slower immunologic, virologic, and clinical progression of human immunodeficiency virus disease in coinfected persons," *J. Infect. Dis.*, 179:783-789, 1999.
Loeffler et al., "Antitumor effects of interleukin 2 liposomes and anti-CD3-stimulated T-cells against murine MCA-38 hepatic metastasis," *Cancer Res.*, 51:2127-2132, 1991.
Matyas et al., "Lipid binding properties of 4E10, 2F5, WR304 monoclonal antibodies that neutralize HIV-1," *Biochimica et Biophysica Acta*, 1788:660-665, 2009.
McLinden et al., "Characterization of an immunodominant antigenic site on GB virus C glycoprotein E2 that is involved in cell binding," *J. Virol.*, 80(24):12131-12140, 2006.
Mehandru et al., "Adjunctive passive immunotherapy in human immunodeficiency virus type 1-infected individuals treated with antiviral therapy during acute and early infection," *J. Virology*, 81(2): 11016-11031, 2007.
Mohr et al., "GB Virus Type C Envelope Protein E2 Elicits Antibodies That React with a Cellular Antigen on HIV-1 Particles and Neutralize Diverse HIV-1 Isolates," *J. of Immunology*, 185:4496-4505, 2010.
Moore et al., "Zidovudine and the natural history of the acquired immunodeficiency syndrome," *New England J. Med.*, 324(20):1412-1416, 1991.
Nakowitsch et al., "HIV-1 mutants escaping neutralization by the human antibodies 2F5, 2G12, and 4E10: in vitro experiments versus clinical studies," *AIDS*, 19(17): 1957-1966, 2005.
Office Communication issued in U.S. Appl. No. 10/862,061, dated Nov. 20, 2006.
Office Communication issued in U.S. Appl. No. 10/862,061, dated Oct. 1, 2007.
Office Communication issued in U.S. Appl. No. 12/179,399, dated Jan. 31, 2014.
Office Communication issued in U.S. Appl. No. 12/179,399, dated Jul. 9, 2013.
Office Communication issued in U.S. Appl. No. 12/179,399, dated Jan. 2, 2013.
Office Communication issued in U.S. Appl. No. 12/179,399, dated Jun. 7, 2012.
Office Communication issued in U.S. Appl. No. 12/179,399, dated Aug. 4, 2011.
Office Communication issued in U.S. Appl. No. 12/179,399, dated Feb. 28, 2011.
Office Communication issued in U.S. Appl. No. 12/179,399, dated Dec. 8, 2010.
Office Communication issued in U.S. Appl. No. 12/179,399, dated Mar. 24, 2010.
Office Communication issued in U.S. Appl. No. 10/862,061, dated Mar. 9, 2007.
Office Communication, issued in U.S. Appl. No. 10/862,061, dated Jun. 10, 2008.
PCT International Search Report and Written Opinion issued in International Patent Application No. PCT/US2004/017706, dated Jan. 4, 2005.
Ruprecht et al., "Antibody protection: passive immunization of neonates against oral AIDS virus challenge," *Vaccine*, 21:3370-3373, 2003.
Sabin et al., "Effect of coinfection with hepatitis G virus on HIV disease progression in hemophilic men," *J. Acquir. Immune Defic. Syndr.*, 19:546-549, 1998.
Sawyer et al., "Possible beneficial effects of neutralizing antibodies and antibody-dependent, cell-mediated cytotoxicity in human immunodeficiency virus infection," *AIDS Res. Hum. Retroviruses*, 6(3):341-356, 1990.
Schmolke et al., "Identification of hepatitis G virus particles in human serum by E2-specific monoclonal antibodies generated by DNA immunization," *J. Virol.*, 72(5):4541-4545, 1998.

(56) References Cited

OTHER PUBLICATIONS

Seipp et al., "Hepatotrophism of GB virus C (GBV-C): GBV-C replication in human hepatocytes and cells of human hepatoma cell lines," *J. Hepatol*, 30:570-579, 1999.
Self et al., "How specific are therapeutic monoclonal antibodies?," *Lancet.*, 367(9516):1038-1039, 2006.
Shimizu, "Replication of GB virus C (hepatitis G virus) in interferon-resistant daudi cells," *J. Virol.*, 73:8411-8414, 1999.
Srivastava et al., "Neutralizing antibody responses to HIV: role in protective immunity and challenges for vaccine design," *Expert Rev. Vaccines*, 3(4 Suppl.):533-52, 2004.
Stapleton et al., "Prospective comparison of whole-blood- and plasma-based hepatitis C virus RNA detection systems: improved detection using whole blood as the source of viral RNA," *J Clin Microbiol.* 37:484-9, 1999.
Stapleton, "GB virus type C/hepatitis G virus," *Seminars in Liver Disease*, 23(2):137-148, 2003.
Tacke et al., "Humoral immune response to the E2 protein of hepatitis G virus is associated with long-term recovery from infection and reveals a high frequency of hepatitis G virus exposure among healthy blood donors," *Hepatol*, 26(6):1626-1633, 1997.
Thomas et al., "Association of antibody to GB virus C (hepatitis G virus) with viral clearance and protection from reinfection," *J. Infect. Dis.*, 177:539-542, 1998.
Tillmann et al. "GB virus-C infection in patients infected with the human immunodeficiency virus," *Antiviral Res.* 52:83-90, 2001. Review.
Tillmann et al., "Infection with GB virus C and reduced mortality among HIV-infected patients," *N Engl J Med.* 345:715-24, 2001.
Toyoda et al., "Effect of GB virus C/hepatitis G virus coinfection on the course of HIV infection in hemophilia patients in Japan," *J. Acquir. Immune Defic. Syndr.*, 17:209-213, 1998.
Trkola et al., "Delay of HIV-1 rebound after cessation of antiretroviral therapy through passive transfer of human neutralizing antibodies," *Nature Med.*, 11:615-622, 2005.
Voirin et al., "Effects of co-infection with hepatitis C virus and GB virus C on CD4 cell count and HIV-RNA level among HIV-infected patients treated with highly active antiretroviral therapy," *AIDS.* 16:1556-9, 2002.
Walker and Burton, "Toward an AIDS Vaccine," *Science*, 320:760-764, 2008.
West et al., "Single-chain Fv-based anti-HIV proteins: potential and limitations," *J. Virol.*, 86(1):195-202, 2012.
Winkler et al., "Changing the antigen binding specificity by single point mutations of an anti-p24 (HIV-1) antibody," *J. Immunol.*, 165:4505-4514, 2000.
Xiang et al. "Effect of coinfection with GB virus C on survival among patients with HIV infection," *N Engl J Med.* 345:707-14, 2001.
Zhou et al., "Structural basis for broad and potent neutralization of HIV-1 by antibody VRC01," *Science*, 329:811-817, 2010.

\* cited by examiner

R5-1 = no antibody control;
R5-IC = IC/no Ab;
BD/IC and VS/IC.
All values =1 − sample/IC x 100 = % inhibition

SEQUENCE LISTING

```
<160> NUMBER OF SEQ ID NOS: 8

<210> SEQ ID NO 1
<211> LENGTH: 9377
<212> TYPE: DNA
<213> ORGANISM: Hepatitis GB virus C
<220> FEATURE:
<221> NAME/KEY: CDS
<222> LOCATION: (534)..(9065)

<400> SEQUENCE: 1
cccccccccc ggcactgggt gcaagcccca gaaaccgacg cctactgaag tagacgtaat      60
ggccccgcgc cgaaccggcg accggccaaa aggtggtgga tgggtgatga cagggttggt     120
aggtcgtaaa tcccggtcat cctggtagcc actataggtg ggtcttaagg ggaggctacg     180
gtccctcttg cgcatatgga ggaaaagcgc acggtccaca ggtgttggtc ctaccggtgt     240
aataaggacc cggcgctagg cacgccgtta aaccgagccc gttactcccc tgggcaaacg     300
acgcccacgt acggtccacg tcgccttca atgtctctct tgaccaatag gcgtagccgg      360
cgagttgaca aggaccagtg ggggccgggc gggaggggga aggaccccca ccgctgccct     420
tcccggggag gcgggaaatg catggggcca cccagctccg cggcggccta cagccggggt     480
agcccaagaa ccttcgggtg agggcgggtg gcatttcttt tcctataccg atc atg        536
                                                            Met
                                                              1 gca gtc ctt ctg ctc cta ctc gtg gtg gag gcc ggg gct att tta gcc        584
Ala Val Leu Leu Leu Leu Leu Val Val Glu Ala Gly Ala Ile Leu Ala
           5                  10                  15 ccg gcc acc cat gct tgt agc gcg aaa ggg caa tat tts ctc aca aac        632
Pro Ala Thr His Ala Cys Ser Ala Lys Gly Gln Tyr Xaa Leu Thr Asn
        20                  25                  30 tgt tgc gcc ctg gag gac ata ggc ttc tgc ctg gag ggc gga tgc ctg        680
Cys Cys Ala Leu Glu Asp Ile Gly Phe Cys Leu Glu Gly Gly Cys Leu
```

-continued

| | | |
|---|---|---|
| gtg gct ctg ggg tgc acc att tgc acc gac cgc tgc tgg cca ctg tat<br>Val Ala Leu Gly Cys Thr Ile Cys Thr Asp Arg Cys Trp Pro Leu Tyr<br>50                     55                    60                   65 | 728 |
| cag gcg ggt ttg gcc gtg cgg ccc ggc aag tcc gcc gcc cag ttg gtg<br>Gln Ala Gly Leu Ala Val Arg Pro Gly Lys Ser Ala Ala Gln Leu Val<br>                    70                    75                    80 | 776 |
| ggg gaa ctc ggt agt ctc tac ggg ccc ttg tcg gtc tcg gct tat gtg<br>Gly Glu Leu Gly Ser Leu Tyr Gly Pro Leu Ser Val Ser Ala Tyr Val<br>               85                    90                    95 | 824 |
| gcc ggg atc ctg ggg ctt ggg gag gtc tac tcg ggg gtc ctc acc gtc<br>Ala Gly Ile Leu Gly Leu Gly Glu Val Tyr Ser Gly Val Leu Thr Val<br>                  100                 105                110 | 872 |
| ggg gtg gcg ttg acg cgc agg gtc tac ccg gtc ccg aac ctg acg tgt<br>Gly Val Ala Leu Thr Arg Arg Val Tyr Pro Val Pro Asn Leu Thr Cys<br>115                   120                 125 | 920 |
| gca gta gag tgt gag ttg aag tgg gaa agt gag ttt tgg aga tgg act<br>Ala Val Glu Cys Glu Leu Lys Trp Glu Ser Glu Phe Trp Arg Trp Thr<br>130                   135                 140                145 | 968 |
| gaa cag ctg gcc tca aac tac tgg att ctg gaa tac ctc tgg aag gtg<br>Glu Gln Leu Ala Ser Asn Tyr Trp Ile Leu Glu Tyr Leu Trp Lys Val<br>                  150                 155                160 | 1016 |
| cct ttc gac ttt tgg cgg gga gtg atg agc ctt act cct ctc ttg gtg<br>Pro Phe Asp Phe Trp Arg Gly Val Met Ser Leu Thr Pro Leu Leu Val<br>                   165                 170                175 | 1064 |
| tgc gtg gcg gcc ctc ctc ctg ctg gag cag cgt att gtc atg gtc ttc<br>Cys Val Ala Ala Leu Leu Leu Leu Glu Gln Arg Ile Val Met Val Phe<br>180                   185                 190 | 1112 |
| ctc ctg gtc act atg gcg ggc atg tcg caa ggc gcg ccc gcc tca gtg<br>Leu Leu Val Thr Met Ala Gly Met Ser Gln Gly Ala Pro Ala Ser Val<br>                  195                 200                205 | 1160 |
| ttg ggg tca cgg cct ttc gag gcc ggg ttg act tgg cag tct tgt tct<br>Leu Gly Ser Arg Pro Phe Glu Ala Gly Leu Thr Trp Gln Ser Cys Ser<br>210                   215                 220                225 | 1208 |
| tgc agg tcg aac ggg tcc cgc gtg ccg acg ggg gag agg gtt tgg gaa<br>Cys Arg Ser Asn Gly Ser Arg Val Pro Thr Gly Glu Arg Val Trp Glu<br>                  230                 235                240 | 1256 |
| cgt ggg aac gtc aca ctt ttg tgt gac tgc ccc aac ggt cct tgg gtg<br>Arg Gly Asn Val Thr Leu Leu Cys Asp Cys Pro Asn Gly Pro Trp Val<br>                  245                 250                255 | 1304 |
| tgg gtc ccg gcc ctt tgc cag gca atc gga tgg ggc gac cct atc act<br>Trp Val Pro Ala Leu Cys Gln Ala Ile Gly Trp Gly Asp Pro Ile Thr<br>260                   265                 270 | 1352 |
| cat tgg agc cac gga caa aat cag tgg ccc ctt tct tgt ccc caa ttt<br>His Trp Ser His Gly Gln Asn Gln Trp Pro Leu Ser Cys Pro Gln Phe<br>275                   280                 285 | 1400 |
| gtc tac ggc gcc gtt tca gtg acc tgc gtg tgg ggt tct gtg tct tgg<br>Val Tyr Gly Ala Val Ser Val Thr Cys Val Trp Gly Ser Val Ser Trp<br>290                   295                 300                305 | 1448 |
| ttt gct tcc act ggg ggt cgc gac tcc aag gtt gat gtg tgg agt ttg<br>Phe Ala Ser Thr Gly Gly Arg Asp Ser Lys Val Asp Val Trp Ser Leu<br>                  310                 315                320 | 1496 |
| gtt cca gtt ggc tct gcc agc tgc acc ata gcc gca ctg gga tct tcg<br>Val Pro Val Gly Ser Ala Ser Cys Thr Ile Ala Ala Leu Gly Ser Ser<br>                  325                 330                335 | 1544 |
| gat cgc gac aca gtg gtt gag ctc tcc gag tgg gga att ccc tgc gcc<br>Asp Arg Asp Thr Val Val Glu Leu Ser Glu Trp Gly Ile Pro Cys Ala<br>340                   345                 350 | 1592 |
| act tgt atc ctg gac agg cgg cct gcc tcg tgt ggc acc tgt gtg agg | 1640 |

|     |     |     |     |     |     |     |     |     |     |     |     |     |     |
| --- | --- | --- | --- | --- | --- | --- | --- | --- | --- | --- | --- | --- | --- |
| Thr | Cys | Ile | Leu | Asp | Arg | Arg | Pro | Ala | Ser | Cys | Gly | Thr | Cys | Val | Arg |
|     | 355 |     |     |     | 360 |     |     |     |     | 365 |     |     |     |

```
gac tgc tgg ccc gag acc ggg tcg gta cgt ttc cca ttc cac agg tgt     1688
Asp Cys Trp Pro Glu Thr Gly Ser Val Arg Phe Pro Phe His Arg Cys
370             375                 380                 385 ggc gcg gga ccg agg ctg acc aga gac ctt gag gct gtg ccc ttc gtc     1736
Gly Ala Gly Pro Arg Leu Thr Arg Asp Leu Glu Ala Val Pro Phe Val
                390                 395                 400 aat agg aca act ccc ttc acc ata agg ggg ccc ctg ggc aac cag ggg     1784
Asn Arg Thr Thr Pro Phe Thr Ile Arg Gly Pro Leu Gly Asn Gln Gly
            405                 410                 415 cga ggc aac ccg gtg cgg tcg ccc ttg ggt ttt ggg tcc tac acc atg     1832
Arg Gly Asn Pro Val Arg Ser Pro Leu Gly Phe Gly Ser Tyr Thr Met
        420                 425                 430 acc aag atc cga gac tcc tta cac ttg gtg aaa tgt ccc acc cca gcc     1880
Thr Lys Ile Arg Asp Ser Leu His Leu Val Lys Cys Pro Thr Pro Ala
    435                 440                 445 att gag cct ccc acc gga acg ttt ggg ttc ttc cca gga gtc ccc ccc     1928
Ile Glu Pro Pro Thr Gly Thr Phe Gly Phe Phe Pro Gly Val Pro Pro
450                 455                 460                 465 ctt aac aac tgc atg ctt ctc ggc act gag gtg tca gag gta ttg ggt     1976
Leu Asn Asn Cys Met Leu Leu Gly Thr Glu Val Ser Glu Val Leu Gly
                470                 475                 480 ggg gcg ggc ctc act ggg ggg ttt tac gaa cct ctg gtg cgg cgg tgt     2024
Gly Ala Gly Leu Thr Gly Gly Phe Tyr Glu Pro Leu Val Arg Arg Cys
                485                 490                 495 tca gag ctg atg ggt cgg cgg aat ccg gtc tgc ccg ggg ttt gca tgg     2072
Ser Glu Leu Met Gly Arg Arg Asn Pro Val Cys Pro Gly Phe Ala Trp
            500                 505                 510 ctc tct tcg gga cgg cct gat ggg ttc ata cat gtt cag ggc cac ttg     2120
Leu Ser Ser Gly Arg Pro Asp Gly Phe Ile His Val Gln Gly His Leu
    515                 520                 525 cag gag gtg gat gcg ggc aac ttc att ccg ccc cca cgc tgg ttg ctc     2168
Gln Glu Val Asp Ala Gly Asn Phe Ile Pro Pro Pro Arg Trp Leu Leu
530                 535                 540                 545 ttg gac ttt gta ttt gtc ctg tta tac ctg atg aag ctg gca gag gca     2216
Leu Asp Phe Val Phe Val Leu Leu Tyr Leu Met Lys Leu Ala Glu Ala
                550                 555                 560 cgg ttg gtc ccg ctg atc ctc ctc cta tgg tgg tgg gtg aac cag         2264
Arg Leu Val Pro Leu Ile Leu Leu Leu Trp Trp Trp Val Asn Gln
                565                 570                 575 ttg gcg gtc ctt gkt gtg scg gct gck crc gcc gcc gtg gct gga gag     2312
Leu Ala Val Leu Xaa Val Xaa Ala Ala Xaa Ala Ala Val Ala Gly Glu
            580                 585                 590 gtg ttt gcg ggc cct gcc ttg tcc tgg tgt ctg ggc cta ccc ttc gtg     2360
Val Phe Ala Gly Pro Ala Leu Ser Trp Cys Leu Gly Leu Pro Phe Val
    595                 600                 605 agt atg atc ctg ggg cta gca aac ctg gtg ttg tac ttc cgc tgg atg     2408
Ser Met Ile Leu Gly Leu Ala Asn Leu Val Leu Tyr Phe Arg Trp Met
610                 615                 620                 625 ggt cct caa cgc ctg atg ttc ctc gtg ttg tgg aag ctc gct cgg ggg     2456
Gly Pro Gln Arg Leu Met Phe Leu Val Leu Trp Lys Leu Ala Arg Gly
                630                 635                 640 gct ttc ccg ctg gca tta ctg atg ggg att tcc gcc act cgg ggc cgc     2504
Ala Phe Pro Leu Ala Leu Leu Met Gly Ile Ser Ala Thr Arg Gly Arg
            645                 650                 655 acc tct gtg ctt ggc gcc gaa ttc tgc ttt gat gtc acc ttt gaa gtg     2552
Thr Ser Val Leu Gly Ala Glu Phe Cys Phe Asp Val Thr Phe Glu Val
    660                 665                 670
```

```
gac acg tca gtc ttg ggt tgg gtg gtt gct agt gtg gtg gct tgg gcc    2600
Asp Thr Ser Val Leu Gly Trp Val Val Ala Ser Val Val Ala Trp Ala
            675                 680                 685 ata gcg ctc ctg agc tct atg agc gcg ggg ggg tgg aag cac aaa gcc    2648
Ile Ala Leu Leu Ser Ser Met Ser Ala Gly Gly Trp Lys His Lys Ala
690                 695                 700                 705 ata atc tat agg acg tgg tgt aaa ggg tac cag gcy ctt cgc cag cgc    2696
Ile Ile Tyr Arg Thr Trp Cys Lys Gly Tyr Gln Ala Leu Arg Gln Arg
            710                 715                 720 gtg gtg cgt agc ccc ctc ggg gag ggg cgg ccc acc aag ccg ctg acg    2744
Val Val Arg Ser Pro Leu Gly Glu Gly Arg Pro Thr Lys Pro Leu Thr
                725                 730                 735 ata gcc tgg tgt ctg gcc tct tac atc tgg ccg gac gct gtg atg ttg    2792
Ile Ala Trp Cys Leu Ala Ser Tyr Ile Trp Pro Asp Ala Val Met Leu
            740                 745                 750 gtg gtt gtg gcc atg gtc ctc ctc ttc ggc ctt ttc gac gcg ctc gat    2840
Val Val Val Ala Met Val Leu Leu Phe Gly Leu Phe Asp Ala Leu Asp
755                 760                 765 tgg gcc ttg gag gag ctc ctt gtg tcg cgg cct tcg ttg cgt cgt ttg    2888
Trp Ala Leu Glu Glu Leu Leu Val Ser Arg Pro Ser Leu Arg Arg Leu
770                 775                 780                 785 gca agg gtg gtg gag tgt tgt gtg atg gcg ggc gag aag gcc act acc    2936
Ala Arg Val Val Glu Cys Cys Val Met Ala Gly Glu Lys Ala Thr Thr
            790                 795                 800 gtc cgg ctt gtg tcc aag atg tgc gcg aga ggg gcc tac ctg ttt gac    2984
Val Arg Leu Val Ser Lys Met Cys Ala Arg Gly Ala Tyr Leu Phe Asp
                805                 810                 815 cac atg ggg tcg ttc tcg cgc gcg gtc aag gag cgc ttg ctg gag tgg    3032
His Met Gly Ser Phe Ser Arg Ala Val Lys Glu Arg Leu Leu Glu Trp
            820                 825                 830 gac gcg gct ttg gag mcc ctg tca ttc act agg acg gac tgt cgc atc    3080
Asp Ala Ala Leu Glu Xaa Leu Ser Phe Thr Arg Thr Asp Cys Arg Ile
835                 840                 845 ata cga gac gcc gcc agg acc ctg agc tgc ggc caa tgc gtc atg ggc    3128
Ile Arg Asp Ala Ala Arg Thr Leu Ser Cys Gly Gln Cys Val Met Gly
850                 855                 860                 865 ttg ccc gtg gtg gct agg cgc ggc gat gag gtc ctg att ggg gtc ttt    3176
Leu Pro Val Val Ala Arg Arg Gly Asp Glu Val Leu Ile Gly Val Phe
            870                 875                 880 cag gat gtg aac cac ttg cct ccg ggg ttt gyt cct aca gcg cct gtt    3224
Gln Asp Val Asn His Leu Pro Pro Gly Phe Xaa Pro Thr Ala Pro Val
                885                 890                 895 gtc atc cgt cgg tgc gga aag ggc ttc ctc ggg gtc act aag gct gcc    3272
Val Ile Arg Arg Cys Gly Lys Gly Phe Leu Gly Val Thr Lys Ala Ala
            900                 905                 910 ttg act ggt cgg gat cct gac tta cac cca gga aac gtc atg gtt ttg    3320
Leu Thr Gly Arg Asp Pro Asp Leu His Pro Gly Asn Val Met Val Leu
915                 920                 925 ggg acg gct acc tcg cgc agc atg gga acg tgc tta aac ggg ttg ctg    3368
Gly Thr Ala Thr Ser Arg Ser Met Gly Thr Cys Leu Asn Gly Leu Leu
930                 935                 940                 945 ttc aca aca ttc cat ggg gct tct tcc cga acc att gcg aca cct gtg    3416
Phe Thr Thr Phe His Gly Ala Ser Ser Arg Thr Ile Ala Thr Pro Val
            950                 955                 960 ggg gcc ctt aac cca agg tgg tgg tcg gcc agt gat gac gtc acg gtc    3464
Gly Ala Leu Asn Pro Arg Trp Trp Ser Ala Ser Asp Asp Val Thr Val
                965                 970                 975 tat ccc ctc ccc gat gga gct aac tcg ttg gtt ccc tgc tcg tgt cag    3512
Tyr Pro Leu Pro Asp Gly Ala Asn Ser Leu Val Pro Cys Ser Cys Gln
            980                 985                 990
```

| | | | | | | | | | | | | |
|---|---|---|---|---|---|---|---|---|---|---|---|---|
| gct | gag | tcc | tgt | tgg | gtc | aty | cga | tcc | gat | ggg | gct | ctt tgc cat ggc | 3560 |
| Ala | Glu | Ser | Cys | Trp | Val | Xaa | Arg | Ser | Asp | Gly | Ala | Leu Cys His Gly |
| | | | 995 | | | | 1000 | | | | 1005 | |

```
gct gag tcc tgt tgg gtc aty cga tcc gat ggg gct  ctt tgc cat ggc   3560
Ala Glu Ser Cys Trp Val Xaa Arg Ser Asp Gly Ala  Leu Cys His Gly
            995                 1000                1005 ttg agc aag ggg gac aag gta gaa ctg gac gtg gcc  atg gag gtt       3605
Leu Ser Lys Gly Asp Lys Val Glu Leu Asp Val Ala  Met Glu Val
1010                1015                1020 gct gac ttt cgt ggg tcg tct ggg tct cct gtc cta  tgc gac gag       3650
Ala Asp Phe Arg Gly Ser Ser Gly Ser Pro Val Leu  Cys Asp Glu
1025                1030                1035 ggg cac gct gta gga atg ctc gtg tcc gtc ctt cat  tcg ggg ggg       3695
Gly His Ala Val Gly Met Leu Val Ser Val Leu His  Ser Gly Gly
1040                1045                1050 agg gtg acc gcg gct cga ttc act cgg ccg tgg acc  caa gtc cca       3740
Arg Val Thr Ala Ala Arg Phe Thr Arg Pro Trp Thr  Gln Val Pro
1055                1060                1065 aca gac gcc aag act acc act gag cca ccc ccg gtg  cca gct aaa       3785
Thr Asp Ala Lys Thr Thr Thr Glu Pro Pro Pro Val  Pro Ala Lys
1070                1075                1080 ggg gtt ttc aaa gag gct cct ctt ttc atg cca aca  ggg gcg ggg       3830
Gly Val Phe Lys Glu Ala Pro Leu Phe Met Pro Thr  Gly Ala Gly
1085                1090                1095 aaa agc aca cgc gtc cct ttg gag tat gga aac atg  ggg cac aag       3875
Lys Ser Thr Arg Val Pro Leu Glu Tyr Gly Asn Met  Gly His Lys
1100                1105                1110 gtc ctg att ctc aac ccg tcg gtt gcc act gtg agg  gcc atg ggc       3920
Val Leu Ile Leu Asn Pro Ser Val Ala Thr Val Arg  Ala Met Gly
1115                1120                1125 cct tac atg gag agg ctg gcg ggg aaa cat cct agc  att ttc tgt       3965
Pro Tyr Met Glu Arg Leu Ala Gly Lys His Pro Ser  Ile Phe Cys
1130                1135                1140 gga cac gac aca aca gct ttc aca cgg atc acg gac  tct cca ttg       4010
Gly His Asp Thr Thr Ala Phe Thr Arg Ile Thr Asp  Ser Pro Leu
1145                1150                1155 acg tac tct acc tat ggg agg ttt ctg gcc aac ccg  agg cag atg       4055
Thr Tyr Ser Thr Tyr Gly Arg Phe Leu Ala Asn Pro  Arg Gln Met
1160                1165                1170 ctg agg gga gtt tcc gtg gtc atc tgt gat gag tgc  cac agt cat       4100
Leu Arg Gly Val Ser Val Val Ile Cys Asp Glu Cys  His Ser His
1175                1180                1185 gac tca act gtg ttg ctg ggt ata ggc agg gtc agg  gac gtg gcg       4145
Asp Ser Thr Val Leu Leu Gly Ile Gly Arg Val Arg  Asp Val Ala
1190                1195                1200 cgg ggg tgt gga gtg caa tta gtg ctc tac gct act  gcg act ccc       4190
Arg Gly Cys Gly Val Gln Leu Val Leu Tyr Ala Thr  Ala Thr Pro
1205                1210                1215 ccg ggc tcg cct atg act cag cat cca tcc ata att  gag aca aag       4235
Pro Gly Ser Pro Met Thr Gln His Pro Ser Ile Ile  Glu Thr Lys
1220                1225                1230 ctg gac gtt ggt gag atc ccc ttt tat ggg cat ggt  atc ccc ctc       4280
Leu Asp Val Gly Glu Ile Pro Phe Tyr Gly His Gly  Ile Pro Leu
1235                1240                1245 gag cgt atg agg act ggt cgc cac ctt gta ttc tgc  cat tcc aag       4325
Glu Arg Met Arg Thr Gly Arg His Leu Val Phe Cys  His Ser Lys
1250                1255                1260 gcg gag tgc gag aga ttg gcc ggc cag ttc tcc gcg  cgg ggg gtt       4370
Ala Glu Cys Glu Arg Leu Ala Gly Gln Phe Ser Ala  Arg Gly Val
1265                1270                1275 aat gcc atc gcc tat tat agg ggt aag gac agt tcc  atc atc aaa       4415
Asn Ala Ile Ala Tyr Tyr Arg Gly Lys Asp Ser Ser  Ile Ile Lys
```

```
                1280              1285              1290
gac gga gac ctg gtg gtt tgt gcg aca gac gcg ctc tct acc ggg         4460
Asp Gly Asp Leu Val Val Cys Ala Thr Asp Ala Leu Ser Thr Gly
1295              1300              1305 tac aca gga aac ttc gat tct gtc acc gac tgt ggg ttg gtg gtg         4505
Tyr Thr Gly Asn Phe Asp Ser Val Thr Asp Cys Gly Leu Val Val
1310              1315              1320 gag gag gtc gtt gag gtg acc ctt gat ccc acc att acc att tcc         4550
Glu Glu Val Val Glu Val Thr Leu Asp Pro Thr Ile Thr Ile Ser
1325              1330              1335 ttg cgg act gtc cct gct tcg gct gaa ttg tcg atg cag cgg cgc         4595
Leu Arg Thr Val Pro Ala Ser Ala Glu Leu Ser Met Gln Arg Arg
1340              1345              1350 gga cgc acg ggg aga ggt cgg tcg ggc cgc tac tac tac gct ggg         4640
Gly Arg Thr Gly Arg Gly Arg Ser Gly Arg Tyr Tyr Tyr Ala Gly
1355              1360              1365 gtc ggt aag gct ccc gcg ggg gtg gtg cgg tct ggt ccg gtc tgg         4685
Val Gly Lys Ala Pro Ala Gly Val Val Arg Ser Gly Pro Val Trp
1370              1375              1380 tcg gca gtg gaa gct gga gtg acc tgg tat gga atg gaa cct gac         4730
Ser Ala Val Glu Ala Gly Val Thr Trp Tyr Gly Met Glu Pro Asp
1385              1390              1395 ttg aca gca aac ctt ctg aga ctt tac gac gac tgc cct tac acc         4775
Leu Thr Ala Asn Leu Leu Arg Leu Tyr Asp Asp Cys Pro Tyr Thr
1400              1405              1410 gca gcc gtc gca gct gac att ggt gaa gcc gcg gtg ttc ttt gcg         4820
Ala Ala Val Ala Ala Asp Ile Gly Glu Ala Ala Val Phe Phe Ala
1415              1420              1425 ggc ctc gcg ccc ctc agg atg cat ccc gat gtt agc tgg gca aaa         4865
Gly Leu Ala Pro Leu Arg Met His Pro Asp Val Ser Trp Ala Lys
1430              1435              1440 gtt cgc ggc gtc aat tgg ccc ctc ctg gtg ggt gtt cag cgg acg         4910
Val Arg Gly Val Asn Trp Pro Leu Leu Val Gly Val Gln Arg Thr
1445              1450              1455 atg tgt cgg gaa aca ctg tct ccc ggc ccg tcg gac gac cct cag         4955
Met Cys Arg Glu Thr Leu Ser Pro Gly Pro Ser Asp Asp Pro Gln
1460              1465              1470 tgg gca ggt ctg aaa ggc ccg aat cct gtc cca cta ctg ctg agg         5000
Trp Ala Gly Leu Lys Gly Pro Asn Pro Val Pro Leu Leu Leu Arg
1475              1480              1485 tgg ggc aat gat ttg cca tca aaa gtg gcc ggc cac cac ata gtt         5045
Trp Gly Asn Asp Leu Pro Ser Lys Val Ala Gly His His Ile Val
1490              1495              1500 gac gat ctg gtc cgt cgg ctc ggt gtg gcg gag gga tac gtg cgc         5090
Asp Asp Leu Val Arg Arg Leu Gly Val Ala Glu Gly Tyr Val Arg
1505              1510              1515 tgt gat gct ggr ccc atc ctc atg gtg ggc ttg gcc ata gcg ggc         5135
Cys Asp Ala Xaa Pro Ile Leu Met Val Gly Leu Ala Ile Ala Gly
1520              1525              1530 ggc atg atc tac gcc tct tac act ggg tcg cta gtg gtg gta aca         5180
Gly Met Ile Tyr Ala Ser Tyr Thr Gly Ser Leu Val Val Val Thr
1535              1540              1545 gac tgg gat gtg aag gga ggt ggc aat ccc ctt tat agg agt ggt         5225
Asp Trp Asp Val Lys Gly Gly Gly Asn Pro Leu Tyr Arg Ser Gly
1550              1555              1560 gac cag gcc acc cct caa ccc gtg gtg cag gtc ccc ccg gta gac         5270
Asp Gln Ala Thr Pro Gln Pro Val Val Gln Val Pro Pro Val Asp
1565              1570              1575 cat cgg ccg ggg ggg gag tct gcg cca cgg gat gcc aag aca gtg         5315
```

```
                His Arg Pro Gly Gly Glu Ser Ala Pro Arg Asp Ala Lys Thr Val
                1580            1585                1590 aca gat gcg gtg gca gcc atc cag gtg aac tgc gat tgg tct gtg          5360
Thr Asp Ala Val Ala Ala Ile Gln Val Asn Cys Asp Trp Ser Val
1595            1600                1605 atg acc ctg tcg atc ggg gaa gtc ctc acc ttg gct cag gct aag          5405
Met Thr Leu Ser Ile Gly Glu Val Leu Thr Leu Ala Gln Ala Lys
1610            1615                1620 aca gcc gag gcc tac gca gct act tcc agg tgg ctc gct ggc tgc          5450
Thr Ala Glu Ala Tyr Ala Ala Thr Ser Arg Trp Leu Ala Gly Cys
1625            1630                1635 tac acg ggg acg cgg gcc gtc ccc act gta tca att gtt gac aag          5495
Tyr Thr Gly Thr Arg Ala Val Pro Thr Val Ser Ile Val Asp Lys
1640            1645                1650 ctc ttc gcc ggg ggt tgg gcc gcc gtg gtg ggt cac tgt cac agc          5540
Leu Phe Ala Gly Gly Trp Ala Ala Val Val Gly His Cys His Ser
1655            1660                1665 gtc att gct gcg gcg gtg gct gcc tat gga gct tct cga agt cct          5585
Val Ile Ala Ala Ala Val Ala Ala Tyr Gly Ala Ser Arg Ser Pro
1670            1675                1680 cca ctg gcc gcg gcg gcg tcc tac ctc atg ggg ttg ggc gtc gga          5630
Pro Leu Ala Ala Ala Ala Ser Tyr Leu Met Gly Leu Gly Val Gly
1685            1690                1695 ggc aac gca cag gcg cgc ttg gct tca gct ctt cta ctg ggg gct          5675
Gly Asn Ala Gln Ala Arg Leu Ala Ser Ala Leu Leu Leu Gly Ala
1700            1705                1710 gct ggt acg gct ctg ggg acc cct gtc gtg gga ctc acc atg gcg          5720
Ala Gly Thr Ala Leu Gly Thr Pro Val Val Gly Leu Thr Met Ala
1715            1720                1725 ggg gcc ttc atg ggc ggt gcc agc gtg tcc ccc tcc ctc gtc act          5765
Gly Ala Phe Met Gly Gly Ala Ser Val Ser Pro Ser Leu Val Thr
1730            1735                1740 gtc cta ctt ggg gct gtg gga ggt tgg gag ggc gtt gtc aac gct          5810
Val Leu Leu Gly Ala Val Gly Gly Trp Glu Gly Val Val Asn Ala
1745            1750                1755 gcc agt ctc gtc ttc gac ttc atg gct ggg aaa ctt tca aca gaa          5855
Ala Ser Leu Val Phe Asp Phe Met Ala Gly Lys Leu Ser Thr Glu
1760            1765                1770 gac ctt tgg tat gcc atc ccg gta ctc act agt cct ggr gcg ggc          5900
Asp Leu Trp Tyr Ala Ile Pro Val Leu Thr Ser Pro Xaa Ala Gly
1775            1780                1785 ctc gcg ggg att gcc ctt ggt ctg gtt ttg tac tca gca aac aac          5945
Leu Ala Gly Ile Ala Leu Gly Leu Val Leu Tyr Ser Ala Asn Asn
1790            1795                1800 tct ggc act acc aca tgg ctg aac cgt ctg ctg acg acg ttg cca          5990
Ser Gly Thr Thr Thr Trp Leu Asn Arg Leu Leu Thr Thr Leu Pro
1805            1810                1815 cgg tca tct tgc ata ccc gac agc tac ttc caa cag gct gac tac          6035
Arg Ser Ser Cys Ile Pro Asp Ser Tyr Phe Gln Gln Ala Asp Tyr
1820            1825                1830 tgc gac aag gtc tcg gca atc gtg cgc cgc ctg agc ctt act cgc          6080
Cys Asp Lys Val Ser Ala Ile Val Arg Arg Leu Ser Leu Thr Arg
1835            1840                1845 acc gtg gtg gcc ctg gtc aac agg gag cct aag gtg gat gag gtc          6125
Thr Val Val Ala Leu Val Asn Arg Glu Pro Lys Val Asp Glu Val
1850            1855                1860 cag gtg ggg tac gtc tgg gat ctg tgg gag tgg gtg atg cgc cag          6170
Gln Val Gly Tyr Val Trp Asp Leu Trp Glu Trp Val Met Arg Gln
1865            1870                1875
```

```
gtg cgc atg gtg atg tct aga ctc cgg gcc ctc tgc cct gtg gtg    6215
Val Arg Met Val Met Ser Arg Leu Arg Ala Leu Cys Pro Val Val
1880                1885                1890 tca ctc ccc ttg tgg cac tgc ggg gag ggg tgg tcc ggt gaa tgg    6260
Ser Leu Pro Leu Trp His Cys Gly Glu Gly Trp Ser Gly Glu Trp
1895                1900                1905 ctt ctc gat ggg cac gtg gag agt cgt tgt ctg tgc ggg tgt gta    6305
Leu Leu Asp Gly His Val Glu Ser Arg Cys Leu Cys Gly Cys Val
1910                1915                1920 atc acc ggc gac gtc ctc aat ggg caa ctc aaa gat cca gtt tac    6350
Ile Thr Gly Asp Val Leu Asn Gly Gln Leu Lys Asp Pro Val Tyr
1925                1930                1935 tct acc aag ctg tgc agg cac tac tgg atg gga act gtg ccg gtc    6395
Ser Thr Lys Leu Cys Arg His Tyr Trp Met Gly Thr Val Pro Val
1940                1945                1950 aac atg ctg ggc tac ggg gaa acc tca cct ctt ctc gcc tct gac    6440
Asn Met Leu Gly Tyr Gly Glu Thr Ser Pro Leu Leu Ala Ser Asp
1955                1960                1965 acc ccg aag gtg gta ccc ttc ggg acg tcg ggg tgg gct gag gtg    6485
Thr Pro Lys Val Val Pro Phe Gly Thr Ser Gly Trp Ala Glu Val
1970                1975                1980 gtg gtg acc cct acc cac gtg gtg atc agg cgc acg tcc tgt tac    6530
Val Val Thr Pro Thr His Val Val Ile Arg Arg Thr Ser Cys Tyr
1985                1990                1995 aaa ctg ctt cgc cag caa att ctt tca gca gct gta gct gag ccc    6575
Lys Leu Leu Arg Gln Gln Ile Leu Ser Ala Ala Val Ala Glu Pro
2000                2005                2010 tac tac gtt gat ggc att ccg gtc tct tgg gag gct gac gcg aga    6620
Tyr Tyr Val Asp Gly Ile Pro Val Ser Trp Glu Ala Asp Ala Arg
2015                2020                2025 gcg ccg gcc atg gtc tac ggt ccg ggc caa agt gtt acc att gat    6665
Ala Pro Ala Met Val Tyr Gly Pro Gly Gln Ser Val Thr Ile Asp
2030                2035                2040 ggg gag cgc tac acc ctt ccg cac cag ttg cgg atg cgg aat gtg    6710
Gly Glu Arg Tyr Thr Leu Pro His Gln Leu Arg Met Arg Asn Val
2045                2050                2055 gcg ccc tct gag gtt tca tct gag gtc agc atc gag atc ggg acg    6755
Ala Pro Ser Glu Val Ser Ser Glu Val Ser Ile Glu Ile Gly Thr
2060                2065                2070 gag act gaa gac tca gaa ctg act gag gcc gat ttg cca cca gcg    6800
Glu Thr Glu Asp Ser Glu Leu Thr Glu Ala Asp Leu Pro Pro Ala
2075                2080                2085 gct gct gcc ctc caa gcg ata gag aat gct gcg aga att ctc gaa    6845
Ala Ala Ala Leu Gln Ala Ile Glu Asn Ala Ala Arg Ile Leu Glu
2090                2095                2100 ccg cac atc gat gtc ayc atg gag gat tgc agt aca ccc tct ctc    6890
Pro His Ile Asp Val Xaa Met Glu Asp Cys Ser Thr Pro Ser Leu
2105                2110                2115 tgt ggt agt agc cga gag atg cct gtg tgg gga gaa gac ata ccc    6935
Cys Gly Ser Ser Arg Glu Met Pro Val Trp Gly Glu Asp Ile Pro
2120                2125                2130 cgc act cca tcg cct gca ctt atc tcg gtt acg gag agc agc tca    6980
Arg Thr Pro Ser Pro Ala Leu Ile Ser Val Thr Glu Ser Ser Ser
2135                2140                2145 gat gag aag acc ctg tcg gtg acc tcc tcg cag gag gac acc ccg    7025
Asp Glu Lys Thr Leu Ser Val Thr Ser Ser Gln Glu Asp Thr Pro
2150                2155                2160 tcc tca gac tca ttt gaa gtc atc caa gag tct gat act gct gaa    7070
Ser Ser Asp Ser Phe Glu Val Ile Gln Glu Ser Asp Thr Ala Glu
2165                2170                2175
```

| | | | | | | | | | | |
|---|---|---|---|---|---|---|---|---|---|---|
| tca | gag | gaa | agc | gtc | ttc | aac | gtg | gct | ctt | tcc | gta | cta | aaa | gcc | 7115 |
| Ser | Glu | Glu | Ser | Val | Phe | Asn | Val | Ala | Leu | Ser | Val | Leu | Lys | Ala | |
| 2180 | | | | 2185 | | | | | 2190 | | | | | | |

| tta | ttt | cca | cag | agc | gat | gcc | aca | cga | aag | cta | acg | gtt | aag | atg | 7160 |
| Leu | Phe | Pro | Gln | Ser | Asp | Ala | Thr | Arg | Lys | Leu | Thr | Val | Lys | Met | |
| 2195 | | | | 2200 | | | | | 2205 | | | | | | |

| tct | tgc | tgt | gtt | gag | aag | agc | gta | aca | cgc | ttc | ttt | tct | tta | ggg | 7205 |
| Ser | Cys | Cys | Val | Glu | Lys | Ser | Val | Thr | Arg | Phe | Phe | Ser | Leu | Gly | |
| 2210 | | | | 2215 | | | | | 2220 | | | | | | |

| ttg | acc | gtg | gct | gac | gtg | gct | agc | ctg | tgt | gag | atg | gag | atc | cag | 7250 |
| Leu | Thr | Val | Ala | Asp | Val | Ala | Ser | Leu | Cys | Glu | Met | Glu | Ile | Gln | |
| 2225 | | | | 2230 | | | | | 2235 | | | | | | |

| aac | cat | aca | gcc | tat | tgt | gac | aag | gtg | cgc | act | ccg | ctc | gaa | ttg | 7295 |
| Asn | His | Thr | Ala | Tyr | Cys | Asp | Lys | Val | Arg | Thr | Pro | Leu | Glu | Leu | |
| 2240 | | | | 2245 | | | | | 2250 | | | | | | |

| caa | gtt | ggg | tgc | ttg | gtg | ggc | aat | gaa | ctt | acc | ttt | gaa | tgt | gac | 7340 |
| Gln | Val | Gly | Cys | Leu | Val | Gly | Asn | Glu | Leu | Thr | Phe | Glu | Cys | Asp | |
| 2255 | | | | 2260 | | | | | 2265 | | | | | | |

| aag | tgt | gag | gca | cgc | caa | gag | acc | ctt | gcc | tcc | ttc | tcc | tac | ata | 7385 |
| Lys | Cys | Glu | Ala | Arg | Gln | Glu | Thr | Leu | Ala | Ser | Phe | Ser | Tyr | Ile | |
| 2270 | | | | 2275 | | | | | 2280 | | | | | | |

| tgg | tcc | ggg | gtc | cca | ctt | act | cgg | gcc | act | ccg | gcc | aaa | cca | cca | 7430 |
| Trp | Ser | Gly | Val | Pro | Leu | Thr | Arg | Ala | Thr | Pro | Ala | Lys | Pro | Pro | |
| 2285 | | | | 2290 | | | | | 2295 | | | | | | |

| gtg | gtg | agg | ccg | gtg | ggg | tcc | ttg | ttg | gtg | gca | gac | acc | acc | aag | 7475 |
| Val | Val | Arg | Pro | Val | Gly | Ser | Leu | Leu | Val | Ala | Asp | Thr | Thr | Lys | |
| 2300 | | | | 2305 | | | | | 2310 | | | | | | |

| gtc | tac | gtg | acc | aat | ccg | gac | aat | gtt | ggg | agg | agg | gtt | gac | aag | 7520 |
| Val | Tyr | Val | Thr | Asn | Pro | Asp | Asn | Val | Gly | Arg | Arg | Val | Asp | Lys | |
| 2315 | | | | 2320 | | | | | 2325 | | | | | | |

| gtg | act | ttc | tgg | cgc | gct | cct | cgg | gta | cac | gac | aag | ttc | ctc | gtg | 7565 |
| Val | Thr | Phe | Trp | Arg | Ala | Pro | Arg | Val | His | Asp | Lys | Phe | Leu | Val | |
| 2330 | | | | 2335 | | | | | 2340 | | | | | | |

| gac | tcg | atc | gag | cgc | gct | cgg | aga | gct | gct | caa | ggc | tgc | cta | agc | 7610 |
| Asp | Ser | Ile | Glu | Arg | Ala | Arg | Arg | Ala | Ala | Gln | Gly | Cys | Leu | Ser | |
| 2345 | | | | 2350 | | | | | 2355 | | | | | | |

| atg | ggt | tac | act | tat | gag | gag | gca | ata | agg | act | gtt | agg | ccg | cat | 7655 |
| Met | Gly | Tyr | Thr | Tyr | Glu | Glu | Ala | Ile | Arg | Thr | Val | Arg | Pro | His | |
| 2360 | | | | 2365 | | | | | 2370 | | | | | | |

| gct | gcc | atg | ggc | tgg | gga | tct | aag | gtg | tcg | gtc | aag | gac | ttg | gcc | 7700 |
| Ala | Ala | Met | Gly | Trp | Gly | Ser | Lys | Val | Ser | Val | Lys | Asp | Leu | Ala | |
| 2375 | | | | 2380 | | | | | 2385 | | | | | | |

| acc | cct | gcg | ggg | aag | atg | gct | gtt | cat | gac | cgg | ctt | cag | gag | ata | 7745 |
| Thr | Pro | Ala | Gly | Lys | Met | Ala | Val | His | Asp | Arg | Leu | Gln | Glu | Ile | |
| 2390 | | | | 2395 | | | | | 2400 | | | | | | |

| ctt | gaa | ggg | act | ccg | gtc | cct | ttt | acc | ctg | act | gtc | aaa | aag | gag | 7790 |
| Leu | Glu | Gly | Thr | Pro | Val | Pro | Phe | Thr | Leu | Thr | Val | Lys | Lys | Glu | |
| 2405 | | | | 2410 | | | | | 2415 | | | | | | |

| gtg | ttc | ttc | aaa | gat | cgt | aag | gag | gag | aag | gcc | ccc | cgc | ctc | att | 7835 |
| Val | Phe | Phe | Lys | Asp | Arg | Lys | Glu | Glu | Lys | Ala | Pro | Arg | Leu | Ile | |
| 2420 | | | | 2425 | | | | | 2430 | | | | | | |

| gtg | ttc | ccc | ccc | ctg | gac | ttc | cgg | ata | gct | gaa | aag | ctc | att | ctg | 7880 |
| Val | Phe | Pro | Pro | Leu | Asp | Phe | Arg | Ile | Ala | Glu | Lys | Leu | Ile | Leu | |
| 2435 | | | | 2440 | | | | | 2445 | | | | | | |

| gga | gac | ccg | ggg | cgg | gtt | gca | aag | gcc | ggt | gtt | ggg | ggg | gct | tac | 7925 |
| Gly | Asp | Pro | Gly | Arg | Val | Ala | Lys | Ala | Gly | Val | Gly | Gly | Ala | Tyr | |
| 2450 | | | | 2455 | | | | | 2460 | | | | | | |

| gcc | ttc | cag | tac | acc | ccc | aac | cag | cgg | gtt | aag | gag | atg | cta | aag | 7970 |
| Ala | Phe | Gln | Tyr | Thr | Pro | Asn | Gln | Arg | Val | Lys | Glu | Met | Leu | Lys | |

|  |  |  |  |  | 2465 |  |  |  | 2470 |  |  |  | 2475 |  |  |  |
|---|---|---|---|---|---|---|---|---|---|---|---|---|---|---|---|---|
| ctg | tgg | gaa | tca | aag | aag | acc | ccg | tgc | gcc | atc | tgt | gtg | gat | gcc |  | 8015 |
| Leu | Trp | Glu | Ser | Lys | Lys | Thr | Pro | Cys | Ala | Ile | Cys | Val | Asp | Ala |  |  |
| 2480 |  |  |  |  | 2485 |  |  |  | 2490 |  |  |  |  |  |  |  |
| act | tgc | ttc | gac | agt | agc | att | act | gar | gag | gac | gtg | gca | cta | gag |  | 8060 |
| Thr | Cys | Phe | Asp | Ser | Ser | Ile | Thr | Glu | Glu | Asp | Val | Ala | Leu | Glu |  |  |
| 2495 |  |  |  | 2500 |  |  |  |  | 2505 |  |  |  |  |  |  |  |
| aca | gag | ctt | tac | gcc | ctg | gcc | tcg | gac | cat | cca | gaa | tgg | gtg | cgc |  | 8105 |
| Thr | Glu | Leu | Tyr | Ala | Leu | Ala | Ser | Asp | His | Pro | Glu | Trp | Val | Arg |  |  |
| 2510 |  |  |  |  | 2515 |  |  |  | 2520 |  |  |  |  |  |  |  |
| gcc | ctg | ggg | aaa | tac | trt | gcc | tct | ggc | aca | atg | gtg | acc | ccg | gaa |  | 8150 |
| Ala | Leu | Gly | Lys | Tyr | Xaa | Ala | Ser | Gly | Thr | Met | Val | Thr | Pro | Glu |  |  |
| 2525 |  |  |  |  | 2530 |  |  |  | 2535 |  |  |  |  |  |  |  |
| ggg | gtg | cca | gtg | ggc | gag | agg | tat | tgt | agg | tcc | tcg | ggt | gtg | ttg |  | 8195 |
| Gly | Val | Pro | Val | Gly | Glu | Arg | Tyr | Cys | Arg | Ser | Ser | Gly | Val | Leu |  |  |
| 2540 |  |  |  |  | 2545 |  |  |  | 2550 |  |  |  |  |  |  |  |
| acc | aca | agt | gct | agc | aac | tgt | ttg | acc | tgc | tac | atc | aaa | gtg | aga |  | 8240 |
| Thr | Thr | Ser | Ala | Ser | Asn | Cys | Leu | Thr | Cys | Tyr | Ile | Lys | Val | Arg |  |  |
| 2555 |  |  |  |  | 2560 |  |  |  | 2565 |  |  |  |  |  |  |  |
| gcc | gcc | tgt | gag | agg | atc | gga | ctg | aaa | aat | gtc | tcg | ctt | ctc | atc |  | 8285 |
| Ala | Ala | Cys | Glu | Arg | Ile | Gly | Leu | Lys | Asn | Val | Ser | Leu | Leu | Ile |  |  |
| 2570 |  |  |  |  | 2575 |  |  |  | 2580 |  |  |  |  |  |  |  |
| gcg | ggc | gat | gac | tgc | tta | att | gtg | tgc | gag | agg | cct | gta | tgc | gac |  | 8330 |
| Ala | Gly | Asp | Asp | Cys | Leu | Ile | Val | Cys | Glu | Arg | Pro | Val | Cys | Asp |  |  |
| 2585 |  |  |  |  | 2590 |  |  |  | 2595 |  |  |  |  |  |  |  |
| cct | tgc | gag | gcc | ctg | ggc | cga | acc | ctg | gct | tcg | tac | ggg | tac | gcg |  | 8375 |
| Pro | Cys | Glu | Ala | Leu | Gly | Arg | Thr | Leu | Ala | Ser | Tyr | Gly | Tyr | Ala |  |  |
| 2600 |  |  |  |  | 2605 |  |  |  | 2610 |  |  |  |  |  |  |  |
| tgt | gag | ccc | tcg | tat | cac | gct | tca | ctg | gac | aca | gcc | ccc | ttc | tgc |  | 8420 |
| Cys | Glu | Pro | Ser | Tyr | His | Ala | Ser | Leu | Asp | Thr | Ala | Pro | Phe | Cys |  |  |
| 2615 |  |  |  |  | 2620 |  |  |  | 2625 |  |  |  |  |  |  |  |
| tcc | act | tgg | ctc | gct | gag | tgc | aat | gcg | gat | ggg | raa | agg | cat | ttc |  | 8465 |
| Ser | Thr | Trp | Leu | Ala | Glu | Cys | Asn | Ala | Asp | Gly | Xaa | Arg | His | Phe |  |  |
| 2630 |  |  |  |  | 2635 |  |  |  | 2640 |  |  |  |  |  |  |  |
| ttc | ctg | acc | acg | gac | ttt | cgg | aga | cca | ctc | gct | cgc | atg | tcg | agc |  | 8510 |
| Phe | Leu | Thr | Thr | Asp | Phe | Arg | Arg | Pro | Leu | Ala | Arg | Met | Ser | Ser |  |  |
| 2645 |  |  |  |  | 2650 |  |  |  | 2655 |  |  |  |  |  |  |  |
| gag | tac | agt | gac | cct | atg | gct | tcg | gcc | att | ggt | tac | att | ctc | ctc |  | 8555 |
| Glu | Tyr | Ser | Asp | Pro | Met | Ala | Ser | Ala | Ile | Gly | Tyr | Ile | Leu | Leu |  |  |
| 2660 |  |  |  |  | 2665 |  |  |  | 2670 |  |  |  |  |  |  |  |
| tac | ccc | tgg | crt | ccc | atc | aca | cgg | tgg | gtc | atc | atc | ccg | cat | gtg |  | 8600 |
| Tyr | Pro | Trp | Xaa | Pro | Ile | Thr | Arg | Trp | Val | Ile | Ile | Pro | His | Val |  |  |
| 2675 |  |  |  |  | 2680 |  |  |  | 2685 |  |  |  |  |  |  |  |
| cta | aca | tgc | gct | tct | tcc | cgg | ggt | ggt | ggc | aca | csg | tct | gat | ccg |  | 8645 |
| Leu | Thr | Cys | Ala | Ser | Ser | Arg | Gly | Gly | Gly | Thr | Xaa | Ser | Asp | Pro |  |  |
| 2690 |  |  |  |  | 2695 |  |  |  | 2700 |  |  |  |  |  |  |  |
| gtt | tgg | tgt | cag | gtt | cat | ggt | aac | tac | tac | aag | ttt | ccc | ctg | gac |  | 8690 |
| Val | Trp | Cys | Gln | Val | His | Gly | Asn | Tyr | Tyr | Lys | Phe | Pro | Leu | Asp |  |  |
| 2705 |  |  |  |  | 2710 |  |  |  | 2715 |  |  |  |  |  |  |  |
| aaa | ctg | cct | aac | atc | atc | gtg | gcc | ctc | cac | gga | cca | gca | gcg | ttg |  | 8735 |
| Lys | Leu | Pro | Asn | Ile | Ile | Val | Ala | Leu | His | Gly | Pro | Ala | Ala | Leu |  |  |
| 2720 |  |  |  |  | 2725 |  |  |  | 2730 |  |  |  |  |  |  |  |
| agg | gtt | acc | gca | gac | aca | acc | aaa | aca | aag | atg | gag | gct | ggg | aag |  | 8780 |
| Arg | Val | Thr | Ala | Asp | Thr | Thr | Lys | Thr | Lys | Met | Glu | Ala | Gly | Lys |  |  |
| 2735 |  |  |  |  | 2740 |  |  |  | 2745 |  |  |  |  |  |  |  |
| gtt | ctg | agc | gac | ctc | aag | ctc | cct | ggt | cta | gcc | gtc | cac | cgc | aag |  | 8825 |
| Val | Leu | Ser | Asp | Leu | Lys | Leu | Pro | Gly | Leu | Ala | Val | His | Arg | Lys |  |  |
| 2750 |  |  |  |  | 2755 |  |  |  | 2760 |  |  |  |  |  |  |  |
| aag | gcc | ggg | gca | ttg | cga | aca | cgc | atg | ctc | cgg | tcg | cgc | ggt | tgg |  | 8870 |

-continued

```
Lys Ala Gly Ala Leu Arg Thr Arg Met Leu Arg Ser Arg Gly Trp
2765                2770                2775 gcg gag ttg gct agg ggc ctg ttg tgg cat cca gga ctc cgg ctt       8915
Ala Glu Leu Ala Arg Gly Leu Leu Trp His Pro Gly Leu Arg Leu
2780                2785                2790 cct ccc cct gag att gct ggt atc cca ggg ggt ttc cct ctg tcc       8960
Pro Pro Pro Glu Ile Ala Gly Ile Pro Gly Gly Phe Pro Leu Ser
2795                2800                2805 ccc ccc tac atg ggg gtg gtt cat caa ttg gat ttc aca gcs cag       9005
Pro Pro Tyr Met Gly Val Val His Gln Leu Asp Phe Thr Ala Gln
2810                2815                2820 cgg agt cgc tgg cgg tgg ttg ggg ttc tta gcc ctg ctc atc gta       9050
Arg Ser Arg Trp Arg Trp Leu Gly Phe Leu Ala Leu Leu Ile Val
2825                2830                2835 gcg ctc ttt ggg tga actaaattca tctgttgcgg caaggttgag cggctgatca   9105
Ala Leu Phe Gly
2840 ccgctcaagg aggttcccgc cctccccgcc ccaggggtct ccccgctggg taaaaagggc  9165 ccggccttgg gaggcatggt ggttactaac ccctggcag ggttaacgcc tgatggtgct   9225 aatgcactgc cgcttcggcg gcgggtcgct accttatagc gtaatccgtg actacgggct  9285 gctcgcagag ccctccccgg atggggcaca gtgcactgtg atctgaaggg gtgcaccccg  9345 gtaagagctc ggcccaaagg ccgggttcta ct                                9377
```

<210> SEQ ID NO 2
<211> LENGTH: 2843
<212> TYPE: PRT
<213> ORGANISM: Hepatitis GB virus C
<220> FEATURE:
<221> NAME/KEY: misc_feature
<222> LOCATION: (30)..(30)
<223> OTHER INFORMATION: The 'Xaa' at location 30 stands for Leu, or Phe.
<220> FEATURE:
<221> NAME/KEY: misc_feature
<222> LOCATION: (582)..(582)
<223> OTHER INFORMATION: The 'Xaa' at location 582 stands for Gly, or Val.
<220> FEATURE:
<221> NAME/KEY: misc_feature
<222> LOCATION: (584)..(584)
<223> OTHER INFORMATION: The 'Xaa' at location 584 stands for Ala, or Pro.
<220> FEATURE:
<221> NAME/KEY: misc_feature
<222> LOCATION: (587)..(587)
<223> OTHER INFORMATION: The 'Xaa' at location 587 stands for Arg, or His.
<220> FEATURE:
<221> NAME/KEY: misc_feature
<222> LOCATION: (839)..(839)
<223> OTHER INFORMATION: The 'Xaa' at location 839 stands for Thr, or Pro.
<220> FEATURE:
<221> NAME/KEY: misc_feature
<222> LOCATION: (892)..(892)
<223> OTHER INFORMATION: The 'Xaa' at location 892 stands for Ala, or Val.
<220> FEATURE:
<221> NAME/KEY: misc_feature
<222> LOCATION: (1000)..(1000)
<223> OTHER INFORMATION: The 'Xaa' at location 1000 stands for Ile.
<220> FEATURE:
<221> NAME/KEY: misc_feature
<222> LOCATION: (1523)..(1523)
<223> OTHER INFORMATION: The 'Xaa' at location 1523 stands for Gly.
<220> FEATURE:
<221> NAME/KEY: misc_feature
<222> LOCATION: (1787)..(1787)

-continued

```
<223> OTHER INFORMATION: The 'Xaa' at location 1787 stands for Gly.
<220> FEATURE:
<221> NAME/KEY: misc_feature
<222> LOCATION: (2110)..(2110)
<223> OTHER INFORMATION: The 'Xaa' at location 2110 stands for Thr, or
      Ile.
<220> FEATURE:
<221> NAME/KEY: misc_feature
<222> LOCATION: (2530)..(2530)
<223> OTHER INFORMATION: The 'Xaa' at location 2530 stands for Cys, or
      Tyr.
<220> FEATURE:
<221> NAME/KEY: misc_feature
<222> LOCATION: (2641)..(2641)
<223> OTHER INFORMATION: The 'Xaa' at location 2641 stands for Glu, or
      Lys.
<220> FEATURE:
<221> NAME/KEY: misc_feature
<222> LOCATION: (2678)..(2678)
<223> OTHER INFORMATION: The 'Xaa' at location 2678 stands for Arg, or
      His.
<220> FEATURE:
<221> NAME/KEY: misc_feature
<222> LOCATION: (2701)..(2701)
<223> OTHER INFORMATION: The 'Xaa' at location 2701 stands for Arg, or
      Pro.

<400> SEQUENCE: 2

Met Ala Val Leu Leu Leu Leu Val Val Glu Ala Gly Ala Ile Leu
1               5                   10                  15

Ala Pro Ala Thr His Ala Cys Ser Ala Lys Gly Gln Tyr Xaa Leu Thr
            20                  25                  30

Asn Cys Cys Ala Leu Glu Asp Ile Gly Phe Cys Leu Glu Gly Gly Cys
        35                  40                  45

Leu Val Ala Leu Gly Cys Thr Ile Cys Thr Asp Arg Cys Trp Pro Leu
    50                  55                  60

Tyr Gln Ala Gly Leu Ala Val Arg Pro Gly Lys Ser Ala Ala Gln Leu
65              70                  75                  80

Val Gly Glu Leu Gly Ser Leu Tyr Gly Pro Leu Ser Val Ser Ala Tyr
                85                  90                  95

Val Ala Gly Ile Leu Gly Leu Gly Glu Val Tyr Ser Gly Val Leu Thr
            100                 105                 110

Val Gly Val Ala Leu Thr Arg Arg Val Tyr Pro Val Pro Asn Leu Thr
        115                 120                 125

Cys Ala Val Glu Cys Glu Leu Lys Trp Glu Ser Glu Phe Trp Arg Trp
    130                 135                 140

Thr Glu Gln Leu Ala Ser Asn Tyr Trp Ile Leu Glu Tyr Leu Trp Lys
145                 150                 155                 160

Val Pro Phe Asp Phe Trp Arg Gly Val Met Ser Leu Thr Pro Leu Leu
                165                 170                 175

Val Cys Val Ala Ala Leu Leu Leu Glu Gln Arg Ile Val Met Val
            180                 185                 190

Phe Leu Leu Val Thr Met Ala Gly Met Ser Gln Gly Ala Pro Ala Ser
            195                 200                 205

Val Leu Gly Ser Arg Pro Phe Glu Ala Gly Leu Thr Trp Gln Ser Cys
        210                 215                 220

Ser Cys Arg Ser Asn Gly Ser Arg Val Pro Thr Gly Glu Arg Val Trp
225                 230                 235                 240

Glu Arg Gly Asn Val Thr Leu Leu Cys Asp Cys Pro Asn Gly Pro Trp
                245                 250                 255

Val Trp Val Pro Ala Leu Cys Gln Ala Ile Gly Trp Gly Asp Pro Ile
            260                 265                 270
```

-continued

```
Thr His Trp Ser His Gly Gln Asn Gln Trp Pro Leu Ser Cys Pro Gln
        275                 280                 285

Phe Val Tyr Gly Ala Val Ser Val Thr Cys Val Trp Gly Ser Val Ser
    290                 295                 300

Trp Phe Ala Ser Thr Gly Gly Arg Asp Ser Lys Val Asp Val Trp Ser
305                 310                 315                 320

Leu Val Pro Val Gly Ser Ala Ser Cys Thr Ile Ala Ala Leu Gly Ser
                325                 330                 335

Ser Asp Arg Asp Thr Val Val Glu Leu Ser Glu Trp Gly Ile Pro Cys
            340                 345                 350

Ala Thr Cys Ile Leu Asp Arg Arg Pro Ala Ser Cys Gly Thr Cys Val
        355                 360                 365

Arg Asp Cys Trp Pro Glu Thr Gly Ser Val Arg Phe Pro Phe His Arg
    370                 375                 380

Cys Gly Ala Gly Pro Arg Leu Thr Arg Asp Leu Glu Ala Val Pro Phe
385                 390                 395                 400

Val Asn Arg Thr Thr Pro Phe Thr Ile Arg Gly Pro Leu Gly Asn Gln
                405                 410                 415

Gly Arg Gly Asn Pro Val Arg Ser Pro Leu Gly Phe Gly Ser Tyr Thr
            420                 425                 430

Met Thr Lys Ile Arg Asp Ser Leu His Leu Val Lys Cys Pro Thr Pro
        435                 440                 445

Ala Ile Glu Pro Pro Thr Gly Thr Phe Gly Phe Pro Gly Val Pro
    450                 455                 460

Pro Leu Asn Asn Cys Met Leu Leu Gly Thr Glu Val Ser Glu Val Leu
465                 470                 475                 480

Gly Gly Ala Gly Leu Thr Gly Gly Phe Tyr Glu Pro Leu Val Arg Arg
                485                 490                 495

Cys Ser Glu Leu Met Gly Arg Arg Asn Pro Val Cys Pro Gly Phe Ala
            500                 505                 510

Trp Leu Ser Ser Gly Arg Pro Asp Gly Phe Ile His Val Gln Gly His
        515                 520                 525

Leu Gln Glu Val Asp Ala Gly Asn Phe Ile Pro Pro Arg Trp Leu
    530                 535                 540

Leu Leu Asp Phe Val Phe Val Leu Leu Tyr Leu Met Lys Leu Ala Glu
545                 550                 555                 560

Ala Arg Leu Val Pro Leu Ile Leu Leu Leu Trp Trp Trp Val Asn
                565                 570                 575

Gln Leu Ala Val Leu Xaa Val Xaa Ala Ala Xaa Ala Ala Val Ala Gly
            580                 585                 590

Glu Val Phe Ala Gly Pro Ala Leu Ser Trp Cys Leu Gly Leu Pro Phe
        595                 600                 605

Val Ser Met Ile Leu Gly Leu Ala Asn Leu Val Leu Tyr Phe Arg Trp
    610                 615                 620

Met Gly Pro Gln Arg Leu Met Phe Leu Val Leu Trp Lys Leu Ala Arg
625                 630                 635                 640

Gly Ala Phe Pro Leu Ala Leu Leu Met Gly Ile Ser Ala Thr Arg Gly
                645                 650                 655

Arg Thr Ser Val Leu Gly Ala Glu Phe Cys Phe Asp Val Thr Phe Glu
            660                 665                 670

Val Asp Thr Ser Val Leu Gly Trp Val Val Ala Ser Val Ala Trp
        675                 680                 685
```

-continued

Ala Ile Ala Leu Leu Ser Ser Met Ser Ala Gly Gly Trp Lys His Lys
690                 695                 700

Ala Ile Ile Tyr Arg Thr Trp Cys Lys Gly Tyr Gln Ala Leu Arg Gln
705                 710                 715                 720

Arg Val Val Arg Ser Pro Leu Gly Glu Gly Arg Pro Thr Lys Pro Leu
            725                 730                 735

Thr Ile Ala Trp Cys Leu Ala Ser Tyr Ile Trp Pro Asp Ala Val Met
            740                 745                 750

Leu Val Val Val Ala Met Val Leu Phe Gly Leu Phe Asp Ala Leu
            755                 760             765

Asp Trp Ala Leu Glu Glu Leu Leu Val Ser Arg Pro Ser Leu Arg Arg
770                 775                 780

Leu Ala Arg Val Val Glu Cys Cys Val Met Ala Gly Glu Lys Ala Thr
785                 790                 795                 800

Thr Val Arg Leu Val Ser Lys Met Cys Ala Arg Gly Ala Tyr Leu Phe
            805                 810                 815

Asp His Met Gly Ser Phe Ser Arg Ala Val Lys Glu Arg Leu Leu Glu
            820                 825                 830

Trp Asp Ala Ala Leu Glu Xaa Leu Ser Phe Thr Arg Thr Asp Cys Arg
835                 840                 845

Ile Ile Arg Asp Ala Ala Arg Thr Leu Ser Cys Gly Gln Cys Val Met
850                 855                 860

Gly Leu Pro Val Val Ala Arg Arg Gly Asp Glu Val Leu Ile Gly Val
865                 870                 875                 880

Phe Gln Asp Val Asn His Leu Pro Pro Gly Phe Xaa Pro Thr Ala Pro
            885                 890                 895

Val Val Ile Arg Arg Cys Gly Lys Gly Phe Leu Gly Val Thr Lys Ala
            900                 905                 910

Ala Leu Thr Gly Arg Asp Pro Asp Leu His Pro Gly Asn Val Met Val
            915                 920                 925

Leu Gly Thr Ala Thr Ser Arg Ser Met Gly Thr Cys Leu Asn Gly Leu
            930                 935                 940

Leu Phe Thr Thr Phe His Gly Ala Ser Ser Arg Thr Ile Ala Thr Pro
945                 950                 955                 960

Val Gly Ala Leu Asn Pro Arg Trp Trp Ser Ala Ser Asp Asp Val Thr
            965                 970                 975

Val Tyr Pro Leu Pro Asp Gly Ala Asn Ser Leu Val Pro Cys Ser Cys
            980                 985                 990

Gln Ala Glu Ser Cys Trp Val Xaa Arg Ser Asp Gly Ala Leu Cys His
            995                 1000                1005

Gly Leu Ser Lys Gly Asp Lys Val Glu Leu Asp Val Ala Met Glu
    1010                1015                1020

Val Ala Asp Phe Arg Gly Ser Ser Gly Ser Pro Val Leu Cys Asp
    1025                1030                1035

Glu Gly His Ala Val Gly Met Leu Val Ser Val Leu His Ser Gly
    1040                1045                1050

Gly Arg Val Thr Ala Ala Arg Phe Thr Arg Pro Trp Thr Gln Val
    1055                1060                1065

Pro Thr Asp Ala Lys Thr Thr Thr Glu Pro Pro Pro Val Pro Ala
    1070                1075                1080

Lys Gly Val Phe Lys Glu Ala Pro Leu Phe Met Pro Thr Gly Ala
    1085                1090                1095

Gly Lys Ser Thr Arg Val Pro Leu Glu Tyr Gly Asn Met Gly His

-continued

```
                    1100                1105                1110
Lys Val Leu Ile Leu Asn Pro Ser Val Ala Thr Val Arg Ala Met
    1115                1120                1125
Gly Pro Tyr Met Glu Arg Leu Ala Gly Lys His Pro Ser Ile Phe
    1130                1135                1140
Cys Gly His Asp Thr Thr Ala Phe Thr Arg Ile Thr Asp Ser Pro
    1145                1150                1155
Leu Thr Tyr Ser Thr Tyr Gly Arg Phe Leu Ala Asn Pro Arg Gln
    1160                1165                1170
Met Leu Arg Gly Val Ser Val Val Ile Cys Asp Glu Cys His Ser
    1175                1180                1185
His Asp Ser Thr Val Leu Leu Gly Ile Gly Arg Val Arg Asp Val
    1190                1195                1200
Ala Arg Gly Cys Gly Val Gln Leu Val Leu Tyr Ala Thr Ala Thr
    1205                1210                1215
Pro Pro Gly Ser Pro Met Thr Gln His Pro Ser Ile Ile Glu Thr
    1220                1225                1230
Lys Leu Asp Val Gly Glu Ile Pro Phe Tyr Gly His Gly Ile Pro
    1235                1240                1245
Leu Glu Arg Met Arg Thr Gly Arg His Leu Val Phe Cys His Ser
    1250                1255                1260
Lys Ala Glu Cys Glu Arg Leu Ala Gly Gln Phe Ser Ala Arg Gly
    1265                1270                1275
Val Asn Ala Ile Ala Tyr Tyr Arg Gly Lys Asp Ser Ser Ile Ile
    1280                1285                1290
Lys Asp Gly Asp Leu Val Val Cys Ala Thr Asp Ala Leu Ser Thr
    1295                1300                1305
Gly Tyr Thr Gly Asn Phe Asp Ser Val Thr Asp Cys Gly Leu Val
    1310                1315                1320
Val Glu Glu Val Val Glu Val Thr Leu Asp Pro Thr Ile Thr Ile
    1325                1330                1335
Ser Leu Arg Thr Val Pro Ala Ser Ala Glu Leu Ser Met Gln Arg
    1340                1345                1350
Arg Gly Arg Thr Gly Arg Gly Arg Ser Gly Arg Tyr Tyr Tyr Ala
    1355                1360                1365
Gly Val Gly Lys Ala Pro Ala Gly Val Val Arg Ser Gly Pro Val
    1370                1375                1380
Trp Ser Ala Val Glu Ala Gly Val Thr Trp Tyr Gly Met Glu Pro
    1385                1390                1395
Asp Leu Thr Ala Asn Leu Leu Arg Leu Tyr Asp Asp Cys Pro Tyr
    1400                1405                1410
Thr Ala Ala Val Ala Ala Asp Ile Gly Glu Ala Ala Val Phe Phe
    1415                1420                1425
Ala Gly Leu Ala Pro Leu Arg Met His Pro Asp Val Ser Trp Ala
    1430                1435                1440
Lys Val Arg Gly Val Asn Trp Pro Leu Leu Val Gly Val Gln Arg
    1445                1450                1455
Thr Met Cys Arg Glu Thr Leu Ser Pro Gly Pro Ser Asp Asp Pro
    1460                1465                1470
Gln Trp Ala Gly Leu Lys Gly Pro Asn Pro Val Pro Leu Leu Leu
    1475                1480                1485
Arg Trp Gly Asn Asp Leu Pro Ser Lys Val Ala Gly His His Ile
    1490                1495                1500
```

```
Val Asp Asp Leu Val Arg Arg Leu Gly Val Ala Glu Gly Tyr Val
1505                1510                1515

Arg Cys Asp Ala Xaa Pro Ile Leu Met Val Gly Leu Ala Ile Ala
1520                1525                1530

Gly Gly Met Ile Tyr Ala Ser Tyr Thr Gly Ser Leu Val Val Val
1535                1540                1545

Thr Asp Trp Asp Val Lys Gly Gly Asn Pro Leu Tyr Arg Ser
1550                1555                1560

Gly Asp Gln Ala Thr Pro Gln Pro Val Val Gln Val Pro Pro Val
1565                1570                1575

Asp His Arg Pro Gly Gly Glu Ser Ala Pro Arg Asp Ala Lys Thr
1580                1585                1590

Val Thr Asp Ala Val Ala Ala Ile Gln Val Asn Cys Asp Trp Ser
1595                1600                1605

Val Met Thr Leu Ser Ile Gly Glu Val Leu Thr Leu Ala Gln Ala
1610                1615                1620

Lys Thr Ala Glu Ala Tyr Ala Ala Thr Ser Arg Trp Leu Ala Gly
1625                1630                1635

Cys Tyr Thr Gly Thr Arg Ala Val Pro Thr Val Ser Ile Val Asp
1640                1645                1650

Lys Leu Phe Ala Gly Gly Trp Ala Ala Val Val Gly His Cys His
1655                1660                1665

Ser Val Ile Ala Ala Ala Val Ala Ala Tyr Gly Ala Ser Arg Ser
1670                1675                1680

Pro Pro Leu Ala Ala Ala Ala Ser Tyr Leu Met Gly Leu Gly Val
1685                1690                1695

Gly Gly Asn Ala Gln Ala Arg Leu Ala Ser Ala Leu Leu Leu Gly
1700                1705                1710

Ala Ala Gly Thr Ala Leu Gly Thr Pro Val Val Gly Leu Thr Met
1715                1720                1725

Ala Gly Ala Phe Met Gly Gly Ala Ser Val Ser Pro Ser Leu Val
1730                1735                1740

Thr Val Leu Leu Gly Ala Val Gly Gly Trp Glu Gly Val Val Asn
1745                1750                1755

Ala Ala Ser Leu Val Phe Asp Phe Met Ala Gly Lys Leu Ser Thr
1760                1765                1770

Glu Asp Leu Trp Tyr Ala Ile Pro Val Leu Thr Ser Pro Xaa Ala
1775                1780                1785

Gly Leu Ala Gly Ile Ala Leu Gly Leu Val Leu Tyr Ser Ala Asn
1790                1795                1800

Asn Ser Gly Thr Thr Thr Trp Leu Asn Arg Leu Leu Thr Thr Leu
1805                1810                1815

Pro Arg Ser Ser Cys Ile Pro Asp Ser Tyr Phe Gln Gln Ala Asp
1820                1825                1830

Tyr Cys Asp Lys Val Ser Ala Ile Val Arg Arg Leu Ser Leu Thr
1835                1840                1845

Arg Thr Val Val Ala Leu Val Asn Arg Glu Pro Lys Val Asp Glu
1850                1855                1860

Val Gln Val Gly Tyr Val Trp Asp Leu Trp Glu Trp Val Met Arg
1865                1870                1875

Gln Val Arg Met Val Met Ser Arg Leu Arg Ala Leu Cys Pro Val
1880                1885                1890
```

| | | | | | | | | | | |
|---|---|---|---|---|---|---|---|---|---|---|
|Val|Ser|Leu|Pro|Leu|Trp|His|Cys|Gly|Glu|Gly|Trp|Ser|Gly|Glu|
|1895| | | |1900| | | |1905| | | | | | |
|Trp|Leu|Leu|Asp|Gly|His|Val|Glu|Ser|Arg|Cys|Leu|Cys|Gly|Cys|
|1910| | | |1915| | | |1920| | | | | | |
|Val|Ile|Thr|Gly|Asp|Val|Leu|Asn|Gly|Gln|Leu|Lys|Asp|Pro|Val|
|1925| | | |1930| | | |1935| | | | | | |
|Tyr|Ser|Thr|Lys|Leu|Cys|Arg|His|Tyr|Trp|Met|Gly|Thr|Val|Pro|
|1940| | | |1945| | | |1950| | | | | | |
|Val|Asn|Met|Leu|Gly|Tyr|Gly|Glu|Thr|Ser|Pro|Leu|Leu|Ala|Ser|
|1955| | | |1960| | | |1965| | | | | | |
|Asp|Thr|Pro|Lys|Val|Val|Pro|Phe|Gly|Thr|Ser|Gly|Trp|Ala|Glu|
|1970| | | |1975| | | |1980| | | | | | |
|Val|Val|Val|Thr|Pro|Thr|His|Val|Val|Ile|Arg|Arg|Thr|Ser|Cys|
|1985| | | |1990| | | |1995| | | | | | |
|Tyr|Lys|Leu|Leu|Arg|Gln|Gln|Ile|Leu|Ser|Ala|Ala|Val|Ala|Glu|
|2000| | | |2005| | | |2010| | | | | | |
|Pro|Tyr|Tyr|Val|Asp|Gly|Ile|Pro|Val|Ser|Trp|Glu|Ala|Asp|Ala|
|2015| | | |2020| | | |2025| | | | | | |
|Arg|Ala|Pro|Ala|Met|Val|Tyr|Gly|Pro|Gly|Gln|Ser|Val|Thr|Ile|
|2030| | | |2035| | | |2040| | | | | | |
|Asp|Gly|Glu|Arg|Tyr|Thr|Leu|Pro|His|Gln|Leu|Arg|Met|Arg|Asn|
|2045| | | |2050| | | |2055| | | | | | |
|Val|Ala|Pro|Ser|Glu|Val|Ser|Ser|Glu|Val|Ser|Ile|Glu|Ile|Gly|
|2060| | | |2065| | | |2070| | | | | | |
|Thr|Glu|Thr|Glu|Asp|Ser|Glu|Leu|Thr|Glu|Ala|Asp|Leu|Pro|Pro|
|2075| | | |2080| | | |2085| | | | | | |
|Ala|Ala|Ala|Ala|Leu|Gln|Ala|Ile|Glu|Asn|Ala|Ala|Arg|Ile|Leu|
|2090| | | |2095| | | |2100| | | | | | |
|Glu|Pro|His|Ile|Asp|Val|Xaa|Met|Glu|Asp|Cys|Ser|Thr|Pro|Ser|
|2105| | | |2110| | | |2115| | | | | | |
|Leu|Cys|Gly|Ser|Ser|Arg|Glu|Met|Pro|Val|Trp|Gly|Glu|Asp|Ile|
|2120| | | |2125| | | |2130| | | | | | |
|Pro|Arg|Thr|Pro|Ser|Pro|Ala|Leu|Ile|Ser|Val|Thr|Glu|Ser|Ser|
|2135| | | |2140| | | |2145| | | | | | |
|Ser|Asp|Glu|Lys|Thr|Leu|Ser|Val|Thr|Ser|Ser|Gln|Glu|Asp|Thr|
|2150| | | |2155| | | |2160| | | | | | |
|Pro|Ser|Ser|Asp|Ser|Phe|Glu|Val|Ile|Gln|Glu|Ser|Asp|Thr|Ala|
|2165| | | |2170| | | |2175| | | | | | |
|Glu|Ser|Glu|Glu|Ser|Val|Phe|Asn|Val|Ala|Leu|Ser|Val|Leu|Lys|
|2180| | | |2185| | | |2190| | | | | | |
|Ala|Leu|Phe|Pro|Gln|Ser|Asp|Ala|Thr|Arg|Lys|Leu|Thr|Val|Lys|
|2195| | | |2200| | | |2205| | | | | | |
|Met|Ser|Cys|Cys|Val|Glu|Lys|Ser|Val|Thr|Arg|Phe|Phe|Ser|Leu|
|2210| | | |2215| | | |2220| | | | | | |
|Gly|Leu|Thr|Val|Ala|Asp|Val|Ala|Ser|Leu|Cys|Glu|Met|Glu|Ile|
|2225| | | |2230| | | |2235| | | | | | |
|Gln|Asn|His|Thr|Ala|Tyr|Cys|Asp|Lys|Val|Arg|Thr|Pro|Leu|Glu|
|2240| | | |2245| | | |2250| | | | | | |
|Leu|Gln|Val|Gly|Cys|Leu|Val|Gly|Asn|Glu|Leu|Thr|Phe|Glu|Cys|
|2255| | | |2260| | | |2265| | | | | | |
|Asp|Lys|Cys|Glu|Ala|Arg|Gln|Glu|Thr|Leu|Ala|Ser|Phe|Ser|Tyr|
|2270| | | |2275| | | |2280| | | | | | |
|Ile|Trp|Ser|Gly|Val|Pro|Leu|Thr|Arg|Ala|Thr|Pro|Ala|Lys|Pro|

```
                  2285                2290                2295
Pro Val Val Arg Pro Val Gly Ser Leu Leu Val Ala Asp Thr Thr
                  2300                2305                2310
Lys Val Tyr Val Thr Asn Pro Asp Asn Val Gly Arg Arg Val Asp
                  2315                2320                2325
Lys Val Thr Phe Trp Arg Ala Pro Arg Val His Asp Lys Phe Leu
                  2330                2335                2340
Val Asp Ser Ile Glu Arg Ala Arg Arg Ala Ala Gln Gly Cys Leu
                  2345                2350                2355
Ser Met Gly Tyr Thr Tyr Glu Glu Ala Ile Arg Thr Val Arg Pro
                  2360                2365                2370
His Ala Ala Met Gly Trp Gly Ser Lys Val Ser Val Lys Asp Leu
                  2375                2380                2385
Ala Thr Pro Ala Gly Lys Met Ala Val His Asp Arg Leu Gln Glu
                  2390                2395                2400
Ile Leu Glu Gly Thr Pro Val Pro Phe Thr Leu Thr Val Lys Lys
                  2405                2410                2415
Glu Val Phe Phe Lys Asp Arg Lys Glu Lys Ala Pro Arg Leu
                  2420                2425                2430
Ile Val Phe Pro Pro Leu Asp Phe Arg Ile Ala Glu Lys Leu Ile
                  2435                2440                2445
Leu Gly Asp Pro Gly Arg Val Ala Lys Ala Gly Val Gly Gly Ala
                  2450                2455                2460
Tyr Ala Phe Gln Tyr Thr Pro Asn Gln Arg Val Lys Glu Met Leu
                  2465                2470                2475
Lys Leu Trp Glu Ser Lys Lys Thr Pro Cys Ala Ile Cys Val Asp
                  2480                2485                2490
Ala Thr Cys Phe Asp Ser Ser Ile Thr Glu Glu Asp Val Ala Leu
                  2495                2500                2505
Glu Thr Glu Leu Tyr Ala Leu Ala Ser Asp His Pro Glu Trp Val
                  2510                2515                2520
Arg Ala Leu Gly Lys Tyr Xaa Ala Ser Gly Thr Met Val Thr Pro
                  2525                2530                2535
Glu Gly Val Pro Val Gly Glu Arg Tyr Cys Arg Ser Ser Gly Val
                  2540                2545                2550
Leu Thr Thr Ser Ala Ser Asn Cys Leu Thr Cys Tyr Ile Lys Val
                  2555                2560                2565
Arg Ala Ala Cys Glu Arg Ile Gly Leu Lys Asn Val Ser Leu Leu
                  2570                2575                2580
Ile Ala Gly Asp Asp Cys Leu Ile Val Cys Glu Arg Pro Val Cys
                  2585                2590                2595
Asp Pro Cys Glu Ala Leu Gly Arg Thr Leu Ala Ser Tyr Gly Tyr
                  2600                2605                2610
Ala Cys Glu Pro Ser Tyr His Ala Ser Leu Asp Thr Ala Pro Phe
                  2615                2620                2625
Cys Ser Thr Trp Leu Ala Glu Cys Asn Ala Asp Gly Xaa Arg His
                  2630                2635                2640
Phe Phe Leu Thr Thr Asp Phe Arg Arg Pro Leu Ala Arg Met Ser
                  2645                2650                2655
Ser Glu Tyr Ser Asp Pro Met Ala Ser Ala Ile Gly Tyr Ile Leu
                  2660                2665                2670
Leu Tyr Pro Trp Xaa Pro Ile Thr Arg Trp Val Ile Ile Pro His
                  2675                2680                2685
```

```
Val Leu  Thr Cys Ala Ser  Ser Arg Gly Gly  Thr Xaa Ser Asp
    2690             2695              2700

Pro Val  Trp Cys Gln Val  His Gly Asn Tyr  Tyr Lys Phe Pro Leu
    2705             2710              2715

Asp Lys  Leu Pro Asn Ile  Ile Val Ala Leu  His Gly Pro Ala Ala
    2720             2725              2730

Leu Arg  Val Thr Ala Asp  Thr Lys Thr Lys  Met Glu Ala Gly
    2735             2740              2745

Lys Val  Leu Ser Asp Leu  Lys Leu Pro Gly  Leu Ala Val His Arg
    2750             2755              2760

Lys Lys  Ala Gly Ala Leu  Arg Thr Arg Met  Leu Arg Ser Arg Gly
    2765             2770              2775

Trp Ala  Glu Leu Ala Arg  Gly Leu Leu Trp  His Pro Gly Leu Arg
    2780             2785              2790

Leu Pro  Pro Pro Glu Ile  Ala Gly Ile Pro  Gly Gly Phe Pro Leu
    2795             2800              2805

Ser Pro  Pro Tyr Met Gly  Val Val His Gln  Leu Asp Phe Thr Ala
    2810             2815              2820

Gln Arg  Ser Arg Trp Arg  Trp Leu Gly Phe  Leu Ala Leu Leu Ile
    2825             2830              2835

Val Ala  Leu Phe Gly
    2840

<210> SEQ ID NO 3
<211> LENGTH: 936
<212> TYPE: DNA
<213> ORGANISM: Hepatitis GB virus C
<220> FEATURE:
<221> NAME/KEY: CDS
<222> LOCATION: (1)..(936)

<400> SEQUENCE: 3 acc ata gcc gca ctg gga tct tcg gat cgc gac aca gtg gtt gag ctc    48
Thr Ile Ala Ala Leu Gly Ser Ser Asp Arg Asp Thr Val Val Glu Leu
1               5                   10                  15 tcc gag tgg gga att ccc tgc gcc act tgt atc ctg gac agg cgg cct    96
Ser Glu Trp Gly Ile Pro Cys Ala Thr Cys Ile Leu Asp Arg Arg Pro
            20                  25                  30 gcc tcg tgt ggc acc tgt gtg agg gac tgc tgg ccc gag acc ggg tcg   144
Ala Ser Cys Gly Thr Cys Val Arg Asp Cys Trp Pro Glu Thr Gly Ser
        35                  40                  45 gta cgt ttc cca ttc cac agg tgt ggc gcg gga ccg agg ctg acc aga   192
Val Arg Phe Pro Phe His Arg Cys Gly Ala Gly Pro Arg Leu Thr Arg
    50                  55                  60 gac ctt gag gct gtg ccc ttc gtc aat agg aca act ccc ttc acc ata   240
Asp Leu Glu Ala Val Pro Phe Val Asn Arg Thr Thr Pro Phe Thr Ile
65                  70                  75                  80 agg ggg ccc ctg ggc aac cag ggg cga ggc aac ccg gtg cgg tcg ccc   288
Arg Gly Pro Leu Gly Asn Gln Gly Arg Gly Asn Pro Val Arg Ser Pro
                85                  90                  95 ttg ggt ttt ggg tcc tac acc atg acc aag atc cga gac tcc tta cac   336
Leu Gly Phe Gly Ser Tyr Thr Met Thr Lys Ile Arg Asp Ser Leu His
            100                 105                 110 ttg gtg aaa tgt ccc acc cca gcc att gag cct ccc acc gga acg ttt   384
Leu Val Lys Cys Pro Thr Pro Ala Ile Glu Pro Pro Thr Gly Thr Phe
        115                 120                 125 ggg ttc ttc cca gga gtc ccc ccc ctt aac aac tgc atg ctt ctc ggc   432
Gly Phe Phe Pro Gly Val Pro Pro Leu Asn Asn Cys Met Leu Leu Gly
```

```
                 130                135                140
act gag gtg tca gag gta ttg ggt ggg gcg ggc ctc act ggg ggg ttt      480
Thr Glu Val Ser Glu Val Leu Gly Gly Ala Gly Leu Thr Gly Gly Phe
145                 150                155                160 tac gaa cct ctg gtg cgg cgg tgt tca gag ctg atg ggt cgg cgg aat      528
Tyr Glu Pro Leu Val Arg Arg Cys Ser Glu Leu Met Gly Arg Arg Asn
                165                170                175 ccg gtc tgc ccg ggg ttt gca tgg ctc tct tcg gga cgg cct gat ggg      576
Pro Val Cys Pro Gly Phe Ala Trp Leu Ser Ser Gly Arg Pro Asp Gly
            180                185                190 ttc ata cat gtt cag ggc cac ttg cag gag gtg gat gcg ggc aac ttc      624
Phe Ile His Val Gln Gly His Leu Gln Glu Val Asp Ala Gly Asn Phe
        195                200                205 att ccg ccc cca cgc tgg ttg ctc ttg gac ttt gta ttt gtc ctg tta      672
Ile Pro Pro Pro Arg Trp Leu Leu Leu Asp Phe Val Phe Val Leu Leu
    210                215                220 tac ctg atg aag ctg gca gag gca cgg ttg gtc ccg ctg atc ctc ctc      720
Tyr Leu Met Lys Leu Ala Glu Ala Arg Leu Val Pro Leu Ile Leu Leu
225                230                235                240 ctg cta tgg tgg tgg gtg aac cag ttg gcg gtc ctt gkt gtg scg gct      768
Leu Leu Trp Trp Trp Val Asn Gln Leu Ala Val Leu Xaa Val Xaa Ala
                245                250                255 gck crc gcc gcc gtg gct gga gag gtg ttt gcg ggc cct gcc ttg tcc      816
Ala Xaa Ala Ala Val Ala Gly Glu Val Phe Ala Gly Pro Ala Leu Ser
            260                265                270 tgg tgt ctg ggc cta ccc ttc gtg agt atg atc ctg ggg cta gca aac      864
Trp Cys Leu Gly Leu Pro Phe Val Ser Met Ile Leu Gly Leu Ala Asn
        275                280                285 ctg gtg ttg tac ttc cgc tgg atg ggt cct caa cgc ctg atg ttc ctc      912
Leu Val Leu Tyr Phe Arg Trp Met Gly Pro Gln Arg Leu Met Phe Leu
    290                295                300 gtg ttg tgg aag ctc gct cgg ggg                                      936
Val Leu Trp Lys Leu Ala Arg Gly
305                310
```

<210> SEQ ID NO 4
<211> LENGTH: 312
<212> TYPE: PRT
<213> ORGANISM: Hepatitis GB virus C
<220> FEATURE:
<221> NAME/KEY: misc_feature
<222> LOCATION: (253)..(253)
<223> OTHER INFORMATION: The 'Xaa' at location 253 stands for Gly, or Val.
<220> FEATURE:
<221> NAME/KEY: misc_feature
<222> LOCATION: (255)..(255)
<223> OTHER INFORMATION: The 'Xaa' at location 255 stands for Ala, or Pro.
<220> FEATURE:
<221> NAME/KEY: misc_feature
<222> LOCATION: (258)..(258)
<223> OTHER INFORMATION: The 'Xaa' at location 258 stands for Arg, or His.

<400> SEQUENCE: 4

```
Thr Ile Ala Ala Leu Gly Ser Ser Asp Arg Asp Thr Val Val Glu Leu
1               5                   10                  15

Ser Glu Trp Gly Ile Pro Cys Ala Thr Cys Ile Leu Asp Arg Arg Pro
                20                  25                  30

Ala Ser Cys Gly Thr Cys Val Arg Asp Cys Trp Pro Glu Thr Gly Ser
            35                  40                  45

Val Arg Phe Pro Phe His Arg Cys Gly Ala Gly Pro Arg Leu Thr Arg
```

```
                50                  55                  60
Asp Leu Glu Ala Val Pro Phe Val Asn Arg Thr Thr Pro Phe Thr Ile
 65                  70                  75                  80

Arg Gly Pro Leu Gly Asn Gln Gly Arg Gly Asn Pro Val Arg Ser Pro
                 85                  90                  95

Leu Gly Phe Gly Ser Tyr Thr Met Thr Lys Ile Arg Asp Ser Leu His
            100                 105                 110

Leu Val Lys Cys Pro Thr Pro Ala Ile Glu Pro Pro Thr Gly Thr Phe
        115                 120                 125

Gly Phe Phe Pro Gly Val Pro Pro Leu Asn Asn Cys Met Leu Leu Gly
    130                 135                 140

Thr Glu Val Ser Glu Val Leu Gly Gly Ala Gly Leu Thr Gly Gly Phe
145                 150                 155                 160

Tyr Glu Pro Leu Val Arg Arg Cys Ser Glu Leu Met Gly Arg Arg Asn
                165                 170                 175

Pro Val Cys Pro Gly Phe Ala Trp Leu Ser Ser Gly Arg Pro Asp Gly
            180                 185                 190

Phe Ile His Val Gln Gly His Leu Gln Glu Val Asp Ala Gly Asn Phe
        195                 200                 205

Ile Pro Pro Pro Arg Trp Leu Leu Asp Phe Val Phe Val Leu Leu
    210                 215                 220

Tyr Leu Met Lys Leu Ala Glu Ala Arg Leu Val Pro Leu Ile Leu Leu
225                 230                 235                 240

Leu Leu Trp Trp Trp Val Asn Gln Leu Ala Val Leu Xaa Val Xaa Ala
                245                 250                 255

Ala Xaa Ala Ala Val Ala Gly Glu Val Phe Ala Gly Pro Ala Leu Ser
            260                 265                 270

Trp Cys Leu Gly Leu Pro Phe Val Ser Met Ile Leu Gly Leu Ala Asn
        275                 280                 285

Leu Val Leu Tyr Phe Arg Trp Met Gly Pro Gln Arg Leu Met Phe Leu
    290                 295                 300

Val Leu Trp Lys Leu Ala Arg Gly
305                 310

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Leu Thr Gly Gly Phe Tyr Glu Pro Leu
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Gly Gly Ala Gly Leu Thr Gly Gly Phe Tyr Glu Pro Leu Val Arg Arg
1               5                   10                  15

Cys
```

```
<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Leu Thr Gly Gly Phe Tyr Glu Pro Leu Val Arg Arg Cys
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Phe Tyr Glu Pro Leu Val Arg Arg Cys
1               5
```

METHOD OF INDUCING A CROSS-REACTIVE HIV-1 IMMUNE RESPONSE BY ADMINISTERING A COMPOSITION COMPRISING THE GBV-C E2 PROTEIN

This application is a divisional application of U.S. patent application Ser. No. 12/179,399, filed Jul. 24, 2008, which is a divisional application of U.S. patent application Ser. No. 10/862,061, filed Jun. 4, 2004, now abandoned, which claims priority to U.S. Provisional Patent Application Ser. No. 60/475,987, filed on Jun. 5, 2003. The entire contents of each of the above-referenced disclosures are specifically incorporated herein by reference.

This invention was made with government support under AA012671 awarded by the National Institues of Health. The government has certain rights in the invention.

The sequence listing that is contained in the file named "IOWAP0053USD2_ST25.txt", which is 79 KB (as measured in Microsoft Windows®) and was created on Aug. 14, 2014, is filed herewith by electronic submission and is incorporated by reference herein.

BACKGROUND OF THE INVENTION

I. Field of the Invention

The present invention relates generally to the fields of molecular biology and virology. More particularly, it concerns methods and compositions to treat, inhibit or prevent HIV infection.

II. Description of Related Art

A. GB Virus Type C

GB virus type C (GBV-C), also known as hepatitis G virus (HGV), is a virus whose genomic organization and nucleotide sequence places it in the Flavivirus family (Robertson et al., 1998). It is the most closely related human virus to hepatitis C virus (HCV) (Leary et al., 1996; Linnen et al., 1996; Simons et al., 1995). It has been suggested that these viruses should be classified together with non-human GB-hepatitis agents as the hepacivirus genus. Although GBV-C was originally associated with post-transfusion hepatitis in humans (Linnen et al., 1996), subsequent epidemiological studies indicated that it does not cause acute or chronic hepatitis (Alter et al., 1997a; Alter et al., 1997b). In addition, experimental GBV-C infection of chimpanzees was not associated with acute hepatitis (Bukh et al., 1998).

Persistent GBV-C viremia (as detected by RT-PCR) is common, with 0.9% to 3% of healthy U.S. blood donors and approximately 20%-30% of patients with HCV infection persistently infected with GBV-C (Dawson et al., 1996; Feucht et al., 1997; Simons et al., 1995a; Simons et al., 1995b; Tacke et al., 1997). Following infection, about 80% of people clear their viremia, concomitantly developing antibody to the GBV-C E2 protein (Feucht et al., 1997; Thomas et al., 1998). Thus, it is estimated that approximately 20% of infected people remain viremic for long periods of time. GBV-C appears to be transmitted primarily by parenteral exposure (Simons et al., 1995), although there are data suggesting that sexual and/or household transmission of GBV-C infection may occur (Akiyoshi et al., 1999; de Martino et al., 1998; Nerurkar et al., 1998; Tanaka et al., 1997; Wu et al., 1997).

B. GBV-C and HIV

GBV-C has been investigated in the context of HIV infection. The course of HIV-1 infection is extremely variable among infected individuals, although the reasons for this observation are not fully understood. Individuals whose HIV disease progresses slowly are often called long-term non-progressors (LTNPs). The prevalence of LTNPs varies from 1% to 25% of infected people, depending upon the definition used (reviewed in Easterbrook, 1999). There are no specific clinical criteria for LTNP. However, non-progression generally implies the absence of HIV-related clinical disease 10 or more years following infection and an absolute CD4 count of $\geq 500$ cells/mm$^3$ (Easterbrook, 1999). Evaluation of LTNP's has identified HIV isolates with deletions in key replicative genes (Deacon et al., 1995) and host genetic factors, including specific HLA haplotypes (reviewed in reference Rowland-Jones, 1999). In some individuals, polymorphisms that result in absent or reduced expression of HIV co-receptors have been identified (Huang et al., 1996). However, these findings are uncommon and thought to account for no more than one-third of LTNP's (Rowland-Jones, 1999).

Persistent GBV-C infection is common in humans, with infection rates of approximately 0.9% to 3% in healthy blood donors, 20-30% in HCV-positive people (Dawson et al., 1996), and 35%-40% in HIV-positive individuals. GBV-C infection can persist for decades in the absence of any clinical morbidity or mortality. Among immune-competent individuals, it is estimated that 60% to 75% of GBV-C-infected people clear the infection, concomitantly developing antibodies to the envelope glycoprotein E2 (Thomas et al., 1998). It is also known that GBV-C can be propagated in cultures of peripheral blood mononuclear cells (PBMC's) (Fogeda et al., 1999).

In 1998, Toyoda et al. found that hemophiliacs co-infected with HIV and GBV-C had a lower plasma HIV RNA concentration and a lower incidence of AIDS diagnoses compared to those infected with HIV alone (Toyoda et al., 1998), although the differences were not statistically significant. In contrast, Sabin and colleagues found an increased rate of AIDS and death in hemophiliacs "exposed" to GBV-C (Sabin et al., 1998) compared to non-exposed individuals. This study included HIV-positive subjects who were either GBV-C viremic as determined by detection of GBV-C RNA in plasma, or HIV-infected people who were not viremic but were anti-GBV-C E2 antibody-positive. Although the mortality rate was higher among the GBV-C "exposed" individuals, the results were not statistically significant. Looking at HIV-infected persons, Lefrère and colleagues reported a significant delay in the rate of CD4+ T cell decline, development of AIDS, and death in 23 HIV-positive individuals with GBV-C viremia compared to 72 HIV-infected people without GBV-C viremia (Lefrère et al., 1999). In this study, HIV-infected individuals who were also GBV-C-positive were compared to HIV-infected individuals who were GBV-C-negative. When these subjects were matched by age, sex, baseline HIV RNA load, and baseline CD4 T cell count, HIV disease progression appeared to be worse in GBV-C-negative subjects.

During progressive human immunodeficiency virus type 1 (HIV-1) infection, the virus-specific immune responses of an infected subject gradually deteriorate, leading to the development of acquired immunodeficiency syndrome (AIDS). Most infected patients do not exhibit overt clinical manifestations of the disease for six to ten years following initial infection, however, most individuals infected with HIV eventually die from conditions or infections; that the individual's immune system is no longer equipped to fight. While treatment for AIDS has been forthcoming, no effective cure has been reported. Thus, preventative and treatment options against HIV infection and the development of AIDS remain highly desirable.

SUMMARY OF THE INVENTION

Embodiments of the invention provide improved methods and compositions for therapeutic and/or prophylatic treatment of HIV infection. Aspects of the invention include compositions and methods related to antigens and/or polypeptides or peptides derived from GBV-C proteins or envelope proteins, in particular GBV-C envelope protein E2 (E2). In other aspects, the invention includes compositions and methods related to antibodies and other binding agents that bind antigens derived from GBV-C proteins. In other aspects, the invention includes compositions and methods related to the use of compositions comprising one or more GBV-C polypeptides or peptides for therapeutic or prophylatic administration. Compositions and methods comprising GBV-C polypeptides, GBV-C binding agents, or polynucleotides expressing the same can be used to stimulate or provide anti-HIV activity, including, but not limited to inhibition of HIV replication, inhibition of HIV processing, HIV neutralization, inhibition of HIV infection, or a decreased or delayed mortality in infected persons.

Embodiments of the invention include a therapeutic composition comprising a GBV-C polypeptide or peptide, or a GBV-C polypeptide or peptide binding agent, wherein the composition attenuates HIV infectivity. The binding agent may be an antibody, an aptamer, or any other known binding agent that can be selected or screened for binding to GBV-C polypeptides or fragments thereof including, but not limited to GBV-C E2 polypeptides or peptides. In certain embodiments, the antibody may be a polyclonal antibody, a monoclonal antibody or a fragment or mimetic thereof. An antibody of the invention may be a humanized antibody, human antibody, or a human mouse, or human library derived monoclonal antibody. In certain embodiments, a GBV-C peptide can be derived from a GBV-C envelope protein. In particular embodiments, the GBV-C envelope protein is an E2 protein.

Embodiments of the invention include methods for preventing or treating HIV infection comprising administering to a subject a composition comprising a GBV-C polypeptide or peptide-binding agent. The binding agent may attenuate HIV infectivity. The binding agent may be an aptamer, an anti-GBV-C antibody, an antibody-like molecule, or other known binding agent that binds to a GBV-C polypeptide or peptide. In certain embodiments, the anti-GBV-C binding agent binds to a GBV-C E2 polypeptide or peptide. An anti-GBV-C antibody can be an anti-GBV-C E2 antibody. An antibody of the invention may be a polyclonal, monoclonal or a fragment or mimetic thereof. An antibody of the invention may be a humanized antibody, human antibody, or a human mouse, or human library derived monoclonal antibody.

In certain embodiments, methods may include administration of at least a second anti-HIV therapy. A second anti-HIV therapy may be an administration of an infectious GBV-C virus, HAART therapy, AZT therapy, or other known HIV therapies. The second therapy may be administered before, after or during a therapy comprising a GBV-C binding agent or GBV-C polypeptide or peptide. In a particular embodiment, a method may include administering the GBV-C virus before a therapeutic composition of the invention. A therapeutic composition of the invention may be administered at least 2, 3, 4, 5, 6, 7, 8, 9, 10 or more times over minutes, hours, days, weeks, months and/or years.

Embodiments of the invention include methods of preparing an antibody or other GBV-C binding agent by immunizing a non-human animal with a GBV-C polypeptide or fragment thereof, or a GBV-C E2 polypeptide or fragment thereof, or screening recombinant human antibody libraries with the above. In certain aspects, an antigen may be a GBV-C E2 derived peptide. In particular embodiments, the peptide may include, but is not limited to, LTGGFYEPLVRRC (SEQ ID NO:6), GGAGLTGGFYEPLVRRC (SEQ ID NO:7), or FYEPLVRRC (SEQ ID NO:8).

Methods of preparing a therapeutic composition may comprise contacting a cell with a polynucleotide encoding a GBV-C polypeptide or peptide binding agent under conditions effective to allow expression of all or part of a GBV-C polypeptide or peptide binding agent; collecting the expressed GBV-C polypeptide or peptide binding agent; and constituting the GBV-C polypeptide or peptide binding agent in a pharmaceutically acceptable solution. The binding agent may attenuate, inhibit, and/or modify HIV. A GBV-C polypeptide or peptide binding agent may be an aptamer, an antibody, or a related molecule. An antibody or related molecule may be humanized.

Certain embodiments include vaccines comprising an antigen derived from a GBV-C polypeptide. The antigen may be all or part of a GBV-C polypeptide including, but not limited to a GBV-C E2 polypeptide. In certain embodiments, the antigen may be a GBV-C E2-derived peptide. In particular embodiments, the peptide may include, but is not limited to, LTGGFYEPLVRRC (SEQ ID NO:6), or GGAGLTGGFYEPLVRRC (SEQ ID NO:7), or FYEPLVRRC (SEQ ID NO:8).

Embodiments of the invention include methods of immunizing a subject comprising contacting said subject with a composition comprising a GBV-C polypeptide or fragment thereof. The composition may further comprise an adjuvant. In certain embodiments, the GBV-C polypeptide is an E2 polypeptide.

In still further embodiments, polypeptides and/or peptides of the invention may be used as competitors for HIV binding to or association with various components of the human body.

The use of the word "a" or "an" when used in conjunction with the term "comprising" in the claims and/or the specification may mean "one," but it is also consistent with the meaning of "one or more," "at least one," and "one or more than one." Furthermore, where multiple steps of a method of process are cited, it is understood that the steps are not required to be performed in the particular order recited unless one of skill in the art is not be able to practice the method in a different order.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
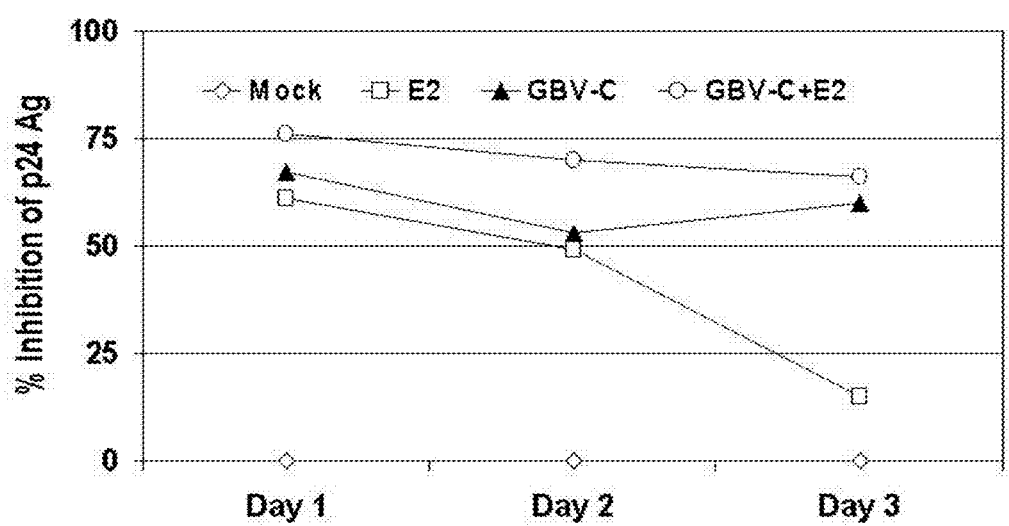
FIG. 1. Exemplary effect of E2 antibody positive serum on HIV replication.

Anti-retroviral medications suppress viral replication in HIV disease, yet they have failed to eradicate the virus from the body due to the multi-faceted nature of HIV infection, as well as the complexities of the immune system. Methods are being developed that both prevent infection and boost the immune system to keep it functioning at a level where it can assist in fighting HIV infection.

Thus, embodiments of the invention provide additional methods and compositions for therapeutic and/or prophylatic treatment of HIV infection. Aspects of the invention include compositions and methods related to antigens derived from GBV-C envelope proteins, in particular GBV-C envelope protein E2 (E2). In other aspects, the invention includes compositions and methods related to antibodies and other binding agents that bind antigens derived from GBV-C proteins. In particular, binding agents, such as aptamers and anti-GBV-C antibodies that bind GBV-C E2 proteins, are contemplated. In particular embodiments, a therapeutic GBV-C binding agent is contemplated for the treatment of HIV infection. Certain embodiments of the invention include combination treatments for HIV infection using compositions of the invention in combination with other anti-retroviral or HIV therapies.

The inventors have shown that HIV-infected subjects that are co-infected with GB virus C (GBV-C) typically have reduced mortality and slower progression to AIDS as compared to HIV-infected subjects without GBV-C co-infection. Infection of peripheral blood mononuclear cells (PBMCs) with GBV-C and HIV results in inhibition of HIV-1 replication. GBV-C infection typically inhibits HIV by inducing β-chemokines and reducing expression of the HIV co-receptor CCR5, explaining part of the beneficial clinical findings of GBV-C on HIV disease progression. Antibodies directed to the GBV-C virus have been noted and are typically used as a diagnostic agents, with no therapeutic use having been ascribed to them. The inventors now describe a therapeutic use for antibodies and/or binding agents that bind GBV-C proteins (e.g., envelope proteins), and antigens used for producing these antibodies or binding agents. In certain embodiments, a vaccine composition includes peptides derived from GBV-C polypeptides. In further aspects, the peptides themselves may bind to or associate with binding sites within an organism that also bind to HIV, thus the peptides themselves may be used as competitive inhibitors of HIV binding or localization in a host organism.

Embodiments of the invention include anti-GBV-C antibodies that also attenuate the infectivity of HIV. Antibodies against the GBV-C envelope glycoprotein E2 (GBV-C-E2), derived form either passive or active vaccination, are of particular interest for attenuation of HIV. The invention concerns the observation that antibodies against GBV-C peptides and polypeptides may react with and attenuate HIV. These antibodies may be induced or administered in a pharmaceutical composition for the therapeutic or prophylatic treatment of HIV infection. Infectious GBV-C can be used in combination with the present invention for preventative or therapeutic treatments for HIV infection and related conditions such as AIDS.

I. GBV-C Virus

Like other members of the Flaviviridae, GBV-C is a positive-strand RNA virus that encodes a single long open reading frame (Leary et al., 1996). GBV-C does not cause acute or chronic hepatitis, yet it is the family member most closely related to HCV, the cause of hepatitis C. Sequences of GBV-C have been previously reported, for example in U.S. Pat. No. 5,874,563, which is specifically incorporated by reference. In particular, an infectious GBV-C clone has been described in the PCT application WO 01/77157, which is incorporated herein by reference.

The GBV-C polyprotein is predicted to be cleaved into two envelope proteins (E1 and E2, referred to collectively as GBV-C envelope protein), an RNA helicase, a trypsin-like serine protease, and an RNA-dependent RNA polymerase. A major difference between GBV-C and HCV is in the amino terminus of the polyprotein. In many isolates, this region is truncated, and no core (or nucleocapsid) protein is present (Simons et al., 1995; Xiang et al., 1999). In vitro translation experiments suggest that the AUG immediately upstream of the putative E1 protein is preferentially used to initiate translation, although there may be as many as four AUG's in frame with the polyprotein upstream of this AUG (Simons et al., 1996).

The site of GBV-C replication has not been clearly identified, but it appears that replication in the hepatocyte, if it occurs, is not the primary source of virus in infected individuals (Laskus et al., 1998; Pessoa et al., 1998; Seipp et al., 1999). Recently, there were reports that human peripheral blood mononuclear cells (PBMC's) and interferon-resistant Daudi cells are permissive for GBV-C replication (Fogeda et al., 1999; Shimizu, 1999). In addition, transient replication of GBV-C was described in MT-2 cells (a human T-cell line), and PH5CH (a human hepatocyte line immortalized with simian virus 40 large T antigen) (Seipp et al., 1999).

II. GBV-C Polypeptides

In certain aspects, the invention is directed to the function, activity, or antigenicity of various components of an infectious GBV-C virus or a polypeptide derived there from, in particular the E2 protein. The expression or isolation of certain GBV-C polypeptides can be used to stimulate an anti-HIV activity, including inhibition of replication, processing, neutralization, and infection. SEQ ID NO:2 and 4 represent the translated product of SEQ ID NO:1 (GBV-C polyprotein) and 3 (GBV-C E2 protein), respectively. It is contemplated that the compositions and methods disclosed herein may be utilized to express all or part of SEQ ID NO:2 or 4 and derivates thereof. In certain embodiments, compositions of the invention may include the nucleic acids encoding the peptides as set forth in SEQ ID NOs:5, 6, 7 or 8. Determination of which molecules possess or stimulate an anti-HIV response may be achieved using functional assays measuring HIV infectivity, which are familiar to those of skill in the art. In other embodiments of the invention, heterologous polypeptides may be encoded by a sequence that also contains GBV-C sequences. "Heterologous" polypeptide indicates the polypeptide is not a GBV-C polypeptide. An endogenous GBV-C polypeptide refers to a polypeptide encoded by GBV-C viral RNA. Such a polypeptide would possess the same or similar sequence as SEQ ID NO:2, 4, 5, 6, 7 or 8.

In certain embodiments, an antigen containing a 9 amino acid sequence FYEPLVRRC (SEQ ID NO:8) or derivative thereof is contemplated. In certain embodiments, an antigen comprising a 13 amino acid sequence (LTGGFYEPLVRRC, SEQ ID NO:6) or a derivative thereof is contemplated. In still further embodiments, an antigen comprising a 17 amino acid sequence (GGAGLTGGFYEPLVRRC, SEQ ID NO:7) or derivative there of is contemplated. The structure of the various peptides can be modeled or resolved by computer modeling, NMR, or x-ray crystallography. Peptide structures may be used to engineer derivatives of the various E2 protein sequences or to engineer other molecules to interact with the peptides, such as antibodies or other affinity reagents. Amino acids or peptides of the invention may be used as an HIV disease-modifying immunogen (vaccine). Peptides may be used to inhibit, produce, or design inhibitors of HIV (as a prototype drug), as well as being used to induce anti-HIV antibodies (as a vaccine).

A. Variants of GBV-C Polypeptides

Embodiments of the invention include various GBV-C polypeptides, peptides, and derivatives thereof. Amino acid sequence variants of a polypeptide can be substitutional, insertional or deletion variants. Deletion variants lack one or more residues of the native protein that are not essential for function or immunogenic activity. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of GBV-C polypeptides, for example SEQ ID NO:2, 4, 5, 6, 7, or 8, provided the biological activity, e.g., immunogenicity, of the protein or peptide is maintained.

The term "functionally equivalent codon" is used herein to refer to codons that encode the same amino acid, such as the six codons for arginine or serine, and also refers to codons that encode biologically equivalent amino acids (see Table 1, below).

Certain embodiments of the invention include various peptides and/or fusion proteins of GBV-C polypeptides, in particular GBV-C E2 protein. For example, all or part of a GBV-C and/or a GBV-C E2 protein as set forth in SEQ ID NO:2, 4, 5, 6, 7 and/or 8 may be used in various embodiments of the invention. In certain embodiments, a fragment of the E2 or other GBV-C protein may comprise, but is not limited to about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500, or greater amino acid molecule residues, and any range derivable therein.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological activity (e.g., immunogenicity) where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a GBV-C polypeptide or peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA or RNA coding sequence, and nevertheless produce a protein with like properties. It is thus contemplated by the inventors that various changes may be made in the DNA or RNA sequences of genes or coding regions without appreciable loss of their biological utility or activity, as discussed herein. Table 1 shows the codons that encode particular amino acids.

TABLE 1

CODON TABLE

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG CGU |
| Serine | Ser | S | AGC | AGU | UCA | UCC | UCG UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

It is understood that an amino acid substituted for another having a similar hydrophilicity value still produces a biologically equivalent and immunologically equivalent protein.

In certain embodiments, a GBV-C polypeptide may be a fusion protein. Fusion proteins may alter the characteristics of a given polypeptide, such antigenicity or purification characteristics. A fusion protein is a specialized type of insertional variant. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals, or transmembrane regions.

B. In Vitro Production of GBV-C or Anti-GBV-C Polypeptides or Peptides

Various types of expression vectors are known in the art that can be used for the production of protein products. Following transfection with a expression vector, a cell in culture, e.g., a primary mammalian cell, a recombinant product may be prepared in various ways. A host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented (for exemplary methods see Freshney, 1992).

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large-scale production of cells and cell products. However, suspension cultured cells have limitations, such as tumorigenic potential and lower protein production than adherent cells.

In further aspects of the invention, other protein production methods known in the art may be used, including but not limited to prokaryotic, yeast, and other eukaryotic hosts such as insect cells and the like.

C. Protein Purification

It may be desirable to purify anti-GBV-C and/or GBV-C polypeptides and peptides, or variants and derivatives thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, hydrophobic interaction chromatography, exclusion chromatography; polyacrylamide gel electrophoresis; isoelectric focusing. A particularly efficient method of purifying peptides is fast protein liquid chromatography or even FPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme.

III. GBV-C Polynucleotides

Certain embodiments of the invention include GBV-C polynucleotides or nucleic acid molecules and fragments thereof. The polynucleotides of the invention may be isolated and purified from GBV-C virus or cells infected or transfected with GBV-C polynucleotides. The term isolated indicating they are free or substantially free from total viral or cellular genomic RNA or DNA, and proteins. It is contemplated that an isolated and purified GBV-C nucleic acid molecule may take the form of RNA or DNA. A GBV-C nucleic acid molecule refers to an RNA or DNA molecule that is capable of yielding all or part of a GBV-C polyprotein from a transfected cell.

As used in this application, the term "polynucleotide" refers to a nucleic acid molecule, RNA, or DNA that has been isolated free of total genomic nucleic acid. Therefore, a "polynucleotide encoding all or part of GBV-C" refers to a nucleic acid segment that contains GBV-C coding sequences, yet is isolated away from, or purified and free of, total viral genomic RNA and proteins; similarly, a "polynucleotide encoding full-length GBV-C" refers to a nucleic acid segment that contains full-length GBV-C coding sequences yet is isolated away from, or purified and free of, total viral genomic RNA and protein. Therefore, when the present application refers to the function or activity of an infectious GBV-C that is encoded by a GBV-C polynucleotide, it is meant that the polynucleotide encodes a molecule that has the ability to propagate an infectious GBV-C virus particle from a cell. It is contemplated that a GBV-C polynucleotide may refer to a GBV-C RNA transcript that is able to propagate an infectious GBV-C virus particle after introduction to a cell or to a GBV-C expression construct, clone, or vector composed of double-stranded DNA or DNA/RNA hybrid that is similarly capable.

The term "cDNA" is intended to refer to DNA prepared using RNA as a template. The advantage of using a cDNA, as opposed to genomic RNA or an RNA transcript is stability and the ability to manipulate the sequence using recombinant DNA technology (See Maniatis, 1989; Ausubel, 1994). There may be times when the full or partial genomic sequence is preferred. Alternatively, cDNAs may be advantageous because it represents coding regions of a polypeptide and eliminates introns and other regulatory regions.

It also is contemplated that a given GBV-C may be represented by natural variants or strains that have slightly different nucleic acid sequences but, nonetheless, encode the same viral polypeptides (see Table 1 above). Consequently, the present invention also encompasses derivatives of GBV-C with minimal amino acid changes in its viral proteins, but that possesses the same activities.

The term "gene" is used for simplicity to refer to the nucleic acid giving rise to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule encoding GBV-C may contain a contiguous nucleic acid sequence encoding one or more GBV-C genes and regulatory regions and be of the following lengths: about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more nucleotides, nucleosides, or base pairs. Such sequences may be identical or complementary to all or part of SEQ ID NO:1, 3 or Genbank Accession numbers AY196904 or AF070476 or segments thereof, e.g., those segments related to peptides of SEQ ID NO:5, 6, 7 or 8.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

In particular embodiments, the invention concerns isolated nucleic acid segments and recombinant vectors incorporating DNA sequences that encode GBV-C polypeptides or peptides that include within its amino acid sequence a contiguous amino acid sequence in accordance with, or essentially corresponding to GBV-C polypeptides.

Certain embodiments include nucleic acids segments and recombinant vectors encoding polypeptides and peptides to induce or enhance immune responses in both subjects having HIV, suspected of having HIV, at risk of being exposed to HIV and/or animals or cells for the production of anti-GBV-C antibodies.

The nucleic acid segments used in the present invention, regardless of the length of the coding sequence itself, may be combined with other DNA or RNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

In a non-limiting example, one or more nucleic acid constructs may be prepared that include a contiguous stretch of nucleotides identical to or complementary to GBV-C. A nucleic acid construct may be about 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 20,000, 30,000, 50,000, 100,000, 250,000, about 500,000, 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.

The nucleic acid segments used in the present invention encompass biologically functional and/or immunogenically equivalent GBV-C proteins and peptides. Such sequences may arise as a consequence of codon redundancy and functional equivalency that are known to occur naturally within nucleic acid sequences and the proteins thus encoded. Alternatively, functionally and immunologically equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein.

A. Vectors Encoding GBV-C

The present invention encompasses the use of vectors to encode for all or part of one or more GBV-C polypeptides, including an infectious GBV-C. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). In particular embodiments, gene therapy or immunization vectors are contemplated. One of skill in the art would be well equipped to construct a vector through standard recombinant techniques, which are described in Maniatis et al., 1988 and Ausubel et al., 1994, both incorporated herein by reference.

The term "expression vector" or "expression construct" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra. It is contemplated that an infectious GBV-C particle of the present invention may arise from a vector containing GBV-C sequence or RNA encoding GBV-C sequence into a cell. Either of these, or any other nucleic acid molecules of the present invention may be constructed with any of the following nucleic acid control sequences. Thus, the full-length RNA transcript may contain the benefit of recombinant DNA technology such that it contains exogenous control sequences or genes.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" means that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202 and U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or exogenous, i.e., from a different source than GBV-C sequence. In some examples, a prokaryotic promoter is employed for use with in vitro transcription of a desired sequence. Prokaryotic promoters for use with many commercially available systems include T7, T3, and Sp6.

Table 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

| Promoter/Enhancer | References |
|---|---|
| Promoter and/or Enhancer | |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |

TABLE 2-continued

| Promoter/Enhancer | References |
|---|---|
| Promoter and/or Enhancer | |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

| Element | Inducer | References |
|---|---|---|
| Inducible Elements | | |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |

TABLE 3-continued

Inducible Elements

| Element | Inducer | References |
| --- | --- | --- |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | ElA | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | ElA, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (X1) collagen (Tsumaki, et al., 1998), INA dopamine receptor gene (Lee, et al., 1997), insulin-like growth factor II (Wu et al., 1997), human platelet endothelial cell adhesion molecule-1 (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome-scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

For expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively, an autonomously replicating sequence (ARS) can be employed if the host cell is yeast.

8. Selectable and Screenable Markers

In certain embodiments of the invention, the cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Host Cells

As used herein, the terms "cell," "cell line," and "cell culture" may be used interchangeably. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector, expression of part or all of the vector-encoded nucleic acid sequences, or production of infectious viral particles. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either an eukaryotic or prokaryotic host cell, particularly one that is permissive for replication or expression of the vector.

C. Expression Systems

Numerous expression systems exist that comprise at least all or part of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM from CLONTECH®.

Other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REx™ (tetracycline-regulated expression) System, an inducible mammalian expression system that uses the full-length CMV promoter. The Tet-On™ and Tet-Off™ systems from CLONTECH® can be used to regulate expression in a mammalian host using tetracycline or its derivatives. The implementation of these systems is described in Gossen et al., 1992 and Gossen et al., 1995, and U.S. Pat. No. 5,650,298, all of which are incorporated by reference.

INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

D. Introduction of Nucleic Acids into Cells

In certain embodiments, a nucleic acid may be introduce into a cell in vitro for production of polypeptides or in vivo for immunization purposes. There are a number of ways in which nucleic acid molecules such as expression vectors may be introduced into cells. In certain embodiments of the invention, the expression vector comprises a GBV-C infectious particle or engineered vector derived from a GBV-C genome. In other embodiments, an expression vector known to one of skill in the art may be used to express a segment of a GBV-C nucleic, which may be translated into a GBV-C polypeptide or peptide. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

"Viral expression vector" is meant to include those vectors containing sequences of that virus sufficient to (a) support packaging of the vector and (b) to express a polynucleotide that has been cloned therein. In this context, expression may require that the gene product be synthesized. A number of such viral vectors have already been thoroughly researched, including adenovirus, adeno-associated viruses, retroviruses, herpesviruses, and vaccinia viruses.

Delivery may be accomplished in vitro, as in laboratory procedures for transforming cells lines, or in vivo or ex vivo, as in the treatment of certain disease states. One mechanism for delivery is via viral infection where the expression vector is encapsidated in an infectious viral particle. Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), liposome (Ghosh and Bachhawat, 1991; Kaneda et al., 1989) and receptor-mediated transfection (Wu and Wu, 1987; Wu and Wu, 1988). Some of these techniques may be successfully adapted for in vivo or ex vivo use.

In certain embodiments, the nucleic acid encoding a gene or genes may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression vector is delivered to a cell and where in the cell the nucleic acid remains is dependent on the type of expression vector employed.

Transfer of a nucleic acid molecule may be performed by any of the methods mentioned above which physically or chemically permeabilize the cell membrane. This is particularly applicable for transfer in vitro, but it may be applied to in vivo use as well.

IV. GBV-C Related Immunotherapy

Embodiments of the invention include various compositions and methods for stimulating, supplementing or enhancing the immune system of a subject that has or may be exposed to HIV. Immunotherapy in general is a treatment to stimulate, enhance, or restore the ability of the immune system to fight infection and disease. Immunotherapy is thus any form of treatment that uses the immune system to fight infection and disease or to protect the body from some of the side effects of treatment. Examples include active immunization, passive immunization, and adoptive immunotherapies.

Immunoglobulins typically mediate humoral immunity by attaching to foreign antigens and activating effector modalities (e.g., complement, granulocytes, cytotoxic T-cells, etc.) to destroy and clear the antigens and also by passive inactivation, exclusion or immobilization of pathogens. Each of the five Ig isotypes possesses its own spectrum of effector systems with which it interacts via its Fc domain. The constant region isotype of the antibody is determined following T-cell mediated, Ig class-switching which endows a given antibody with the specific effector modalities of the new isotype. Administration and/or elicitation of antibodies to GBV-C derived peptides, in particular GBV-C E2, may be used as a therapeutic in various immunotherapies.

A. Passive Immunotherapy Related to Anti-GBV-C Antibodies or Binding Agents

Purified or partially purified anti-GBV-C antibodies or binding agents may be administered to a subject for prophylatic or therapeutic treatment of HIV. Passive immunization has been administered for several bacterial infections including pneumococcal pneumonia and H. influenza pneumonia. In pneumococcal disease it was essential to identify the infecting serotype and obtain the appropriate type specific antiserum. The problems that arose from using horse serum and the difficulty in precisely defining the serotype led to the abandonment of this procedure as soon as antibiotic therapy was introduced into clinical medicine.

In recent years, passive immunotherapy has been used for several viral diseases such as hepatitis A, hepatitis B, polio, etc., and the use of intravenous X-globulin has grown as its applications have expanded. There have been several clinical trials with human monoclonal antibodies in various infectious diseases that document not only efficacy but also safety. It is contemplated therefore, that antibodies to GBV-C derived epitopes that have similar structural attributes to an infective pathogen, such as HIV, may be effective in either preventing infections or in actual therapy.

Although the bulk of contemporary opinion in virology and immunology supports the prevailing paradigm that immunity to the human immunodeficiency virus is largely cellular in nature, a significant body of evidence in vaccine studies in animals suggest a pivotal role for the humoral immune system (Sawyer et al., 1990, Moore et al., 1991). In chronic viral infections, antibodies may be critical at certain stages. As such, antibodies may play a crucial role in the control of HIV-1 infections. In particular, through the use of the present invention HIV may be inhibited in its ability to infect the body, or at least the reduce the level of infection or replication.

B. Active Immunotherapy Related to GBV-C Antigens

Certain embodiments of the invention include the vaccination of a subject with an antigen derived from a GBV-C protein, in particular a GBV-C envelope protein, for the therapeutic or prophylactic treatment of HIV. In certain embodiments, the antigen can be all or part of the GBV-C E2 polypeptide or mimcs thereof. Appropriate mimetics may be designed base on secondary or tertiary structure of a protein or peptide. This vaccination elicits the production of antibodies, i.e. GBV-C and HIV binding agents.

In particular aspects, anti-HIV properties may be illicited by expression or over-expression of a GBV-C antigen by an attenuated GBV-C viral vector. Anti-HIV properties will typically results in the modification of an HIV infection or the sensitivity to such an infection. Anti-HIV properties include, but are not limited to, delaying or slowing propagation of HIV; reducing viral load; reducing viral spread; reducing or limiting the severity of secondary pathologies, such as opportunistic infections and the like; preventing or reducing the probability of infection; neutralizing HIV particles; or competing with HIV binding sites on cells and in tissues and organs of a person exposed to HIV.

Active immunotherapy involves immunization of a subject to enhance existing or to elicit novel pathogen-specific immune responses, i.e., an HIV immune response, and, for example, provide systemic anti-pathogen immunity. Immunotherapeutic vaccination is the concept of inducing or enhancing immune responses of the subject to antigenic determinants that are uniquely expressed or expressed at increased levels on pathogens or cells infected by pathogens. Antigenic determinants may be in the form of peptides, polypeptides, attenuated pathogens, and the like.

The immune response is the way the body defends itself against microorganisms, viruses, and other potentially harmful substances or organisms. Antigens are typically molecules (usually proteins) on the surface of cells, viruses, fungi, bacteria, and some non-living substances such as toxins, chemicals, drugs, and foreign particles. The immune system recognizes and destroys substances containing these antigens.

The immune response may be an active immune response. Active immunity develops when the body is exposed to various antigens (antigenic epitopes), such as those described herein. It involves lymphocytes, of which there are 2 main groups, B-lymphocytes, and T lymphocytes. B lymphocytes (also called B cells) produce antibodies. Antibodies attach to a specific antigen and make it easier for the phagocytes to destroy the antigen. T lymphocytes (T cells) attack antigens directly, and some T lymphocytes provide control of the immune response. B cells and T cells develop that are specific for an antigen type. When a subject is exposed to a different antigen, different B cells and T cells are formed.

1. B Cells

B cells are a type of lymphocyte. The B cell produces antibodies that bind antigens. Each B cell is programmed to make a specific antibody. When a B cell encounters its antigen (along with collaborating T cells and accessory cells), it gives rise to many large plasma cells. Every plasma cell is a factory for producing antibody. Each of the plasma cells descended from a given B cell (which are all members of the same family, or clone) manufactures millions of identical antibody molecules and pours them into the bloodstream.

A given antibody has an affinity for a particular antigen. The antibody-antigen interaction marks the antigen or the cell displaying the antigen for destruction. After the human body has recovered from a disease, B-cells produce memory cells that attack the disease-causing organism if it invades again. This second response is much quicker than the first, thus preventing symptoms of the disease from occurring. The second phase involves the formation of the memory B-cell pool and seeding of long-lived plasma cells to the bone marrow. Plasma cells are terminally differentiated and do not give rise to memory cells.

Development of memory T cells (CD4 and CD8) may occur after activation, cells differentiate into effector T cells. Memory T cells may be generated from effector T cells. There may be two subsets of memory cells: quiescent, central memory cells that recirculate from blood to secondary lymphoid organs, and effector memory cells that migrate through tissues and deliver a very rapid response on reactivation with antigen.

2. Cytotoxic T Lymphocytes

In certain embodiments, T-lymphocytes are activated by contact with an antigen-presenting cell that is in contact with an antigen of the invention.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secrete various lymphokines that are crucial for the activation of B cells, T cytotoxic cells, macrophages, and other cells of the immune system. In contrast, a T cytotoxic cell that recognizes an antigen-MHC complex proliferates and differentiates into an effector cell called a cytotoxic T lymphocyte (CTL). CTLs eliminate cells of the body displaying antigen, such as virus-infected cells and tumor cells, by producing substances that result in cell lysis.

CTL activity may be assessed in freshly isolated peripheral blood mononuclear cells (PBMC), in a phytohaemaglutinin-stimulated IL-2 expanded cell line established from PBMC (Bernard et al., 1998) or by T cells isolated from a previously immunized subject and restimulated for 6 days with dendritic cells infected with an adenovirus vector containing antigen using standard 4 hr $^{51}$Cr release microtoxicity assays. One type of assay uses cloned T-cells. Cloned T-cells have been tested for their ability to mediate both perforin and Fas ligand-dependent killing in redirected cytotoxicity assays (Simpson et al., 1998). The cloned cytotoxic T lymphocytes displayed both Fas- and perforin-dependent killing. An in vitro dehydrogenase release assay has been developed that takes advantage of a fluorescent amplification system (Page et al., 1998). This approach is sensitive, rapid, and reproducible and may be used advantageously for mixed lymphocyte reaction (MLR). It may easily be further automated for large scale cytotoxicity testing using cell membrane integrity, and is thus considered in the present invention. In another fluorometric assay developed for detecting cell-mediated cytotoxicity, the fluorophore used is the non-toxic molecule alamarBlue (Nociari et al., 1998). The alamarBlue is fluorescently quenched (i.e., low quantum yield) until mitochondrial reduction occurs, which then results in a dramatic increase in the alamarBlue fluorescence intensity (i.e., increase in the quantum yield). This assay is reported to be extremely sensitive, specific and requires a significantly lower number of effector cells than the standard $^{51}$Cr release assay.

In certain aspects, T helper cell responses can be measured by in vitro or in vivo assay with peptides, polypeptides, or proteins. In vitro assays include measurement of a specific cytokine release by enzyme, radioisotope, chromaphore, or fluorescent assays. In vivo assays include delayed type hypersensitivity responses called skin tests, as would be known to one of ordinary skill in the art.

3. Antigen Presenting Cells

In general, the term "antigen presenting cell" can be any cell that accomplishes the goal of the invention by aiding the enhancement of an immune response (e.g., from the T-cell or -B-cell arms of the immune system) against an antigenic composition of the present invention or a heterologous antigen or a immunologically functional equivalent. Such cells can be defined by those of skill in the art, using methods disclosed herein and in the art. As is understood by one of ordinary skill in the art (see for example Kuby, 1993, incorporated herein by reference), and used in certain embodiments, a cell that displays or presents an antigen normally or preferentially with a class II major histocompatibility molecule or complex to an immune cell is an "antigen presenting cell." In certain aspects, a cell (e.g., an APC cell) may be fused with another cell, such as a recombinant cell or a tumor cell that expresses the desired antigen. Methods for preparing a fusion of two or more cells is well known in the art, such as for example, the methods disclosed in Goding, pp. 65-66, 71-74, 1986; Campbell, pp. 75-83, 1984; Kohler and Milstein (1975); Kohler and Milstein (1976), Gefter et al. (1977), each incorporated herein by reference. In some cases, the immune cell to which an antigen-presenting cell displays or presents an antigen to is a CD4+TH cell. Additional molecules expressed on the APC or other immune cells may aid or improve the enhancement of an immune response. Secreted or soluble molecules, such as for example, cytokines and adjuvants, may also aid or enhance the immune response against an antigen. Such molecules are well known to one of skill in the art, and various examples are described herein.

The dendritic cell (DC) is the cell type best suited for vaccine antigen delivery, as they are the most potent antigen presenting cells, effective in the stimulation of both primary and secondary immune responses (Steinman, 1999; Celluzzi and Falo, 1997). It is contemplated in the present invention that the exposure of dendritic cells with a GBV-C vaccine of the invention, will elicit a potent immune response specific for the vaccine or vaccine vector of the present invention. A more detailed description of vaccines is provided below.

C. Adoptive Immunotherapy Related to GBV-C Antigens

In various embodiments of the invention, it is contemplated that the antigens or anti-idiotypic antibodies may be used to stimulate autologous or heterologous immunocompetent cells for the treatment of HIV. Adoptive immunotherapy is a technique that involves either removing immunocompetent cells from the body, artificially increasing the number, and returning them to the body; or artificially altering target cells to make them more immunogenic.

Typical adoptive immunotherapy involves the administration of immunologically active cells to an individual for providing a beneficial immunological effect such as reduction or control of viral infections. The immunologically active cells are typically taken by venipuncture or leukophoreses either from the individual to be treated, termed autologous treatment, or from another individual, termed an allogeneic or heterologous treatment. The lymphocytes are then cultured to increase their number and to activate their therapeutic activity, and then infused back into the patient. Thus, the majority of conventional efforts in adoptive immunotherapy are typically directed at expanding cell numbers in vitro followed by infusion back into the patient.

Immunocompetent cells that may be used in adoptive immunotherapy are T lymphocytes. A method for the activation of T lymphocytes to generate T-activated killer cells (T-AK) has been described as taking lymphocytes by leukophoresis or from peripheral blood, and stimulating said cells with a monoclonal antibody (MAb) to a T cell surface receptor such as anti-CD3 (soluble or solid phase bound). The T cells can be stimulated with or without the addition of one or more cytokines such as IL-2. Alternatively, T cells can be purified before stimulation with the MAb to a surface receptor. Experimentation with T-AK cells has demonstrated that $CD8^+$ cells are responsible for the non-MHC restricted cytolytic activity seen in these cultures (Anderson et al., 1989; Loeffler et al., 1991). The ability of IL-2 to expand T lymphocytes having immune reactivity and the ability to lyse fresh autologous, syngeneic, or allogeneic natural killer (NK) cell-resistant tumor cells, but not normal cells, has resulted in the development of cell transfer therapies, such as autologous adoptive immunotherapy. Immunocompetent cells may include T lymphocytes, dendritic cells, and the like.

V. Anti-GBV-C Antibodies or Binding Agents

Embodiments of the invention may include polypeptides in the form of antibodies, single chain antibodies and the like that bind various GBV-C polypeptides, peptides, or derivatives thereof. Means for preparing and characterizing antibodies are well known in the art (see, e.g., Harlow and Lane, Antibodies: A Laboratory Manual, Cold Spring Harbor Laboratory, 1988; and Humphreys and Glover, 2001, each of which is incorporated herein by reference).

A. Anti-GBV-C Antibody Generation

The present invention provides therapeutic uses for anti-GBV-C antibodies. In some embodiments, monoclonal antibodies as well as polyclonal antibodies against GBV-C antigens may be used effectively in preventive and therapeutic treatment of HIV. Thus, the present invention is directed to anti-GBV-C antibody/antibodies that bind a GBV-C protein, polypeptide, or peptide, and attenuate HIV virus infectivity or replication. In particular, antibodies that bind a GBV-C envelope protein, polypeptide, or peptide are contemplated. In particular embodiments, antibodies that bind a GBV-C E2 protein, polypeptide, or peptide, as described herein, are contemplated. The invention also contemplates the use of a biologically functional equivalent of an anti-GBV-C antibody or a GBV-C antigen. The term "GBV-C protein/peptide/polypeptide" or "GBV-C antigen" is used herein to refer to a GBV-C protein, polypeptide or peptide, irrespective of whether it occurs naturally, is purified, is partially purified, or is produced by recombinant DNA methods, fusion-protein methods, protein synthesis methods or is a biological functional equivalent thereof.

A biologically functional equivalent is molecule where modifications and/or changes may be made in the structure of the polynucleotides encoding and/or the protein molecule, while obtaining molecules having similar or improved characteristics. In context of this invention, the molecule may be either a GBV-C antigen or an anti-GBV-C antibody. The biological functional equivalent may comprise a polynucleotide that has been engineered to contain distinct sequences while at the same time retaining the capacity to encode a "wild-type" or a functional polypeptide or peptide. This can be accomplished through the degeneracy of the genetic code, i.e., the presence of multiple codons, which encode for the same amino acids. Methods for preparing such equivalents are well known in the art.

The term "antibody" is used to refer to any antibody-like molecule that has an antigen binding region, and includes antibody fragments such as Fab', Fab, F(ab')$_2$, single domain antibodies (DABs), Fv, scFv (single chain Fv or single chain antibodies), chimeras and the like. Methods and techniques of producing the above antibody-based constructs and fragments are well known in the art (U.S. Pat. Nos. 5,889,157; 5,821,333; 5,888,773, each specifically incorporated herein by reference).

1. Polyclonal Antibodies

A polyclonal antibody typically is prepared by immunizing an animal with an immunogenic composition (comprising a GBV-C antigen, for example) and collecting antisera from that immunized animal. A wide range of animal species can be used for the production of antisera. Typically, the animal used for production of anti-antisera is a rabbit, a mouse, a rat, a hamster, a guinea pig, or a goat. Because of the relatively large blood volume of rabbits, a rabbit is a preferred choice for production of polyclonal antibodies.

As well known in the art, a given composition may vary in its immunogenicity. It is often necessary therefore to boost the host immune system, as may be achieved by coupling a peptide or polypeptide immunogen to a carrier. Exemplary carriers are keyhole limpet hemocyanin (KLH) and bovine serum albumin (BSA). Other proteins such as ovalbumin, mouse serum albumin, rabbit serum albumin, bovine thyroglobulin, or soybean trypsin inhibitor can also be used as carriers. Means for conjugating a polypeptide to a carrier protein are also well known in the art. Exemplary methods of conjugation include glutaraldehyde, m-maleimidobencoyl-N-hydroxysuccinimide ester, carbodiimyde, and bis-biazotized benzidine. Other bifunctional or derivatizing agent may also be used for linking, for example maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous, and intraperitoneal). The production of polyclonal antibodies may be monitored by sampling blood of the immunized animal at various points following immunization.

A second, booster injection, also may be given. The process of boosting and titering is repeated until a suitable titer is achieved. When a desired level of immunogenicity is obtained, the immunized animal can be bled and the serum isolated and stored, and/or the animal can be used to generate mAbs.

2. Monoclonal Antibodies

A "monoclonal antibody" refers to homogenous populations of immunoglobulins that are capable of specifically binding to a GBV-C protein. It is understood that the GBV-C protein or peptide, as described herein, may have one or more antigenic determinants. The antibodies of the invention may be directed against one or more of these determinants.

Monoclonal antibodies (mAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified GBV-C antigen protein, polypeptide, or peptide. The immunizing composition is administered in a manner effective to stimulate antibody-producing cells.

The methods for generating mAbs generally begin along the same lines as those for preparing polyclonal antibodies. Rodents such as mice and rats are preferred animals, however, the use of rabbit, sheep, goat, monkey cells is also possible. The use of rats may provide certain advantages (Goding, 1986, pp. 60-61), but mice are preferred, with the BALB/c mouse being most preferred. The BALB/c mouse is most routinely used and generally gives a higher percentage of stable fusions.

The animals are injected with antigen, generally as described above. Following immunization, somatic cells with the potential for producing antibodies, specifically B-lymphocytes (B-cells), are selected for use in the mAb generating protocol. These cells may be obtained from biopsied spleens or lymph nodes. Spleen cells and lymph node cells are preferred, the former because they are a rich source of antibody producing cells that are in the dividing plasmablast stage.

Often, a panel of animals will have been immunized and the spleen of animals with the highest antibody titer will be removed. The spleen lymphocytes are obtained by homogenizing the spleen with a syringe.

The antibody-producing B-lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984; each incorporated herein by reference). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bu1; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant-cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (hypoxanthine-aminopterin-thymidine (HAT) medium). Where azaserine is used, the media is supplemented with hypoxanthine. One preferred selection medium is HAT. Only cells capable of operating nucleotide salvage pathways are able to survive in HAT medium.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple, and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific mAb produced by the fused cell hybrid. The body fluids of the animal, such as serum or ascites fluid, can then be tapped to provide mAbs in high concentration.

The individual cell lines could also be cultured in vitro, where the mAbs are naturally secreted into the culture medium from which they can be readily obtained in high concentrations.

mAbs produced by either means may be further purified, if desired, using filtration, centrifugation, and various chromatographic methods such as FPLC or affinity chromatography. Fragments of the mAbs of the invention can be obtained from the purified mAbs by methods that include digestion with enzymes, such as pepsin or papain, and/or by cleavage of disulfide bonds by chemical reduction. Alternatively, mAb fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, or prom human cells derived from non-immunized individuals, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. A second advantage of monoclonal antibody production by screening recombinant libraries is the lack of need for immunization and a third is the ability to produce totally human monoclonal antibodies. Two commercially available anti-GBV-C E2 monoclonal antibodies have been tested for HIV-inhibitory effects on an R5 HIV strain. The M6 (Roche) was the best, but all three inhibited HIV. This was done in duplicate, and is similar to results seen in another previous experiment. The Roche monoclonal antibody has been studied for binding to E2 protein by pepscan. The antibody recognizes a linear epitope found on two overlapping peptides representing the GBV-C E2 protein. Thus, the epitope may be contained in a 9 amino acid sequence FYEPLVRRC (SEQ ID NO:8). This amino acid may be an HIV disease-modifying immunogen (Vaccine). The peptide may be used to inhibit HIV (as a prototype drug), and induce anti-HIV antibodies (as a vaccine).

Antibodies from Roche are described in Tacke et al. (1997) and Schmolke et al. (1998). For a description of epitope mapping studies see Schmolke et al. (1998). A "BD" and "VS" antibodies are commercially available monoclonal antibodies against GBV-C E2 sold by Biodesign and Virostat, respectively. Other Roche antibodies may also demonstrate these same affects, M13, and M30.

3. Humanized Anti-GBV-C Antibodies

In certain embodiments of the invention, anti-GBV-C antibodies may be humanized for therapeutic purposes. Humanized mAbs are antibodies of animal origin that have been modified using genetic engineering techniques to replace constant regions and/or variable region framework sequences with human sequences, while retaining the original antigen specificity. Such antibodies can also include a humanized heavy chain associated with a donor or acceptor unmodified light chain or a chimeric light chain, or vice versa. Such antibodies are commonly derived from rodent antibodies, for example, the murine Ab of the present invention. Rodent derived antibodies may demonstrate a specificity against human antigens and are generally useful for in vivo therapeutic applications. This strategy reduces the host response to the foreign antibody and allows selection of the human effector functions.

The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). "CDRs" are defined as the complementarity determining region amino acid sequences of an antibody. CDRs are contained within the hypervariable regions of immunoglobulin heavy and light chains. CDRs provide the majority of contact residues for the binding of the antibody to the antigen or epitope. CDRs of interest in this invention are derived from donor antibody variable heavy and light chain sequences, and include functional fragments and analogs of the naturally occurring CDRs, which fragments and analogs also share or retain the same antigen binding specificity and/or neutralizing ability as the donor antibody from which they were derived. When combined into an intact antibody, the humanized immunoglobulins are substantially non-immunogenic in humans and retain substantially the same affinity as the donor immunoglobulin to the antigen, such as a protein or other compound containing an epitope.

Generally, a humanized antibody has one or more amino acid residues introduced into it from a source that is non-human. These non-human amino acid residues are often referred to as "import" residues, which are typically taken from an "import" variable domain. A humanized antibody is one in which only the antigen-recognized sites, or complementarity-determining hypervariable regions (CDRs) are of non-human origin, whereas all framework regions (FR) of variable domains are products of human genes.

Humanization can be essentially performed following the method of Winter and co-workers (Jones et al., 1986; Riechmann et al., 1988; Verhoeyen et al., 1988), by substituting rodent CDRs or CDR sequences for the corresponding sequences of a human antibody. Accordingly, such "humanized" antibodies are chimeric antibodies, wherein less than an intact human variable domain has been substituted by the corresponding sequence from a non-human species. In practice, humanized antibodies are typically human antibodies in which some CDR residues and possibly some framework region (FR) residues are substituted by residues from analogous sites in rodent antibodies.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations and U.S. Pat. No. 4,867,973 which describes antibody-therapeutic agent conjugates.

U.S. Pat. No. 5,565,332, which incorporated herein by reference, describes methods for the production of antibodies, or antibody fragments, which have the same binding specificity as a parent antibody, but have increased human characteristics. Humanized antibodies may be obtained by chain shuffling, perhaps using phage display technology. Human antibodies may also be produced by transforming B-cells with EBV and subsequent cloning of secretors as described by Hoon et al., (1993).

4. Human Anti-GBV-C Antibodies

Embodiments of the invention may use human monoclonal antibodies in compositions and methods described herein. Human mAbs can be made using a hybridoma method. Human myeloma and mouse-human heteromyeloma cell lines for the production of human mAbs have been described, for example, by Kozbor (1984), and Brodeur et al. (1987).

It is now possible to produce transgenic animals (e.g., mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge (Jakobovits et al., 1993).

Alternatively, phage display technology can be used to produce human antibodies and antibody fragments in vitro, from immunoglobulin variable (V) domain gene repertoires from unimmunized donors (McCafferty et al., 1990). According to this technique, antibody V domain genes are cloned in-frame into either a major or minor coat protein gene of a filamentous bacteriophage, such as M13 or fd, and displayed as functional antibody fragments on the surface of the phage particle.

Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats (Johnson et al., 1993). Several sources of V-gene segments can be used for phage display. A repertoire of V genes from unimmunized human donors can be constructed and antibodies to a diverse array of antigens (including self-antigens) can be isolated essentially following the techniques described by Marks et al. (1991), or Griffith et al. (1993).

In a natural immune response, antibody genes accumulate mutations at a high rate (somatic hypermutation). Some of the changes introduced will confer higher affinity, and B-cells displaying high-affinity surface immunoglobulin are preferentially replicated and differentiated during subsequent antigen challenge. This natural process can be mimicked by employing the technique known as "chain shuffling" (Marks et al., 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires has been described by Waterhouse et al. (1993), and the isolation of a high affinity human antibody directly from such large phage library is reported by Griffith et al. (1993).

5. Anti-GBV-C Antibody Conjugates

Antibody conjugates comprising a GBV-C antibody linked to another agent, such as but not limited to a therapeutic agent, a anti-viral agent, a detectable label, a cytotoxic agent, a chemical, a toxic, an enzyme inhibitor, a pharmaceutical agent, etc. form further aspects of the invention. Antibody conjugates may be used both in in vitro diagnostics and in a variety of immunoassays.

Certain antibody conjugates include may be for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art and is described, for example, in U.S. Pat. Nos. 3,817,837; 3,850,752; 3,939,350; 3,996,345; 4,277,437; 4,275,149 and 4,366,241, each incorporated herein by reference.

6. Single Chain Antibodies

The Fv portion of an antibody is a 26 kDa heterodimer consisting of the amino-terminal variable domains of the heavy and light chains, and is the smallest fragment to bear the antigen binding site. Genetically engineered single chain Fv (Fv) peptides have been synthesized by attaching the carboxyl terminus of one variable domain to the amino terminus of the other with a peptide linker. These Fv fragments have been shown to bind specific antigens, like the transferrin receptor, have been used to localize fusion proteins to targeted cells.

VI. Anti-HIV GBV-C Vaccines

The present invention includes methods for preventing the development of or treating AIDS in both infected and uninfected persons, as well as the elicitation or enhancement of an immune response. As such, the invention contemplates vaccines for use in active, passive, and adoptive immunization embodiments. Immunogenic compositions, proposed to be suitable for use as active vaccines, may be prepared from an infectious, conditionally replicative, or replication defective GBV-C nucleic acid. Immunogenic compositions may also be prepared from a recombinant expression construct or synthesized in a manner disclosed herein or is known in the art. Preferably the antigenic material is extensively dialyzed to remove undesired small molecular weight molecules and/or lyophilized for more ready formulation into a desired vehicle.

The present invention, in certain embodiments, involves the use of a GBV-C antigen, for example, and E2 antigen. The antigen may also be a fragment of a GBV-C virus protein, such as a peptide (discussed above). In a particular embodiment, the antigen is contemplated that contains the 9 amino acid sequence FYEPLVRRC (SEQ ID NO:8). In preferred embodiments, the antigen is contemplated to comprise the 13 amino acid LTGGFYEPLVRRC (SEQ ID NO:6). In more preferred embodiments, the antigen is contemplated to comprise the 17 amino acid sequence GGAGLTGGFYEPLVRRC (SEQ ID NO:7). This amino acid may be an HIV disease-modifying immunogen (vaccine) and/or induce anti-HIV antibodies (as a vaccine).

A. Carrier Molecules for Vaccination Against GBV-C Antigens

As is well known in the art, a given composition may vary in its immunogenicity. It is often necessary therefore to boost the host immune system, as may be achieved by coupling the heterologous polypeptide immunogen to a carrier. Exemplary carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

B. Adjuvants

As is also well known in the art, the immunogenicity of a polypeptide or peptide composition can be enhanced by the use of non-specific stimulators of the immune response, known as adjuvants. Suitable adjuvants include all acceptable immunostimulatory compounds, such as cytokines, toxins, or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-12 or genes encoding proteins involved in immune helper functions, such as B-7.

VII. Anti-HIV Therapies

In certain embodiments, therapeutic methods will include administering to a patient or subject a composition comprising an antigen or an antibody derived from a GBV-C polypeptide. In various embodiments, the treatment methods of the invention may be used in combination with other anti-HIV treatments, such as GBV-C infection as a therapeutic or preventative treatment for AIDS. For exemplary compositions and methods see PCT application WO 01/77157, which is incorporated herein by reference.

As a therapeutic measure, a binding agent that binds a GBV-C derived amino acid molecule can be used to reduce the severity or progression of AIDS, including the prevention of AIDS in HIV-infected individuals. A reduction in severity or progression of AIDS includes, but is not limited to, prevention of or a reduction in the severity, duration, or discomfort associated with the following conditions: prolonged and unexplained fatigue; swollen glands; prolonged fever; chills; excessive sweating; swollen gums and mouth lesions; sore throat; cough; shortness of breath; constipation; diarrhea; symptoms of well-known opportunistic infections; Kaposi sarcomas; skin rashes or lesions; loss of appetite or weight loss; malaise; headaches; speech impairment; muscle atrophy; memory loss; reduced cognitive functioning; swelling of the joints; joint stiffness or pain; cold intolerance; pain or tenderness in bones; energy level; anxiety, stress, and tension; groin lump; pruritus; genital sores; blurred or decreased vision; diplopia; light sensitivity; pain in chest, sides, back, muscle or stomach; and seizures.

As a preventative measure, a patient may be administered a pharmaceutically acceptable composition comprising a HIV neutralizing or attenuating binding agent derived from a GBV-C polypeptide. The anti-HIV GBV-C binding agent may be used in conjunction with infection of CD4+ T cells with GBV-C or a recombinant version of GBV-C to inhibit infection of these cells by HIV. Alternatively, treatment with the GBV-C compositions of the present invention may effect a combination of preventative and therapeutic treatments insofar as infection of other cells in an HIV-infected subject's body is prevented or attenuated.

Inhibition of AIDS progression may be demonstrated by reduction of detectable HIV in the HIV-infected subject; maintaining a CD4 count above 200 for a longer than average period of time; maintaining a normal T cell count; or maintaining normal p24 antigen. The term "therapeutic benefit" or "therapeutic effect" used throughout this application refers to anything that promotes or enhances the well-being of the subject with respect to the medical treatment of his/her condition, which includes treatment of HIV-infection (before the onset of AIDS), AIDS, as well as treatment of Hepatitis C. A list of nonexhaustive examples of this includes extension of the subject's life by any period of time; decrease or delay in the progression of AIDS (HIV, as described above) or Hepatitis C; decrease in viral load of HIV or HCV; decrease in HIV replication; clearance of HIV or HCV viremia reduced transmission of HCV or HIV; decrease in liver damage or complications; and a decrease in pain to the subject that can be attributed to the subject's condition.

A. Combination Therapies

Of course it is understood that the method of the present invention, particularly administration of agents that bind a GBV-C amino acid molecule as treatment for an HIV-infected subject, may also be used in combination with the administration of traditional therapies. Alternatively, the compositions of the present invention may be given in combination with treatment or prevention of hepatitis C, such as α-interferon. Some such therapies are described below.

In many clinical situations, it is advisable to use a combination of distinct therapies. Thus, it is envisioned that, in addition to the therapies described herein, one would also wish to provide to the patient more "standard" pharmaceutical anti-retroviral therapies. Examples of standard therapies are provided below.

Combinations may be achieved by administering to a patient a single composition or pharmacological formulation that includes both agents, or by administering to a patient two distinct compositions or formulations, at the same time, wherein one composition may include a GBV-C binding agent, GBV-C antigen, or expression construct encoding a binding agent or antigen, and the other includes the standard anti-retroviral therapy. Alternatively, a GBV-C based therapeutic may precede or follow the other treatment by intervals ranging from minutes to weeks. In embodiments where the other agent and GBV-C based therapeutic are administered separately to the patient, one would generally ensure that a significant period of time did not expire between the time of each delivery, such that the agent and GBV-C based therapeutic would still be able to exert an advantageously combined effect on the patient. In such instances, it is contemplated that one would administer to the patient both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6, or 7) to several weeks (1, 2, 3, 4, 5, 6, 7, or 8) lapse between the respective administrations.

It also is conceivable that more than one administration of a GBV-C based therapeutic agent will be desired. Various combinations may be employed, where a GBV-C based therapeutic is "A" and the other agent is "B," as exemplified below:

```
A/B/A  B/A/B  B/B/A  A/A/B  B/A/A  A/B/B  B/B/B/A

B/B/A/B  A/A/B/B  A/B/A/B  A/B/B/A  B/B/A/A

B/A/B/A  B/A/A/B  B/B/B/A  A/A/A/B  B/A/A/A

A/B/A/A  A/A/B/A  A/B/B/B  B/A/B/B  B/B/A/B
```

Other combinations are contemplated as well.

1. AZT

A well known, traditional therapy for the treatment of AIDS involves zovidovudine (AZT™ available from Burroughs Wellcome). This is one of a class of nucleoside analogues known as dideoxynucleosides which block HIV replication by inhibiting HIV reverse transcriptase. The anti-AIDS drug zidovudine (also known as AZT) may also be used in limited circumstances, mostly in combination with rifampin, as described by Burger et al. (1993).

The compositions and methods disclosed herein will be particularly effective in conjunction with other forms of therapy, such as AZT and/or protease inhibitors that are designed to inhibit viral replication, by maintaining desirable levels of white blood cells. This, in effect, buys the patient the time necessary for the anti-viral therapies to work.

2. HAART

New combination drug therapy has shown promising results in the treatment of HIV-infected patients. Treatment with potent anti-HIV drug combinations is referred to as "highly active anti-retroviral therapy" (HAART), and it has provided clinical improvement, longer survival, and improved quality of life for people infected with HIV during all four stages of HIV disease. Examples of HAART include a protease inhibitor (indinavir, nelfinavir, ritonavir, ritonavir/saquinavir, or saquinavir) combined with two nucleoside analogs (AZT/ddI, d4T/ddI, AZT/ddC, AZT/3TC, or d4T/3TC).

In many instances, it will be desirable to have multiple administrations of the inventive compositions and/or a vaccines, usually not exceeding six administrations or vaccinations, more usually not exceeding four vaccinations. In certain embodiments, one or more, usually at least about three administrations or vaccinations may be provided. The administrations or vaccinations will normally be at from two to twelve week intervals, more usually from three to five week intervals. Periodic boosters at intervals of 1-5 years, usually three years, will be desirable to maintain protective levels of the antibodies. The course of the immunization or treatment may be followed by standard antibody assays. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

The manner of application may be varied widely. Any of the conventional methods for administration of an antibody or vaccine are applicable. These are believed to include oral application on a solid physiologically acceptable base or in a physiologically acceptable dispersion, parenterally, by injection or the like. The dosage of the anti-GBV-C antibody or vaccine will depend on the route of administration and will vary according to the size of the host.

The anti-GBV-C binding agents, GBV-C infectious nucleic acids and/or GBV-C antigens of the invention may be formulated into a pharmaceutically acceptable composition, see below, or vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparation of binding agent that bind GBV-C sequences as active ingredients is generally well understood in the art by analogy, as exemplified by U.S. Pat. Nos. 6,479,243, 6,399,763, 5,714,153, 5,582,981, and 4,833,077, all incorporated herein by reference. The preparation of vaccines that contain GBV-C sequences as active ingredients is generally well understood in the art by analogy, as exemplified by U.S. Pat. Nos. 5,958,895, 6,004,799, and 5,620,896, all incorporated herein by reference.

VIII. Pharmaceutical Compositions and Routes of Administration

Pharmaceutical compositions, including the immunoglobulins for passive immunotherapy or antigens for active immunotherapy, are typically used for prophylaxis of susceptible individuals and for the treatment of infections. A discussion of passive and active immunity and immunizing agents may be found in Remington's Pharmaceutical Sciences, 1990. The immunity provided by passive immunization is typically not long lasting and the immunoglobulins provided leave the body tissues and fluids of the host within a comparatively short period of time, usually after one to two weeks, either by utilization by binding to the pathogen or by metabolism by the host's body. Thus, the administration of an antibody for passive immunity may be during the critical period immediately after or just prior to the predicted exposure to the pathogen or toxin such that the immunoglobulins are present when immunity is most urgently required.

The percentage of active compound in any pharmaceutical preparation is dependent upon both the activity of the compound, in this case binding of an antibody(ies) or other binding agent, and its concentration in the preparation. Typically, such compositions should contain at least 0.1% active compound. The percentage of the compositions and preparations may, of course, be varied and may conveniently be between about 2 to about 60% of the weight of the unit. The amount of active compounds in such therapeutically useful compositions is such that a suitable dosage will be obtained.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy injection is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, phenylmecuric nitrate, m-cresol, and the like. In many cases, it will be preferable to use isotonic solutions, for example, sugars or sodium chloride. Prolonged absorption of the injectable compositions can be brought about by the use in the compositions of agents delaying absorption, for example, aluminum monostearate, and gelatin.

Sterile injectable solutions are prepared by incorporating the active compounds in the required amount in the appropriate solvent with various of the other ingredients enumerated above, as required, followed by sterile filtration. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques that yield a powder of the active ingredient plus any additional desired ingredient from a previously sterile-filtered solution thereof.

The present invention contemplates GBV-C antigens, anti-GBV-C antibodies, and/or infectious GBV-C nucleic acid molecules as well as infectious nucleic acid molecules encoding, in some embodiments, a heterologous sequence, collectively "therapeutic GBV-C compositions". In some embodiments, pharmaceutical compositions are administered to a subject. Different aspects of the present invention involve administering an effective amount of an aqueous composition. In another embodiment of the present invention, therapeutic GBV-C compositions are administered to a subject to either prevent the infection by HIV or prevent the progression of HIV infection to development of AIDS. Additionally, such compounds can be administered in combination with treatment by HAART or by administration of AZT and/or other anti-HIV drugs or drug regiments. Though typically, anti-GBV-C agent or GBV-C antigens will be administered separately from medication. Such compositions will generally be dissolved or dispersed in a pharmaceutically acceptable carrier or aqueous medium. Those of skill in the art are well aware of how to apply antibodies or other binding agents, as well as gene delivery to in vivo and ex vivo situations.

The phrases "pharmaceutically acceptable" or "pharmacologically acceptable" refer to molecular entities and compositions that do not produce an adverse, allergic, or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention can be formulated for parenteral administration, e.g., formulated for injection via the intravenous, intramuscular, intrathoracic, sub-cutaneous, or even intraperitoneal routes. Administration by i.v. or i.m. are specifically contemplated.

The preparation of an aqueous composition that contains a compound or compounds that increase the expression of an MHC class I molecule will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The antibodies, binding agents, or other active compositions may be formulated as neutral or salt forms. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The course of the treatment may be followed by assays for antibodies against antigens. The assays may be performed by labeling with conventional labels, such as radionuclides, enzymes, fluorescers, and the like. Samples for assaying may be serum samples, or they may be obtained from any mucosal surface, or body fluid, such as saliva, sputum, vaginal wash, or expectoration. These assay techniques are well known and may be found in a wide variety of patents, such as U.S. Pat. Nos. 3,791,932; 4,174,384 and 3,949,064, as illustrative of these types of assays.

In certain embodiments, it may be desirable to provide a continuous supply of therapeutic compositions to the patient. For intravenous or intraarterial routes, this is accomplished by drip system. For various approaches, delayed release formulations could be used that provided limited but constant amounts of the therapeutic agent over and extended period of time. For internal application, continuous perfusion, for example with an anti GBV-C antibody, binding agent, antigen and/or a GBV-C viral vector which may or may not carry a heterologous nucleic acid segment may be preferred. This could be accomplished by catheterization followed by continuous administration of the therapeutic agent. The time period for perfusion would be selected by the clinician for the particular patient and situation, but times could range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, Remington's Pharmaceutical Sciences, 1990). Some variation in dosage will necessarily occur depending on the condition of the subject being treated. The person responsible for administration will, in any event, determine the appropriate dose for the individual subject.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Antibodies or other binding agents may be administered in a dose that can vary from 0.01, 0.05, 0.1, 0.5, 1, 5, 10, 20, 30, 40, 50, 60, 70, 80, 90, 100 mg/kg of weight to 50, 60, 70, 80, 90, 100, 110, 120, 130, 140, 150, 160, 170, 180, 190, 200 mg/kg of weight in one or more daily, weekly, monthly, or yearly administrations during one or various days, weeks, months, or years. The antibodies can be administered by parenteral injection (intravenous, intraperitoneal, intramuscular, subcutaneous, intracavity or transdermic). For viral vectors, one generally will prepare a viral vector stock. Depending on the kind of virus and the titer attainable, one will deliver 1 to 100, 10 to 50, 100-1000, or up to $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

In many instances, it will be desirable to have multiple administrations of the antibodies or other compositions of the invention. The compositions of the invention may be administered 1, 2, 3, 4, 5, 6, 7, 8, 9, 10, or more times. The administrations will normally be at from one to twelve week intervals, more usually from one to four week intervals. Periodic re-administration will be desirable with recurrent exposure to the pathogen (e.g., HIV). For example, an HIV positive mother would be re-inoculated prior to parturition from a second pregnancy.

Dosages commonly used for formulations that provide passive immunity are in the range of from 0.5 ml to 10 ml per dose, preferably in the range of 2 ml to 5 ml per dose. Repeated doses to deliver the appropriate amount of active compound are common. Both the age and size by weight of the recipient must be considered when determining the appropriate dosage of active ingredient and volume to administer.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular therapeutic substance.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

As used herein, the term in vitro administration refers to manipulations performed on cells removed from an animal, including, but not limited to, cells in culture. The term ex vivo administration refers to cells that have been manipulated in vitro, and are subsequently administered to a living animal. The term in vivo administration includes all manipulations performed on cells within an animal.

In certain aspects of the present invention, the compositions may be administered either in vitro, ex vivo, or in vivo. In certain in vitro embodiments, transcribed RNA from a GBV-C clone is transfected into PBMC using DEAE-dextran. The transduced cells can then be used for in vitro analysis, or alternatively for in vivo administration.

U.S. Pat. Nos. 4,690,915 and 5,199,942, both incorporated herein by reference, disclose methods for ex vivo manipulation of blood mononuclear cells and bone marrow cells for use in therapeutic applications.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: HIV Neutralization Assay

E2 antibody serum was studied for interactions with HIV in a virus neutralization assay. In one study (FIG. 1), a clinical R5 strain of HIV was incubated with a GBV-C RNA negative-E2 antibody negative serum (mock), with GBV-C E2 antibody positive-RNA negative serum (E2), GBV-C RNA positive-E2 negative serum (GBV-C), or a mixture of E2 and GBV-C sera for 1 hour at 37° C. prior to adding the mixture to PHA-IL-2 stimulated peripheral blood mononuclear cells (PBMCs). After infection, cells were washed, and media was collected daily for 3 days for testing for HIV p24 antigen (p24 Ag) in culture supernatant by ELISA. HIV p24 Ag was measured, and the percent inhibition determined by dividing the concentration present in the test sample by the HIV-mock infected control sample. The baseline HIV p24 Ag was determined using the "mock"-HIV mixture, and significant inhibition of HIV replication (as measured by p24 Ag production into culture supernatant fluids) was observed when E2-positive sera was mixed with HIV, although this inhibition declined each day. Similarly, when GBV-C RNA-positive sera (and GBV-C replication) was mixed with HIV, the HIV replication was inhibited to a greater extent than with E2 antiserum alone, and the mixture of E2 and GBV-C RNA positive sera gave the greatest extent of HIV inhibition.

Figure 2:
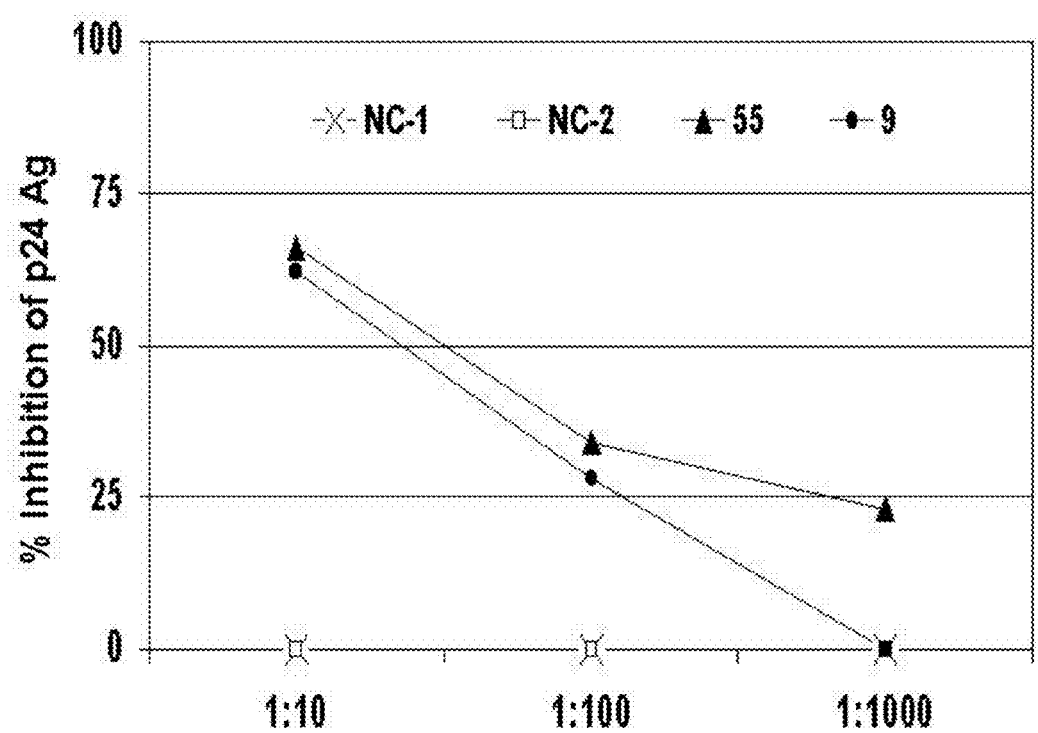
FIG. 2. Example of inhibition of HIV by two E2 antibody positive sera in a dose-dependent fashion; whereas, E2 antibody negative sera does not inhibit HIV.

Reproducibility was determined by performing additional studies. Two additional GBV-C E2 antibody positive (RNA negative) sera (isolates 55 and 9 respectively) and two E2 antibody negative (and RNA negative) sera (negative control sera 1 and 2) were studied for their ability to decrease replication of the R5 HIV strain. A clinical isolate was used for this study. In addition, diluted sera at 1:10, 1:100, and 1:1,000 were used to determine if there was a dose-response relationship between the concentration of serum and the extent of HIV inhibition. After washing the PBMCs, sera was maintained in the culture media throughout the experiment, and infections were monitored on day 3 for HIV p24 Ag production in culture supernatant. FIG. 2. Illustrates that HIV is inhibited by two E2 antibody positive sera in a dose-dependent fashion; whereas, E2 antibody negative sera do not inhibit HIV.

Example 2: HIV Neutralization Assay with Purified Antibody

Figure 3:
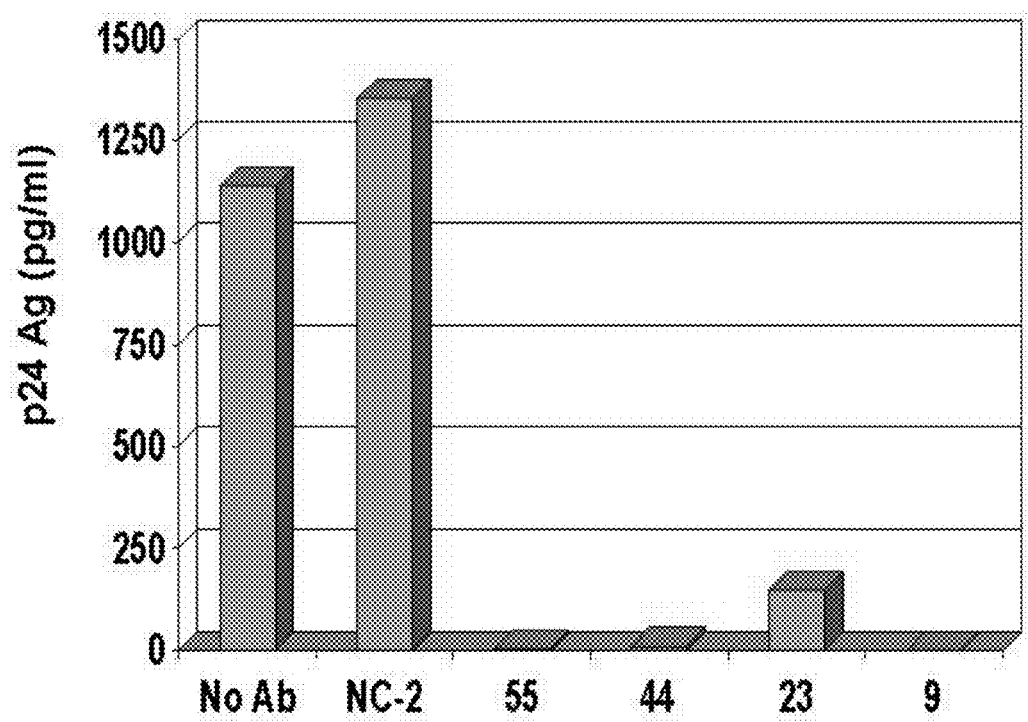
FIG. 3. IgG purified from E2 antibody positive sera inhibits HIV replication in PBMC cultures.
Figure 4:
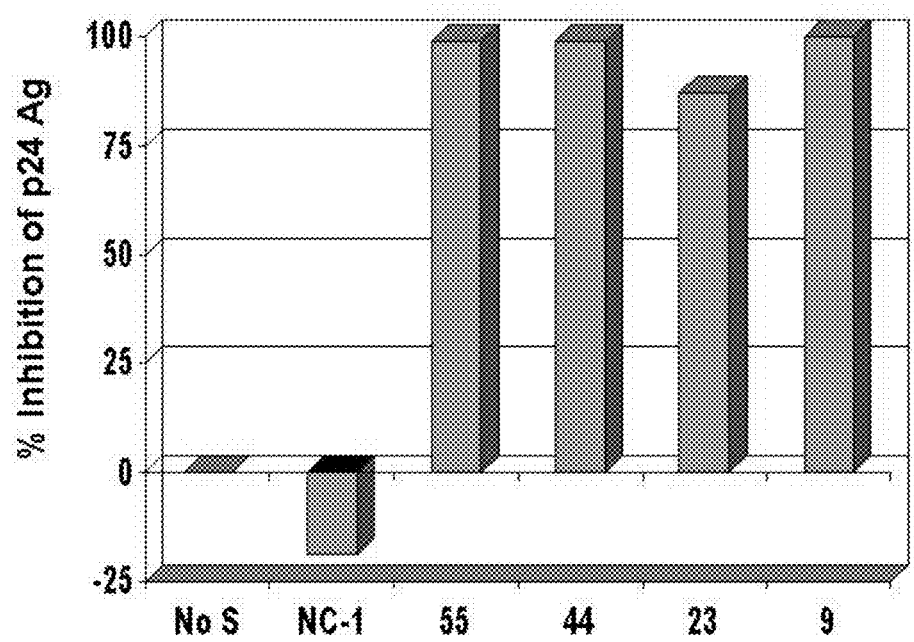
FIG. 4. IgG purified from E2 antibody positive sera inhibits HIV replication in PBMC cultures (same data shown in FIG. 3, but represents the data as percent inhibition in HIV p24 Ag in culture supernatant fluids).

To determine if the inhibitory substance in the GBV-C E2 antibody-positive sera was antibody, IgG from four E2 antibody-positive sera and two E2 antibody-negative sera were purified by protein G column chromatography. HIV was mixed with a "no antibody" control (No Ab), or with 5 µg/ml of an E2 antibody negative control (NC-2) or E2 positive controls. The mixtures were applied to PBMCs, and after washing the HIV inocula, the cognate IgGs were maintained in the culture media. The raw p24 Ag results are shown in FIG. 3, and the percent HIV p24 Ag inhibition is shown in FIG. 4.

Example 3: HIV Neutralization Assay on HIV Strain X4

Figure 5:
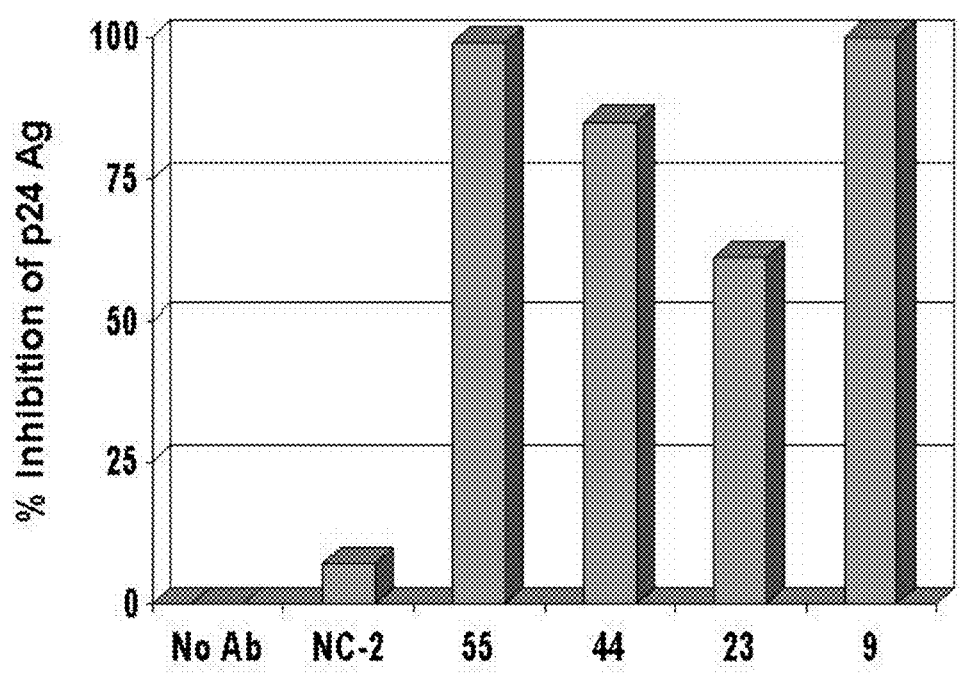
FIG. 5. GBV-C E2 antibody positive IgG inhibition of clinical X4 HIV strain.

Studies were performed to determine if E2 antibody-positive serum inhibited X4 strains of HIV. Using the same experimental design as used for FIGS. 3 and 4, IgG preparations from E2-negative and -positive IgG preparations were studied for their ability to inhibit a clinical X4 HIV strain in PHA-IL-2 PBMC cultures. Similar to the R5 strain, the X4 strain was inhibited by GBV-C E2-positive IgG, but not GBV-C E2-negative IgG (FIG. 5).

Since R5 viruses utilize CCR5 as their co-receptor, and X4 viruses utilize CXCR4 as their co-receptor, GBV-C E2 antibody inhibition indicates that they are cross-reacting with a conserved epitope on HIV that inhibits HIV replication, and that this epitope is on both co-receptor usage types of HIV. Since the epidemiological data indicates that E2 antibody is associated with prolonged survival in Germany, France, and the United States, this interaction has promise for HIV strains widely distributed worldwide.

Example 4: HIV Neutralization with Monoclonal Antibodies

Commercially available anti-GBV-C E2 monoclonal antibodies from Biodesign and Virostat, and one supplied by Roche were tested for HIV-inhibitory effects. Inhibition of an R5 HIV strain was detected when using all three antibodies, with M6 (Roche) being the best. Studies were performed in duplicate, and are similar to results seen in another previous study. The Roche monoclonal antibody binding to E2 protein has been studied using pepscan. M6 recognizes a linear epitope found on two overlapping peptides representing the GBV-C E2 protein. Thus, an epitope is contained in a 9 amino acid sequence of FYEPLVRRC (SEQ ID NO:8) or in a 17 amino acid sequence of GGAGLTGGFYEPLVRRC (SEQ ID NO:6). This amino acid sequence may be an HIV disease-modifying immunogen (vaccine).

Figure 6:
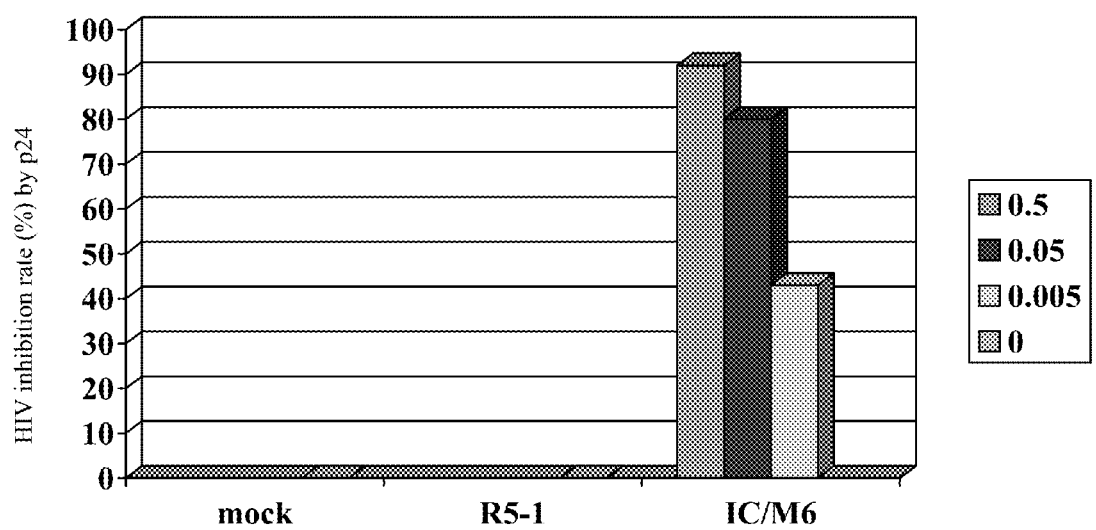
FIG. 6. The Roche M6 monoclonal antibody inhibits HIV-1 (R5 strain)

FIG. 6 demonstrates that the Roche M6 monoclonal antibody inhibits HIV-1 (R5 strain). HIV was mixed with M6 antibody or an isotype control antibody (range of concentrations, as shown) for 1 hr at 37° C., then added to PBMC cultures. Four hrs later, cells were washed, and media was added to cells (media containing either M6 or IC). Culture supernatants were collected on day 3 post-infection and HIV p24 antigen determined. Percent inhibition was determined by dividing the p24 antigen concentration in the M6 culture supernatant by the Isotype control p24 antigen concentration. This value was subtracted from 1, and the result was multiplied ×100.

Figure 7:
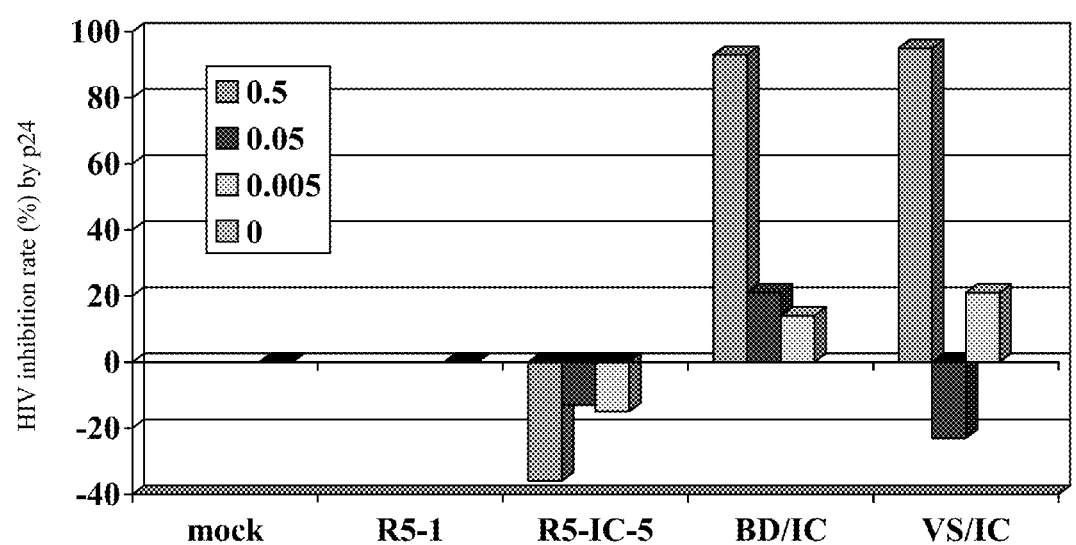
FIG. 7. The Biodesign (Saco, Me.) and Virostat (Portland, Me.) antibodies also inhibited HIV-1, although not as efficiently as M6.
Figure 8:
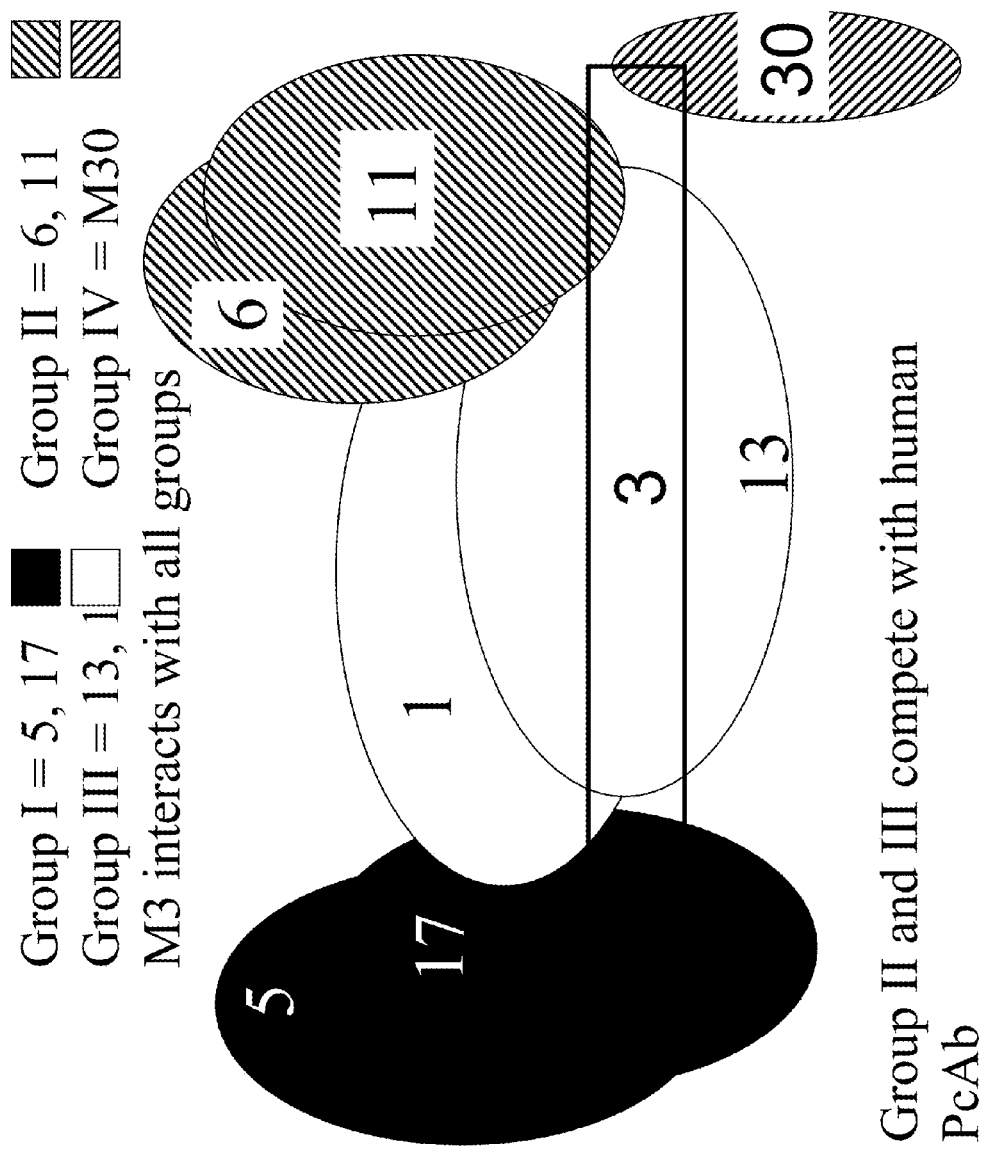
FIG. 8. A map of the epitopes identified by the Roche mAbs as described in Schmolke et al. (1998).
Figure 9:
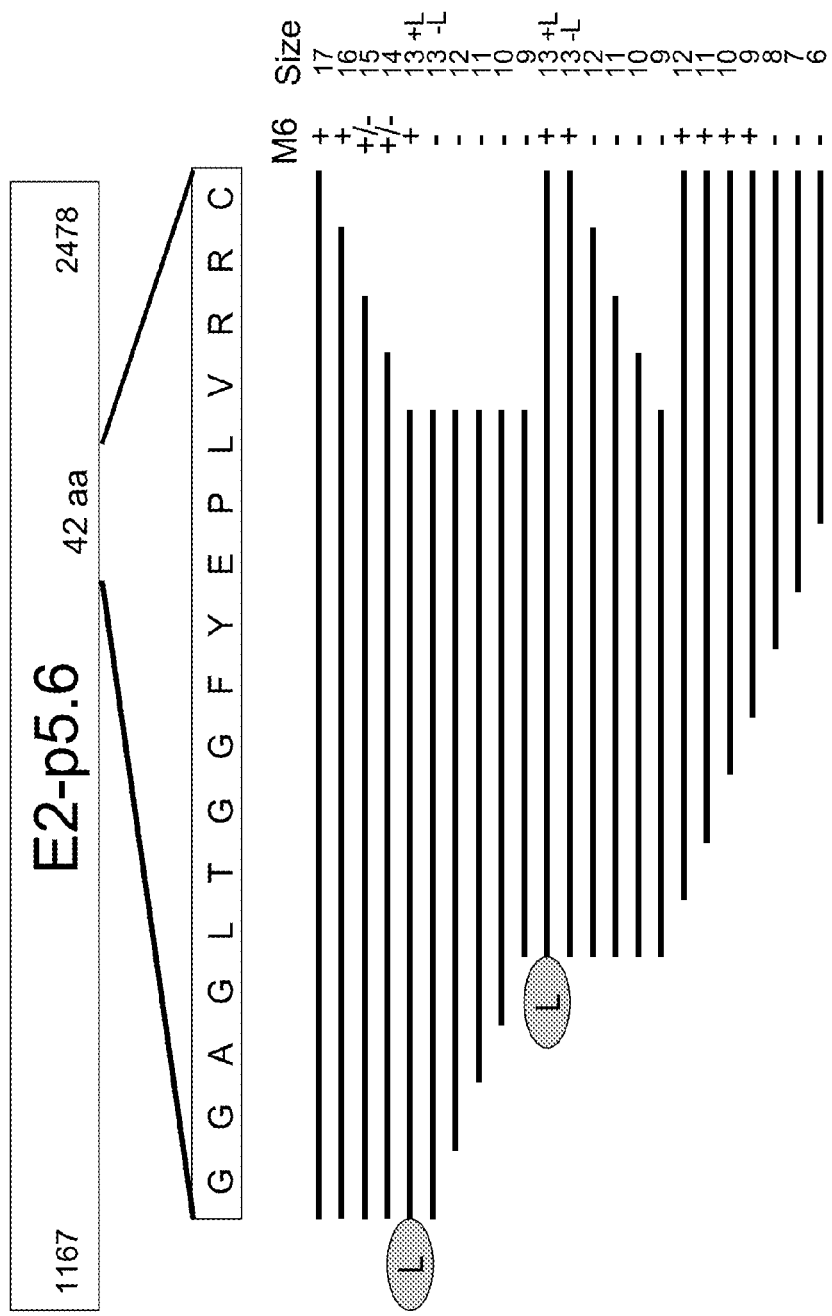
FIG. 9. A map of exemplary GBV-C epitopes (Peptide GGAGLTGGFY EPLVRRC (SEQ ID NO:6)).

FIG. 7 demonstrates that the biodesign and virostat antibodies also inhibited HIV-1, although not as efficiently as M6. FIG. 8 is a predicted map of the epitopes identified by the Roche mAbs as described in Schmolke et al. (1998). M3 inhibits all of the groups of antibodies. M6 was the only antibody to react with a linear peptide in a PEPSCAN analysis. Antibodies against this M6 epitope were found to not appear to be elicited during GBV-C infection.

Example 5: HIV Neutralization with Rabbit Sera

Figure 10:
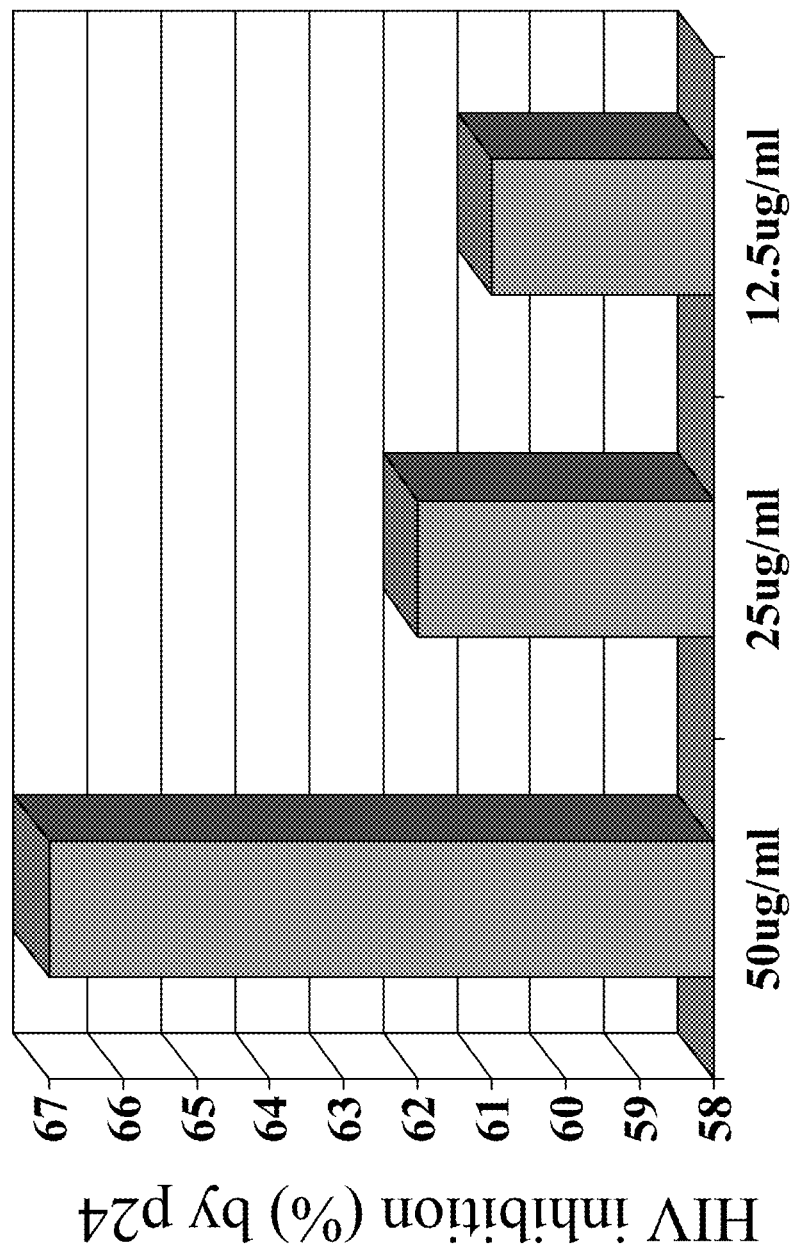
FIG. 10. Illustrates inhibition of HIV-R5 by 17-mer Rabbit serum day 3.
Figure 11:
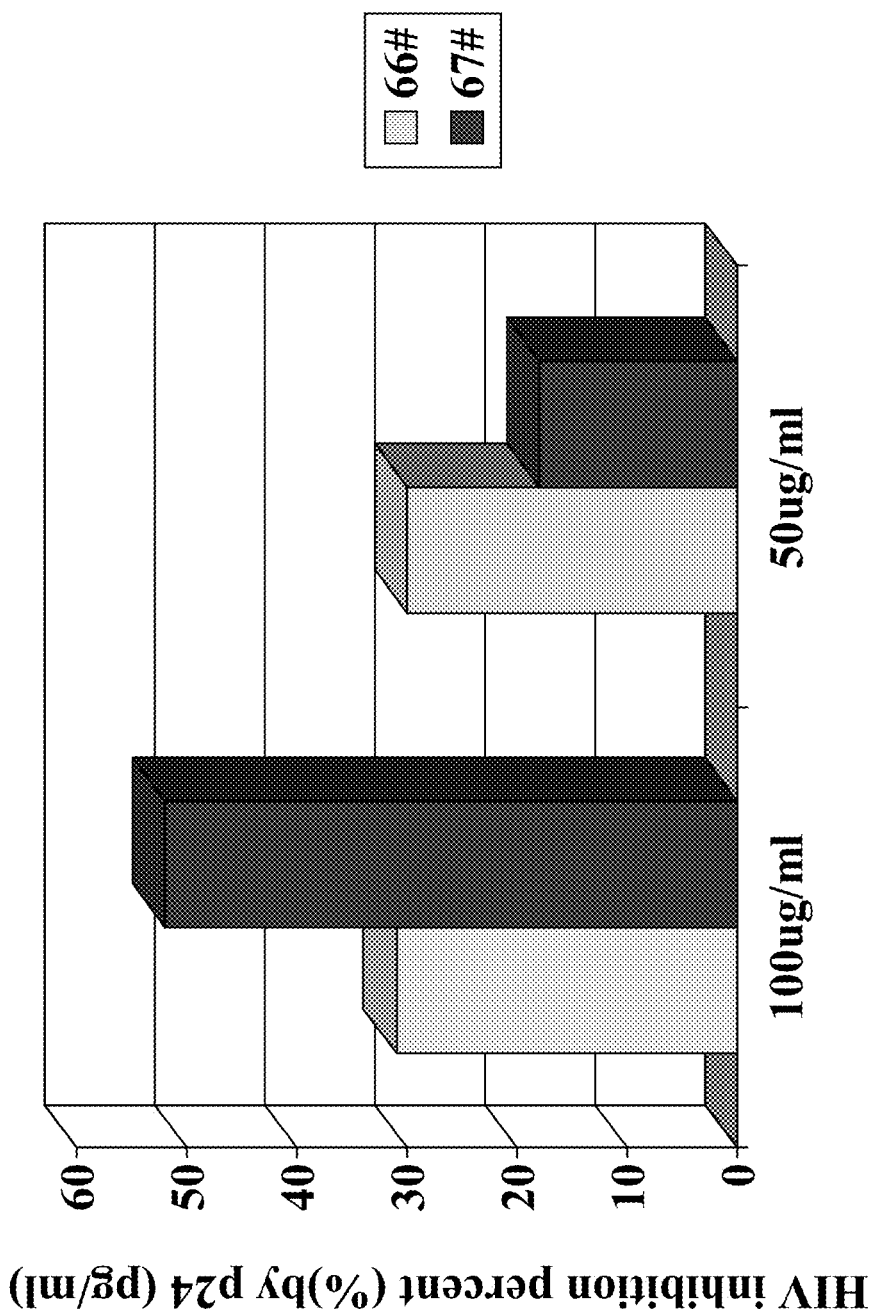
FIG. 11. Illustrates inhibition of HIV (X4) by Rabbit anti-peptide IgG day 2.
Figure 12:
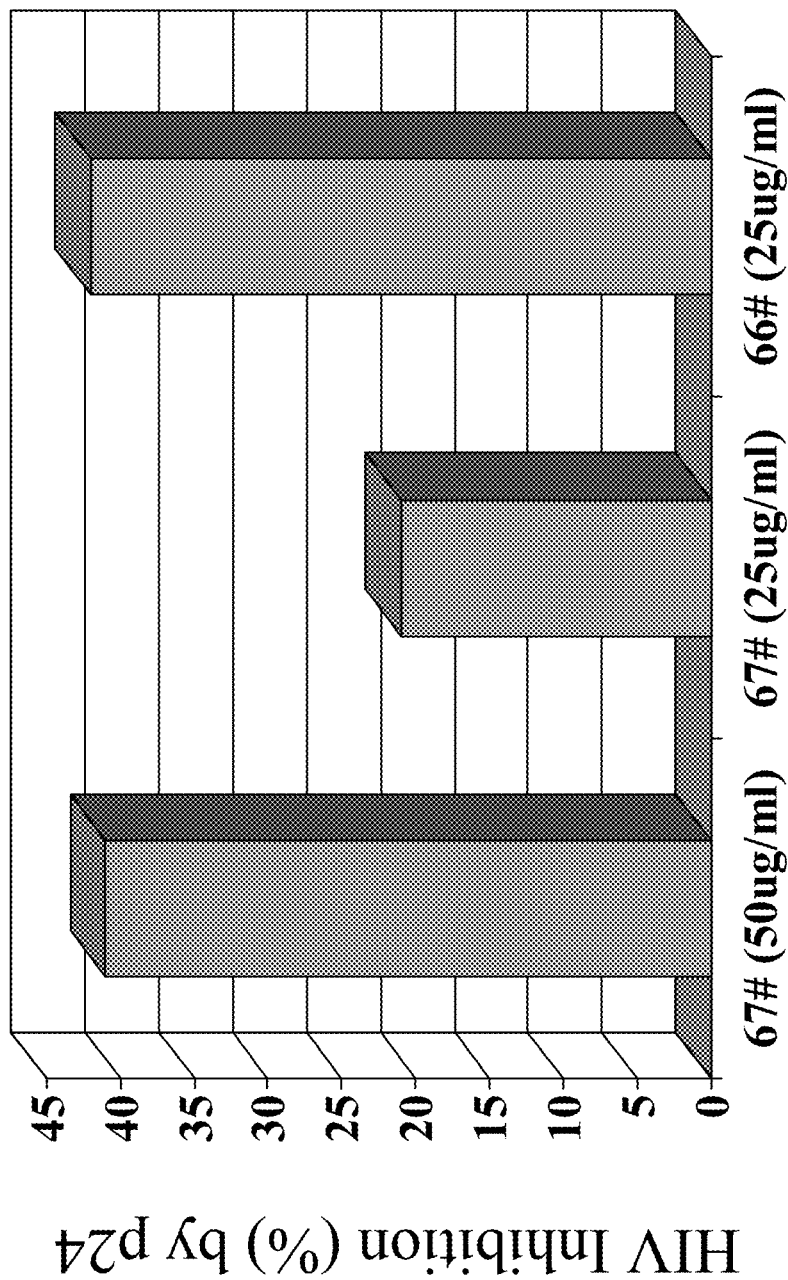
FIG. 12. Illustrates inhibition of HIV (X4) by 17-mer Rabbit serum day 3.

To determine if the peptide antigen shown to react with the anti-GBV-C E2 (M6) monoclonal antibody was antigenic and if it exhibited anti-HIV activity, the inventors conjugated the 17 amino acid peptide to KLH) and immunized 2 New Zealand White rabbits (commercially done by InVitrogen). IgG was purified from serum collected pre-immunization and at 8 weeks (following immunization and 2 boosts). Pre-immune and post-immune anti-GBV-C E2 peptide rabbit IgG was incubated with R5 and X4 HIV for 1 hour, and then added to primary PBMCs for 3 hours. Cells were then washed, and maintained in media containing either pre-immune or post-immune IgG. HIV production into culture supernatant was measured by p24 antigen, and the post-immune IgG reproducibly reduced HIV infectivity in both R5 and X4 viruses (FIGS. 10, 11, and 12). All experiments were performed in triplicate, and the reduction in p24 antigen levels by post-immune IgG were all statistically significant at the $P<0.05$ level. These studies demonstrate that anti-GBV-C E2 peptide antibody inhibits HIV.

Example 6: HIV Particle RIP Precipitation

Figure 13:
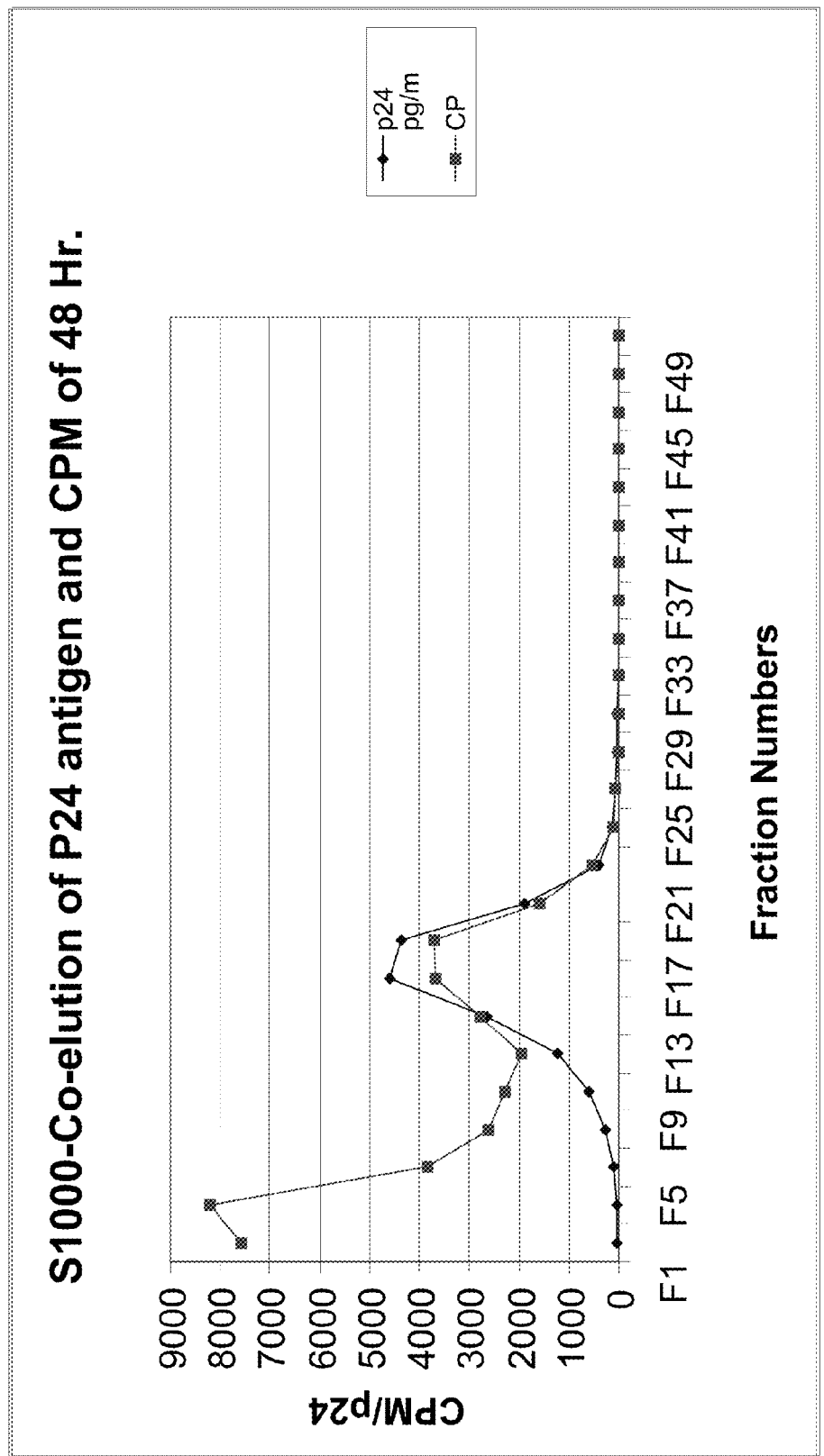
FIG. 13. Illustrates the elution profile of P24 antigen and CPMs.
Figure 14:
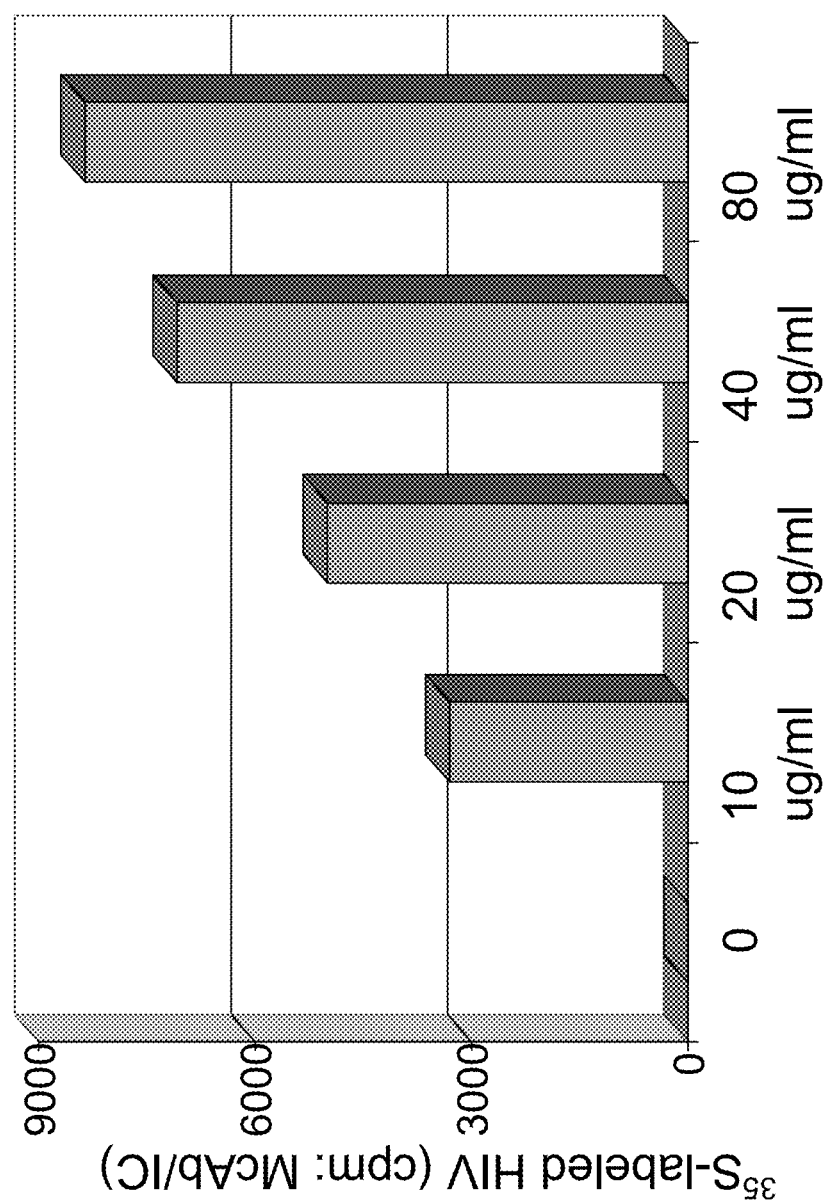
FIG. 14. Metabolically $^{35}$S-labeled HIV particles were partially purified by size-exclusion chromatography and incubated with either isotype control (IC) or anti-E2 McAb (concentrations indicated on X-axis). HIV-IgG complexes were immunoprecipitated using staph protein A (PAN-SORBIN®). Data represent HIV cpm precipitated by M6 (over background isotype control cpm).

To determine if the anti-E2 antibodies cross-react with HIV, the inventors infected GHOST CD4+ cells (Cecilia et al., 1998) with an R5 HIV isolate, and then grew the cells in methionine free media supplemented with $^{35}$S-methionine. Virus released into the culture supernatant was partially purified by size-exclusion chromatography (FIG. 13). The p24 antigen positive peak represents radiolabeled HIV particles, and SDS-PAGE demonstrated many $^{35}$S-labeled proteins, including proteins with relative molecular weights of 41 kD, 120 kD, and 160 kD consistent with HIV structural proteins (data not shown). The $^{35}$S-labeled material was incubated in normal mouse IgG overnight at 4° C., and material reacting with IgG non-specifically was removed by precipitation with staph protein A (PANSORBIN®). The supernatant was then incubated with either normal mouse IgG or murine anti-GBV-C E2 monoclonal antibody overnight (at various concentrations) at 4° C. Immune complexes were then precipitated using PANSORBIN®, and the pelleted IgG-HIV complexes were washed extensively. Following washing, radiolabeled material was released by adding SDS and boiling, and cpm released was counted. FIG. 14 demonstrates results for M6 antibody, showing a dose-dependent precipitation of radiolabeled HIV particles. Other anti-GBV-C E2 antibodies (including Biodesign, Virostat, M3, M5) immunoprecipitated HIV particles. For a positive control, a human anti-HIV monoclonal antibody and human HIV-negative antibodies were also tested, and confirmed that anti-HIV antibodies precipitated the radiolabeled HIV particles (data not shown).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,922,574
U.S. Pat. No. 4,275,149
U.S. Pat. No. 3,791,932
U.S. Pat. No. 3,817,837
U.S. Pat. No. 3,850,752
U.S. Pat. No. 3,939,350
U.S. Pat. No. 3,949,064
U.S. Pat. No. 3,996,345
U.S. Pat. No. 4,174,384
U.S. Pat. No. 4,196,265
U.S. Pat. No. 4,277,437
U.S. Pat. No. 4,366,241
U.S. Pat. No. 4,554,101
U.S. Pat. No. 4,676,980
U.S. Pat. No. 4,683,195
U.S. Pat. No. 4,683,202
U.S. Pat. No. 4,690,915
U.S. Pat. No. 4,800,159
U.S. Pat. No. 4,816,567
U.S. Pat. No. 4,833,077
U.S. Pat. No. 4,867,973
U.S. Pat. No. 4,879,236
U.S. Pat. No. 4,883,750
U.S. Pat. No. 4,946,773
U.S. Pat. No. 5,199,942
U.S. Pat. No. 5,279,721
U.S. Pat. No. 5,354,855
U.S. Pat. No. 5,359,046
U.S. Pat. No. 5,565,332
U.S. Pat. No. 5,582,981
U.S. Pat. No. 5,620,896
U.S. Pat. No. 5,650,298
U.S. Pat. No. 5,693,762
U.S. Pat. No. 5,714,153
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,336
U.S. Pat. No. 5,866,337
U.S. Pat. No. 5,866,366
U.S. Pat. No. 5,871,986
U.S. Pat. No. 5,874,563
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,925,517
U.S. Pat. No. 5,925,525
U.S. Pat. No. 5,925,565
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825
U.S. Pat. No. 5,939,291
U.S. Pat. No. 5,942,391
U.S. Pat. No. 5,958,895

U.S. Pat. No. 6,004,799
U.S. Pat. No. 6,399,763
U.S. Pat. No. 6,479,243
European Application 03089
European Application 320 308
European Application 329 822
GB Application 2 202 328
PCT Application PCT/US87/00880
PCT Application PCT/US89/01025
PCT Application WO 01/77157
PCT Application WO 88/10315
PCT Application WO 91/00360
PCT Application WO 92/200373
PCT Application WO 93/06213
PCT Application WO 93/08829
Akiyoshi et al., *Am. J. Gastroenterol.*, 94:1627-1631, 1999.
Almendro, et al., *J Immunol.*, 157(12):5411-21, 1996.
Alter et al., *N. Engl. J. Med.*, 336:741-746. 1997a.
Alter et al., *N. Engl. J. Med.*, 336:747-754. 1997b.
Anderson et al., *J. Immunol.*, 142, 1383, 1989.
Angel et al., *Mol. Cell. Biol.*, 7:2256, 1987a.
Angel et al., *Cell*, 49:729, 1987b.
Atchison and Perry, *Cell*, 46:253, 1986.
Atchison and Perry, *Cell*, 48:121, 1987.
Ausubel et al., In: *Current Protocols in Molecular Biology*, Greene Publishing Associates and Wiley Interscience, NY, 1989.
Baichwal and Sugden, In: *Gene Transfer*, Kucherlapati (Ed.), NY, Plenum Press, 117-148, 1986.
Banerji et al., *Cell*, 27(2 Pt 1):299-308, 1981.
Banerji et al., *Cell*, 33(3):729-740, 1983.
Bedzyk et al., *J. Biol. Chem.*, 265:18615, 1990
Berkhout et al., *Cell*, 59:273-282, 1989.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Brodeur et al., In: *Monoclonal antibody production techniques and applications*, Marcel Dekker, Inc., NY, 51-63, 1987.
Bukh et al., *J. Inf. Dis.*, 177:855-862, 1998.
Bulla and Siddiqui, *J. Virol.*, 62:1437, 1986.
Burbage et al., *Leuk Res*, 21(7):681-690, 1997.
Burger et al., *Antimicrob Agents Chemother.*, 37(7):1426-31, 1993.
Burton and Woof, *Adv. Immunol.*, 51:1-84, 1992.
Campbell and Villarreal, *Mol. Cell. Biol.*, 8:1993, 1988.
Campbell, In: *Monoclonal Antibody Technology, Laboratory Techniques in Biochemistry and Molecular Biology*, Burden and Von Knippenberg (Eds.), Elseview, Amsterdam, 13:71-74/75-83, 1984.
Campere and Tilghman, *Genes and Dev.*, 3:537, 1989.
Campo et al., *Nature*, 303:77, 1983.
Carbonell et al., *FEMS Microbiol. Lett.*, 177(1):75-82, 1999.
Cecilia et al., *Journal of Virology*, 72(9):6988-96, 1998.
Celander and Haseltine, *J. Virology*, 61:269, 1987.
Celander et al., *J. Virology*, 62:1314, 1988.
Chandler et al., *Cell*, 33:489, 1983.
Chandler et al., *Proc Natl. Acad. Sci. USA*, 94(8):3569-601, 1997.
Chang et al., *Mol. Cell. Biol.*, 9:2153, 1989.
Chatterjee et al., *Proc Natl. Acad. Sci. U.S.A.*, 86:9114, 1989.
Chaudhary et al., *Proc. Nat'l Acad. Sci.*, 87:9491, 1990
Chen and Okayama, *Mol. Cell Biol.*, 7:2745-2752, 1987.
Choi et al., *Cell*, 53:519, 1988.
Clackson et al., *Nature*, 352:624-628, 1991.
Cocea, *Biotechniques*, 23(5):814-6, 1997.
Cohen et al., *J. Cell. Physiol.*, 5:75, 1987.
Costa et al., *Mol. Cell. Biol.*, 8:81, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
Dawson et al., *J. Med. Virol.* 50:97-103, 1996.
de Martino et al., *J. Infect. Dis.*, 178:862-865, 1998.
De Villiers et al., *Nature*, 312(5991):242-246, 1984.
Deacon et al., *Science* 270:988-991, 1995.
Deschamps et al., *Science*, 230:1174-1177, 1985.
Easterbrook, *J. Infect.* 38:71-73, 1999.
Edbrooke et al., *Mol. Cell. Biol.*, 9:1908, 1989.
Edlund et al., *Science*, 230:912-916, 1985.
Elvander et al., *Acta. Vet. Scand.* 39:251-264, 1998.
Fechheimer et al., *Proc. Nat'l Acad. Sci. USA*, 84:8463-8467, 1987.
Feng and Holland, *Nature*, 334:6178, 1988.
Feucht et al., *Hepatology*, 26:491-494, 1997.
Firak and Subramanian, *Mol. Cell. Biol.*, 6:3667, 1986.
Foecking and Hofstetter, *Gene*, 45(1):101-105, 1986.
Fogeda et al., *J. Virol.* 73:4052-4061, 1999.
Forster and Symons, *Cell*, 49:211-220, 1987.
Fraley et al., *Proc. Natl. Acad. Sci. USA*, 76:3348-3352, 1979.
Freshney, In: *Animal Cell Culture: a Practical Approach*, Second Edition, Oxford/NY, IRL Press, Oxford University Press, 1992.
Fujita et al., *Cell*, 49:357, 1987.
Gale, Jr. et al., *Mol. Cell. Biol.*, 18:5208-5218, 1998
Gefter et al., *Somatic Cell Genet.*, 3(2):231-6, 1977.
Ghosh and Bachhawat, In: *Liver diseases, targeted diagnosis and therapy using specific receptors and ligands*, (Wu G, Wu C ed.), NY, Marcel Dekker, 87-104, 1991.
Gilles et al., *Cell*, 33:717, 1983.
Gloss et al., *EMBO J.*, 6:3735, 1987.
Godbout et al., *Mol. Cell. Biol.*, 8:1169, 1988.
Goding et al., In: *Monoclonal Antibodies: Principles and Practice*, 2d ed., Orlando, Fla., Academic Press, 60-61, 65-66, 71-74, 1986.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Gossen et al., *Proc. Natl. Acad. Sci. USA*, 89:5547-5551, 1992.
Gossen et al., *Science*, 268:1766-69, 1995.
Graham and Van Der Eb, *Virology*, 52:456-467, 1973.
Greene et al., *Immunology Today*, 10:272, 1989
Griffith et al., *EMBO J.*, 12:725-734, 1993.
Grosschedl and Baltimore, *Cell*, 41:885, 1985.
Harland and Weintraub, *J. Cell Biol.*, 101:1094-1099, 1985.
Harlow and Lane, Antibodies: A Laboratory manual, Cold Spring Harbor Laboratory, 1988.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Hoon et al., *J. Urol.*, 150(6):2013-2018, 1993.
Horlick and Benfield, *Mol. Cell. Biol.*, 9:2396, 1989.
Huang et al., *Cell*, 27:245, 1981.

Huang et al., *Nature Med.*, 2:1240-1243, 1996.
Hug et al., *Mol. Cell. Biol.*, 8:3065, 1988.
Humphreys and Glover, *Curr Opin Drug Discov Devel.*, 4(2):172-185, 2001.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol*, 7:2558, 1987.
Imperiale and Nevins, *Mol. Cell. Biol.*, 4:875, 1984.
Jakobovits et al., *Mol. Cell. Biol.*, 8:2555, 1988.
Jakobovits et al., *Nature* 362, 255-258, 1993.
Jameel and Siddiqui, *Mol. Cell. Biol.*, 6:710, 1986.
Jaynes et al., *Mol. Cell. Biol.*, 8:62, 1988.
Johnson et al., In: *Biotechnology And Pharmacy*, Pezzuto et al., (Eds.), Chapman and Hall, NY, 1993.
Johnson et al., *Mol. Cell. Biol.*, 9:3393, 1989.
Jones et al., *Nature*, 321:522-525, 1986.
Kadesch and Berg, *Mol. Cell. Biol.*, 6:2593, 1986.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Katinka et al., *Cell*, 20:393, 1980.
Kawamoto et al., *Mol. Cell. Biol.*, 8:267, 1988.
Kiledjian et al., *Mol. Cell. Biol.*, 8:145, 1988.
Klamut et al., *Mol. Cell. Biol.*, 10:193, 1990.
Koch et al., *Mol. Cell. Biol.*, 9:303, 1989.
Kohler and Milstein, *Eur. J. Immunol.*, 6:511-519, 1976.
Kohler and Milstein, *Nature*, 256:495-497, 1975.
Kozbor, *J. Immunol.*, 133:3001, 1984.
Kraus et al., *FEBS Lett.*, 428(3):165-70, 1998.
Kriegler and Botchan, In: *Eukaryotic Viral Vectors*, Y. Gluzman, ed., Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Kwoh et al., *Proc. Natl. Acad. Sci. USA*, 86(4):1173-1177, 1989.
Kyte and Doolittle, *J. Mol. Biol.*, 157:105-132, 1982.
Lareyre, et al., *J. Bio. Chem.*, 274(12):8282-90, 1999.
Larsen et al., *Proc Natl Acad. Sci. USA.*, 83:8283, 1986.
Laskus et al., *J. Virol.*, 72:3072-3075. 1998.
Laspia et al., *Cell*, 59:283, 1989.
Latimer et al., *Mol. Cell. Biol.*, 10:760, 1990.
Leary et al., *J. Med. Virol.*, 48:60-67. 1996.
Lee et al., *Mol. Endocrinol.*, 2: 404-411, 1988.
Lee et al., *Nature*, 294:228, 1981.
Lee et al., *Nucleic Acids Res.*, 12:4191-206, 1984.
Lefrère et al., *J. Infect. Dis.*, 179:783-789, 1999.
Levenson et al., *Hum. Gene Ther.*, 9(8):1233-6, 1998.
Levinson et al., *Nature*, 295:79, 1982.
Lidor et al., *Am. J. Obstet. Gynecol.*, 177(3):579-585, 1997.
Lin et al., *Mol. Cell. Biol.*, 10:850, 1990.
Linnen et al., *Science*, 271:505-508. 1996.
Loeffler et al., *Cancer Res.*, 51:2127, 1991.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.* 3:1108, 1983.
Macejak et al., *Nature*, 353:90-94, 1991.
Majors and Varmus, *Proc. Natl. Acad. Sci. USA*, 80:5866, 1983.
Maniatis, et al., Molecular Cloning, A Laboratory Manual, Cold Spring Harbor Press, Cold Spring Harbor, N.Y. 1988.
Marks et al., *Bio/Technol.*, 10:779-783, 1992.
Marks et al., *J. Mol. Biol.*, 222:581-597, 1991.
Massuda et al., *Proc Natl Acad Sci USA*, 94(26):14701-14706, 1997.
McCafferty et al., *Nature*, 348:552-553, 1990.
McNeall et al., *Gene*, 76:81, 1989.
Miksicek et al., *Cell*, 46:203, 1986.
Millstein and Cuello, Nature, 305:537-539, 1983.
Moore et al., *N. Engl. J. Med.*, 324(20):1412-1416, 1991.
Mordacq and Linzer, *Genes and Dev.*, 3:760, 1989.
Moreau et al., *Nucl. Acids Res.*, 9:6047, 1981.
Muesing et al., *Cell*, 48:691, 1987.
Nerurkar et al., *J. Med. Virol.*, 56:123-127, 1998.
Ng et al., *Nuc. Acids Res.*, 17:601, 1989.
Nicolas and Rubenstein, In: *Vectors: A survey of molecular cloning vectors and their uses*, Rodriguez and Denhardt (eds.), Stoneham: Butterworth, 493-513, 1988.
Nicolau and Sene, *Biochim. Biophys. Acta*, 721:185-190, 1982.
Nomoto et al., *Gene*, 236(2):259-271, 1999.
Okamoto et al., *J. Gen. Virol.*, 78:737-745. 1997.
Ondek et al., *EMBO J.*, 6:1017, 1987.
Ornitz et al., *Mol. Cell. Biol.*, 7:3466, 1987.
Palmiter et al., *Nature*, 300:611, 1982.
Pech et al., *Mol. Cell. Biol.*, 9:396, 1989.
Pelletier et al., *Nature*, 334(6180):320-325, 1988.
Perez-Stable and Constantini, *Mol. Cell. Biol.*, 10:1116, 1990.
Pessoa et al., *Hepatol.*, 27:877-880, 1998.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Nat'l Acad. Sci. USA*, 81:7161-7165, 1984.
Queen and Baltimore, *Cell*, 35:741, 1983.
Quinn et al., *Mol. Cell. Biol.*, 9:4713, 1989.
Redondo et al., *Science*, 247:1225, 1990.
Reisman and Rotter, *Mol. Cell. Biol.*, 9:3571, 1989.
Remington's Pharmaceutical Sciences, 18th Ed. Mack Printing Company, 1389-1404, 1990,
Resendez Jr. et al., *Mol. Cell. Biol.*, 8:4579, 1988.
Ridgeway, In: *Vectors: A survey of molecular cloning vectors and their uses*, Rodriguez and Denhardt (Eds.), Stoneham:Butterworth, 467-492, 1988.
Riechmann et al., *Nature*, 332:323-327, 1988.
Rinaldo, Jr. et al., *Infect. Immun.*, 14:660-666, 1976.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Robertson et al., *Arch. Virol.*, 143:2493-2503, 1998.
Rosen et al., *Cell*, 41:813, 1988.
Rowland-Jones, *J. Infect.*, 38:67-70, 1999.
Sabin et al., *J. Acquir. Immune Defic. Syndr.*, 19:546-547, 1998.
Sakai et al., *Genes and Dev.*, 2:1144, 1988.
Sambrook et al., In: *Molecular Cloning: A Laboratory Manual*, Vol. 1, Cold Spring Harbor Laboratory Press, Cold Spring Harbor, N.Y., 7(7)19-17.29, 1989.
Satake et al., *J. Virology*, 62:970, 1988.
Sawyer et al., *AIDS Res. Hum. Retroviruses*, 6(3):341-356, 1990.
Schaffner et al., *J. Mol. Biol.*, 201:81, 1988.
Schmolke et al., *J. Virol.*, 72(5):4541-5, 1998.
Searle et al., *Mol. Cell. Biol.*, 5:1480, 1985.
Seipp et al., *J. Hepatol.*, 30:570-579, 1999.
Sharp and Marciniak, *Cell*, 59:229, 1989.

Shaul and Ben-Levy, *EMBO J.*, 6:1913, 1987.
Sherman et al., *Mol. Cell. Biol.*, 9:50, 1989.
Shimizu, *J. Virol.*, 73:8411-8414, 1999.
Simons et al., *J. Virol.*, 70:6126-6135. 1996.
Simons et al., *Nature Med.*, 1:564-569, 1995a.
Simons et al., *Proc. Natl. Acad. Sci. USA*, 92:3401-3405, 1995b.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stuart et al., *Nature*, 317:828, 1985.
Sullivan and Peterlin, *Mol. Cell. Biol.*, 7:3315, 1987.
Suresh et al., *Methods in Enzymology*, 121:210-228, 1986.
Swartzendruber and Lehman, *J. Cell. Physiology*, 85:179, 1975.
Tacke et al., *Hepatol.*, 26:1626-1633, 1997.
Takebe et al., *Mol. Cell. Biol.*, 8:466, 1988.
Tanaka et al., *J. Hepatol.*, 27:1110-1112, 1997.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Taylor et al., *Science* 285:107-110, 1999.
Temin, In: *Gene Transfer*, Kucherlapati (ed.), NY: Plenum Press, 149-188, 1986.
Thiesen et al., *J. Virology*, 62:614, 1988.
Thomas et al., *J. Infect. Dis.*, 177:539-542, 1998.
Toyoda et al., *J. Acquir. Immune Defic. Syndr.*, 17:209-213, 1998.
Traunecker et al., *EMBO*, 10:3655-3659, 1991.
Treisman, *Cell*, 42:889, 1985.
Tronche et al., *Mol. Biol. Med.*, 7:173, 1990.
Trudel and Constantini, *Genes and Dev.*, 6:954, 1987.
Tsumaki et al., *J. Biol. Chem.*, 273(36):22861-22864, 1998.
Tur-Kaspa et al., *Mol. Cell. Biol.*, 6:716-718, 1986.
Tyndell et al., *Nuc. Acids. Res.*, 9:6231, 1981.
Vannice and Levinson, *J. Virology*, 62:1305, 1988.
Vasseur et al., *Proc Natl. Acad. Sci. USA*, 77:1068, 1980.
Verhoeyen et al., *Science*, 239:1534-1536, 1988.
Wang and Calame, *Cell*, 47:241, 1986.
Waterhouse et al., *Nucl. Acids Res.*, 21:2265-2266, 1993.
Weber et al., *Cell*, 36:983, 1984.
Weinberger et al. *Mol. Cell. Biol.*, 8:988, 1984.
Winoto and Baltimore, *Cell*, 59:649, 1989.
Wu and Wu, *Biochem.*, 27:887-892, 1988.
Wu and Wu, *J. Biol. Chem.*, 262:4429-4432, 1987.
Wu et al., *Biochem. Biophys. Res. Commun.*, 233(1):221-6, 1997.
Wu et al., *J. Med. Virol.*, 52:83-85. 1997.
Xiang et al., *J. Viral Hepat.*, 6:S16-S22, 1999.
Yang et al., *Proc. Nat'l Acad. Sci USA*, 87:9568-9572, 1990.
Yutzey et al. *Mol. Cell. Biol.*, 9:1397, 1989.
Zhao-Emonet, et al., *Biochim. Biophys. Acta*, 1442(2-3):109-19, 1998.

What is claimed is:

1. A method of inducing a cross-reactive anti-HIV-1 immune response in a subject comprising contacting said subject with an immunogenic composition comprising a GBV-C E2 polypeptide or fragment thereof comprising an epitope defined by GGAGLTGGFYEPLVRRC (SEQ ID NO:7) dispersed in a pharmaceutical carrier, buffer or medium.

2. The method of claim 1, wherein said immunogenic composition further comprises an adjuvant.

3. The method of claim 1, wherein said immunogenic composition comprises a full length GBV-C E2 polypeptide.

4. The method of claim 1, wherein said immunogenic composition comprises GBV-C E2 fragment.

5. The method of claim 1, wherein the polypeptide or fragment is linked to a carrier molecule.

* * * * *

UNITED STATES PATENT AND TRADEMARK OFFICE
CERTIFICATE OF CORRECTION

PATENT NO.        : 10,034,936 B2
APPLICATION NO.   : 14/460517
DATED             : July 31, 2018
INVENTOR(S)       : Jack T. Stapleton et al.

It is certified that error appears in the above-identified patent and that said Letters Patent is hereby corrected as shown below:

On the Title Page

Item (73) Assignees, Line 2, delete "Iowa" and replace with --Iowa City-- therefor.

In the Specification

In Column 1, Lines 15-17, delete the entire contents and insert --This invention was made with government support under Grant No. AA012671 awarded by the National Institutes of Health. The government has certain rights in the invention.-- therefor.

Signed and Sealed this
Sixth Day of November, 2018

Andrei Iancu
*Director of the United States Patent and Trademark Office*